(12) United States Patent
McCormick et al.

(10) Patent No.: US 10,201,516 B2
(45) Date of Patent: Feb. 12, 2019

(54) TARGETING K-RAS-MEDIATED SIGNALING PATHWAYS AND MALIGNANCY BY PROSTRATIN

(71) Applicant: The Regents of the University of California, Oakland, CA (US)

(72) Inventors: Frank McCormick, San Francisco, CA (US); Man-Tzu Wang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/508,025

(22) PCT Filed: Sep. 10, 2015

(86) PCT No.: PCT/US2015/049459
§ 371 (c)(1),
(2) Date: Mar. 1, 2017

(87) PCT Pub. No.: WO2016/040656
PCT Pub. Date: Mar. 17, 2016

(65) Prior Publication Data
US 2017/0326093 A1  Nov. 16, 2017

Related U.S. Application Data

(60) Provisional application No. 62/048,761, filed on Sep. 10, 2014.

(51) Int. Cl.
| | | |
|---|---|---|
| A61K 31/22 | (2006.01) |
| A61K 31/25 | (2006.01) |
| C07C 69/013 | (2006.01) |
| A61K 45/06 | (2006.01) |
| A61K 31/7068 | (2006.01) |
| A61K 9/00 | (2006.01) |

(52) U.S. Cl.
CPC ............ *A61K 31/22* (2013.01); *A61K 9/0019* (2013.01); *A61K 9/0053* (2013.01); *A61K 31/25* (2013.01); *A61K 31/7068* (2013.01); *A61K 45/06* (2013.01); *C07C 69/013* (2013.01); *C07C 2603/30* (2017.05)

(58) Field of Classification Search
CPC ....... A61K 31/25; A61K 31/22; C07C 69/013
See application file for complete search history.

(56) References Cited

U.S. PATENT DOCUMENTS

| 5,021,549 | A | 6/1991 | Takeuchi et al. |
| 8,536,378 | B2 | 9/2013 | Wender et al. |
| 2011/0014699 | A1 | 1/2011 | Wender et al. |
| 2011/0224297 | A1 | 9/2011 | Brown et al. |
| 2014/0018329 | A1 | 1/2014 | Han et al. |

FOREIGN PATENT DOCUMENTS

| WO | 2009126949 A1 | 10/2009 |
| WO | 2013110006 A2 | 7/2013 |
| WO | 2016040656 A1 | 3/2016 |

OTHER PUBLICATIONS

Neuzillet et al., "Targeting the Ras—ERK pathway in pancreatic adenocarcinoma" Cancer Metastasis Reviews vol. 32 pp. 147-162 (Year: 2013).*
Shen et al., "Sensitization of Human Pancreatic Cancer Cells Harboring Mutated K-ras to Apoptosis" PLOS One vol. 7 issue 7 pp. 1-10 (Year: 2012).*
Beans, et al., "Highly potent, synthetically accessible prostratin analogs induce latent HIV expression in vitro and ex vivo," PNAS, Jul. 16, 2013, 110(29):11698-11703.
Bivona et al., "PKC Regulates a Farnesyl-Electrostatic Switch on K-Ras that Promotes its Association with Bcl-XL on Mitochondria and Induces Apoptosis," *Molecular Cell* 21, Feb. 17, 2006, 481-493.
Downward, "Targeting Ras Signalling Pathways in Cancer Therapy," Nature Reviews Cancer, Jan. 2003, 3:11-22.
Hezel et al., "Genetics and biology of pancreatic adenocarcinoma," *Genes & Development*, 20:1218-1249 (2006), Cold Spring Harbor Laboratory Press ISSN 0890-93969/06; www.genesdev.org.
Karnoub et al., "Ras oncogenes: split personalities," *Nature Reviews Molecular Cell Biology*, Jul. 2008, 9:517-531.
Palmioli et al., "Selective cytotoxicity of a bicyclic Ras inhibitor in cancer cells expressing K-Ras$^{G13D}$," *Biochem. Biophys. Res. Commun.*, vol. 386, No. 4,. Sep. 4, 2009, pp. 593-597 Abstract.
Stephen et al., "Dragging Ras Back in the Ring," Cancer Cell 25, Mar. 27, 2014, 272-281.
Szallasi et al., "Prostratin, a Nonpromoting Phorbol Ester, Inhibits Induction by Phorbol 12-Myristate 13-Acetate of Ornithine Decarboxylase, Edema, and Hyperplasia in CD-1 Mouse Skin", *Cancer Research*,vol. 51, Oct. 1, 1991, pp. 5355-5360.
Wender et al., "Practical Synthesis of Prostratin, DPP, and Their Analogs, Adjuvant Leads Against Latent HIV," NIH Public Access Author Manuscript, *Science*, Available in PMC Jul. 2, 2009, pp. 1-9; Published in final edited form as: *Science*. May 2, 2008; 320(5876): 649-652. doi:10.1126/science.1154690.
PCT/US2015/049459, "International Search Report and Written Opinion", dated Nov. 19, 2015, 9 pages.
Bond et al., "Cytotoxic Action of Phorbol Esters on Human Pancreatic Cancer Cells", International Journal of Cancer, vol. 121, No. 7, Jan. 1, 2007, pp. 1445-1454.
Fernandez-Medarde et al., "Ras in Cancer and Developmental Diseases", Genes and Cancer, vol. 2, No. 3, Mar. 1, 2011, pp. 344-358.
Wang et al., "K-Ras Promotes Tumorigenicity through Suppression of Non-canonical Wnt Signaling", Cell, vol. 163, No. 5, Nov. 19, 2015, pp. 1237-1251.

(Continued)

*Primary Examiner* — Eric Olson
(74) *Attorney, Agent, or Firm* — Kilpatrick Townsend & Stockton LLP

(57) ABSTRACT

The present invention provides method of treating a K-Ras-expressing cancer in a subject comprising administering to the subject a therapeutic amount of prostratin or a prostratin analog, or a salt or isomer thereof. Compositions and kits for treating a K-Rasexpressing cancer in a subject are also provided.

14 Claims, 71 Drawing Sheets
Specification includes a Sequence Listing.

(56) References Cited

OTHER PUBLICATIONS

EP15839485.8 , "Extended European Search Report", dated Mar. 23, 2018, 11 pages.

* cited by examiner

F

E
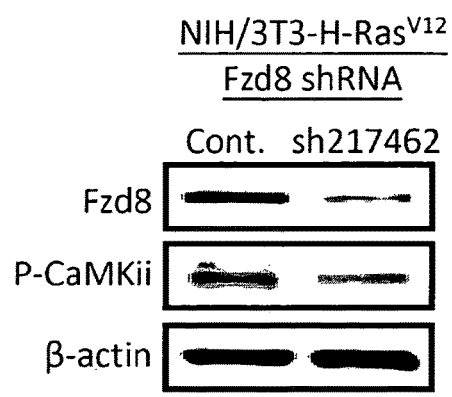
F
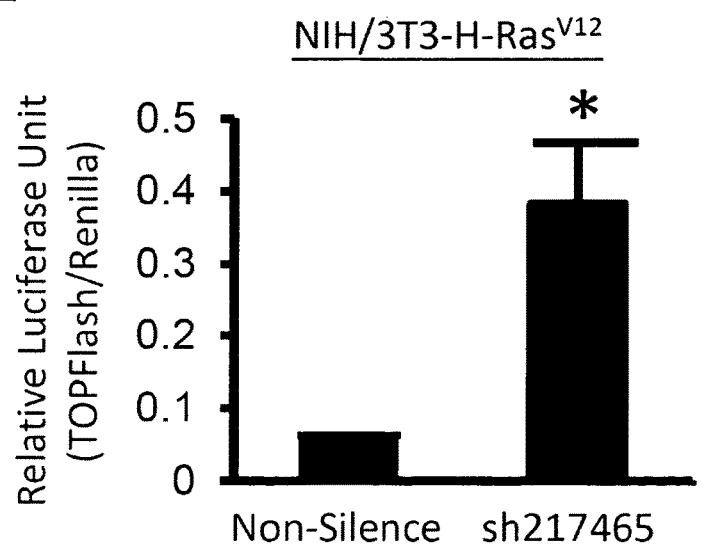

D

E

H

I

E

| Recipients with Developments of O.T Tumors from PANC2.13 (30th Day) | | |
|---|---|---|
| | Vehicle | Prostratin |
| 10⁵ cells | 4/4 | 2/6 |
| Metastasis | 4/4 | 0/6 |

D

E

F

E

F

TARGETING K-RAS-MEDIATED SIGNALING PATHWAYS AND MALIGNANCY BY PROSTRATIN

CROSS-REFERENCES TO RELATED APPLICATIONS

This application is a U.S. National Phase application under 35 U.S.C. § 371 of PCT/US2015/049459, filed Sep. 10, 2015, which claims priority to U.S. Provisional Application No. 62/048,761, filed Sep. 10, 2014, the entire content of each of which is incorporated by reference herein for all purposes.

REFERENCE TO SEQUENCE LISTING

This application includes a Sequence Listing as a text file named "081906-218810US-1035850_SequenceListing.txt" created Jul. 17, 2017, and containing 1,915 bytes. The material contained in this text file is incorporated by reference in its entirety for all purposes.

BACKGROUND OF THE INVENTION

Pancreatic cancer is a cancer that often has a poor prognosis, even when detected in its early stages. It is estimated that for all stages of pancreatic cancer combined, only 6% of patients survive five years after diagnosis. The most common form of pancreatic cancer, pancreatic ductal adenocarcinoma (PDAC), is known to have an extremely poor prognosis. Although survival time improves for patients who undergo a surgical resection, PDAC frequently is not diagnosed in time for surgical resection to be feasible.

The oncogene K-Ras is frequently mutated in cancers, such as pancreatic, lung, and colorectal cancers, with activating K-Ras mutations present in over 90% of PDACs. However, to date there have been no successes in developing small molecule inhibitors that directly block K-Ras function and show efficacy in pre-clinical models.

BRIEF SUMMARY OF THE INVENTION

In one aspect, methods of treating a cancer in a subject are provided. In some embodiments, the method comprises administering to the subject a therapeutic amount of prostratin or a prostratin analog, or a salt or isomer thereof.

In some embodiments, the cancer is a K-Ras-expressing cancer. In some embodiments, the K-Ras-expressing cancer is a cancer that expresses wild-type K-Ras. In some embodiments, the K-Ras-expressing cancer is a cancer that expresses a mutated K-Ras.

In some embodiments, the cancer is a pancreatic cancer, a colorectal cancer, or a lung cancer. In some embodiments, the cancer is pancreatic cancer (e.g., pancreatic ductal adenocarcinoma).

In some embodiments, prostratin, or a salt or isomer thereof, is administered to the subject. In some embodiments, a prostratin analog, or a salt or isomer thereof, is administered to the subject. In some embodiments, the prostratin analog has the structural formula:

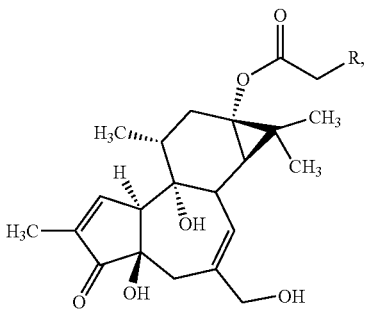

wherein R is ethyl, formate, propionate, butyrate, pentanoate, hexanoate, benzoate, phenyl acetate, cyclohexyl acetate, pentafluorophenyl acetate, 1-Naphthyl acetate, 2-Naphthyl acetate, (5,6,7,8)Tetrahydro-1-naphthyl acetate, biphenyl acetate, adamantyl acetate, or p-Benzyl phenyl acetate.

In some embodiments, the prostratin or the prostratin analog, or a salt or isomer thereof, is administered orally, intravenously, or intraperitoneally.

In some embodiments, the prostratin or the prostratin analog, or a salt or isomer thereof, is administered in combination with a chemotherapeutic agent. In some embodiments, the chemotherapeutic agent is gemcitabine. In some embodiments, the prostratin or the prostratin analog, or a salt or isomer thereof, and the chemotherapeutic agent are administered concurrently. In some embodiments, the prostratin or the prostratin analog, or a salt or isomer thereof, and the chemotherapeutic agent are administered sequentially.

In another aspect, compositions and kits for treating a cancer are provided. In some embodiments, the composition or kit comprises:

prostratin or a prostratin analog, or a salt or isomer thereof; and a chemotherapeutic agent.

In some embodiments, the composition or kit is for treating a cancer that is a K-Ras-expressing cancer. In some embodiments, the K-Ras-expressing cancer is a cancer that expresses wild-type K-Ras. In some embodiments, the K-Ras-expressing cancer is a cancer that expresses a mutated K-Ras. In some embodiments, the composition or kit is for treating a cancer that is a pancreatic cancer, a colorectal cancer, or a lung cancer. In some embodiments, the composition or kit is for treating a cancer that is pancreatic cancer (e.g., pancreatic ductal adenocarcinoma).

In some embodiments, the composition or kit comprises prostratin, or a salt or isomer thereof. In some embodiments, the composition or kit comprises a prostratin analog as described herein, or a salt or isomer thereof.

In some embodiments, the chemotherapeutic agent is gemcitabine.

In another aspect, compositions comprising prostratin or a prostratin analog, or a salt or isomer thereof, for use in treating a cancer are provided. In some embodiments, the cancer is pancreatic cancer (e.g., pancreatic ductal adenocarcinoma). In some embodiments, the cancer is a K-Ras-expressing cancer. In some embodiments, the K-Ras-expressing cancer is a cancer that expresses wild-type K-Ras. In some embodiments, the K-Ras-expressing cancer is a cancer that expresses a mutated K-Ras. In some embodiments, the composition comprising prostratin or a prostratin analog is used in combination with a chemotherapeutic agent. In some embodiments, the composition comprising prostratin or a prostratin analog further comprises a chemotherapeutic agent. In some embodiments, the chemotherapeutic agent is gemcitabine.

In still another aspect, the use of a composition comprising prostratin or a prostratin analog, or a salt or isomer thereof, for the manufacture of a medicament for the treatment of a cancer is provided. In some embodiments, the cancer is pancreatic cancer (e.g., pancreatic ductal adenocarcinoma). In some embodiments, the cancer is a K-Ras-expressing cancer. In some embodiments, the K-Ras-expressing cancer is a cancer that expresses wild-type K-Ras. In some embodiments, the K-Ras-expressing cancer is a cancer that expresses a mutated K-Ras. In some embodiments, the composition comprising prostratin or a prostratin analog further comprises a chemotherapeutic agent. In some embodiments, the chemotherapeutic agent is gemcitabine.

DETAILED DESCRIPTION OF THE INVENTION

I. Introduction

Figure 1:
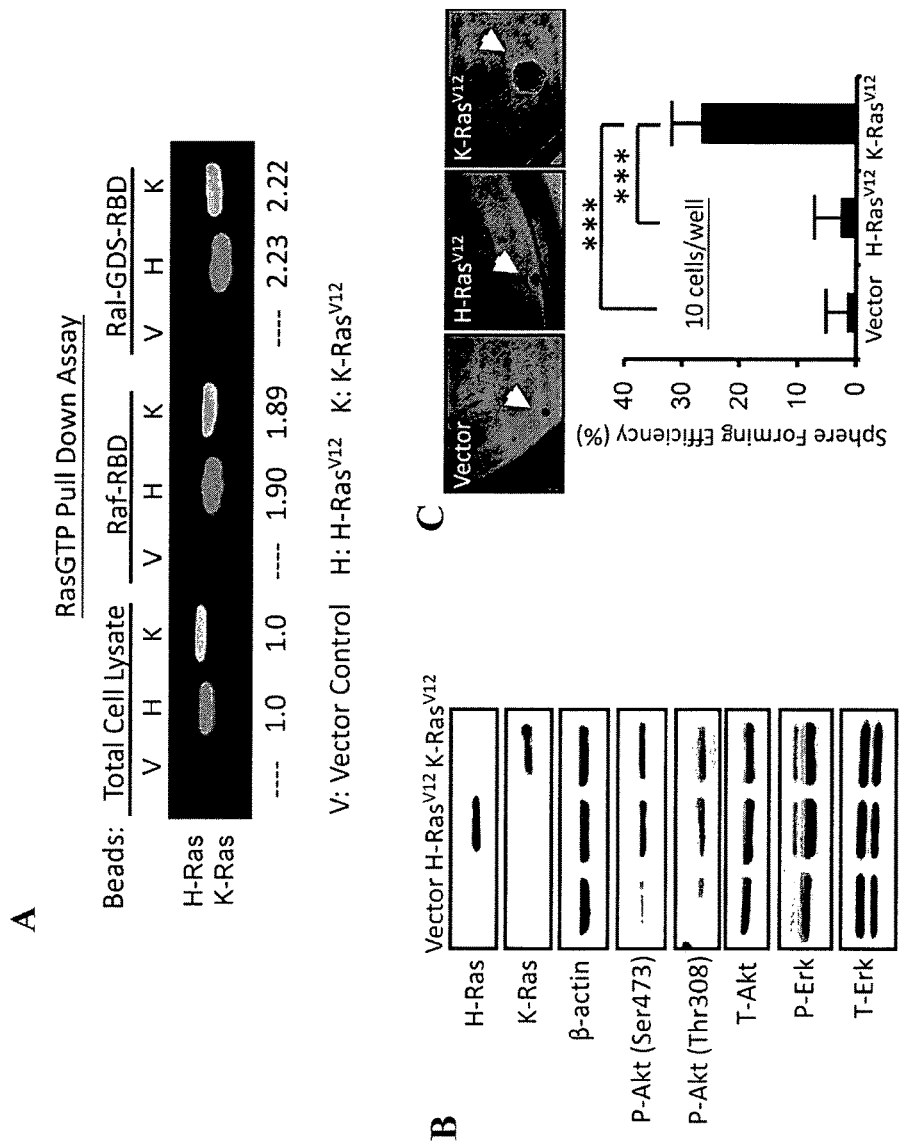
FIG. 1. K-Ras$^{V12}$ and H-Ras$^{V12}$ have different tumor initiating properties, despite comparable canonical signaling outputs. (A) Comparable levels of total Ras proteins and GTP-bound Ras as measured by Raf-RBD or Ral-GDS-RBD pull-down assays. (B) Comparable levels of phosphorylated Erk and Akt in cells transformed by H-Ras$^{V12}$ or K-Ras$^{V12}$. (C) K-Ras$^{V12}$-transformed NIH3T3 cells presented increased sphere formation. Left panel: Gross morphology of spheres formed. Right panel: Sphere formation efficiency (N=6). (D) The tumor initiating abilities of H-Ras$^{V12}$ and K-Ras$^{V12}$-transformed NIH/3T3 cells when the number of injected cells was 1,000 (top left) or 100 (Top right). K-Ras$^{V12}$-transformed cells presented increased tumor initiating capacity, in comparison with H-Ras$^{V12}$-transformed cells, when the number of cells injected became limited (bottom table). (E) Promotion of BxPC3 sphere formation by EGF. Top panel: morphology of spheres formed. Bottom panel: sphere formation efficiency as calculated by the number of spheres normalized by the number of cells seeded (N=6). (F) Knockdown of K-Ras, but not H-Ras, attenuated EGF-stimulation of BxPC3 sphere formation (bottom panel) or enhancement of sphere forming efficiency (top panel) (N=6). (G) Knockdown of mutant K-Ras repressed PANC1 sphere formation efficiency. Left up panel: western blot confirmed the knockdown efficiency. Left bottom and right panel: PANC1 with K-Ras shRNA expression formed spheres in smaller sizes and numbers when compared to vector control (N=6). (H) Knockdown of mutant K-Ras reduced PANC1 tumor initiating capacity. Left panel: tumor free survival curve. Right panel: tumor formation frequency. N.S. No Significance; * $P<0.05$;  $P<0.01$; * $P<0.001$; **** $P<0.0001$.
Figure 1:
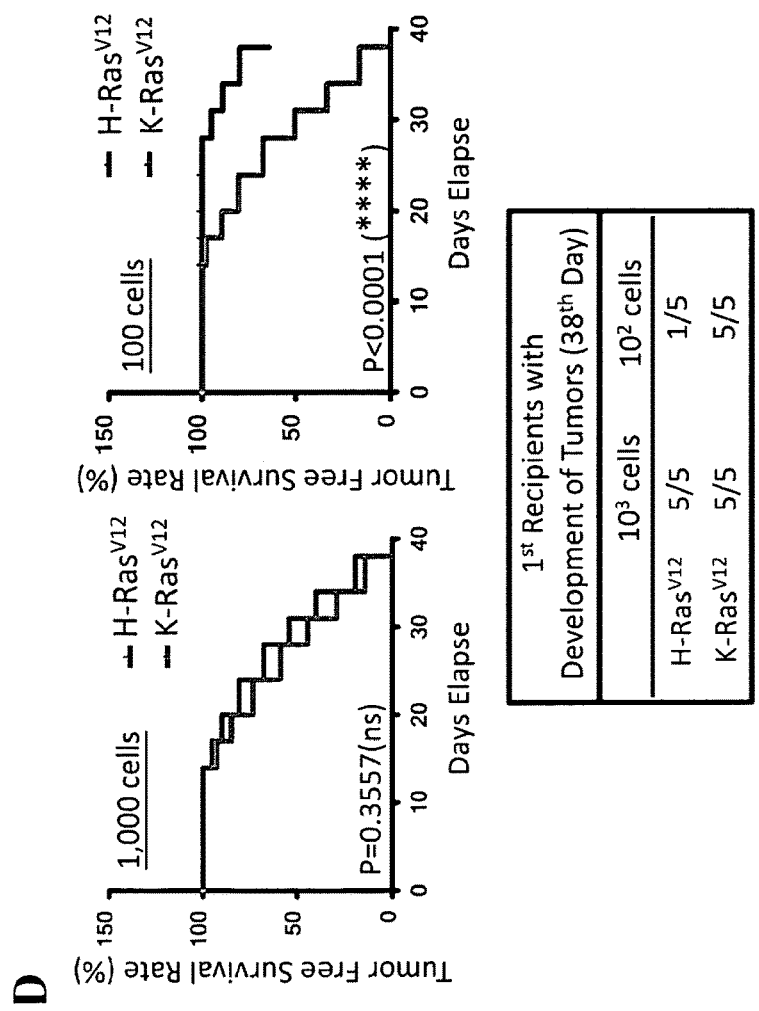
Figure 1:
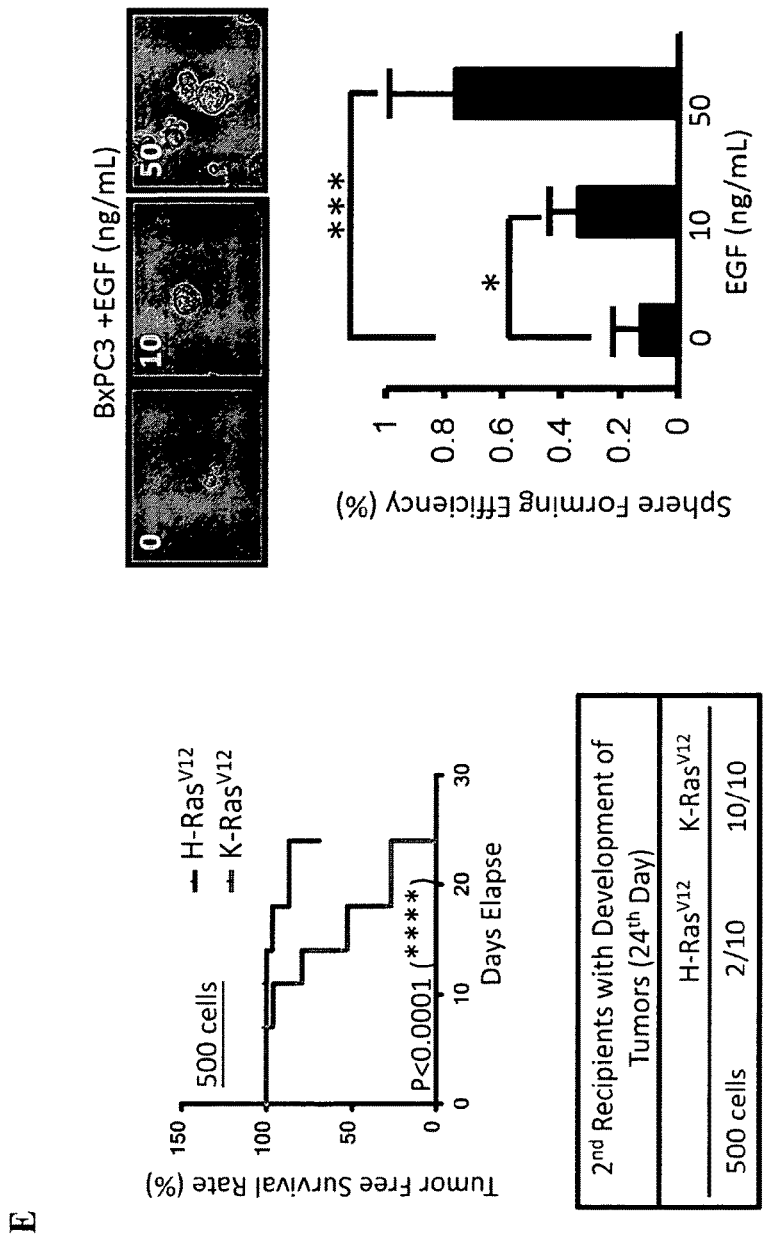
Figure 1:
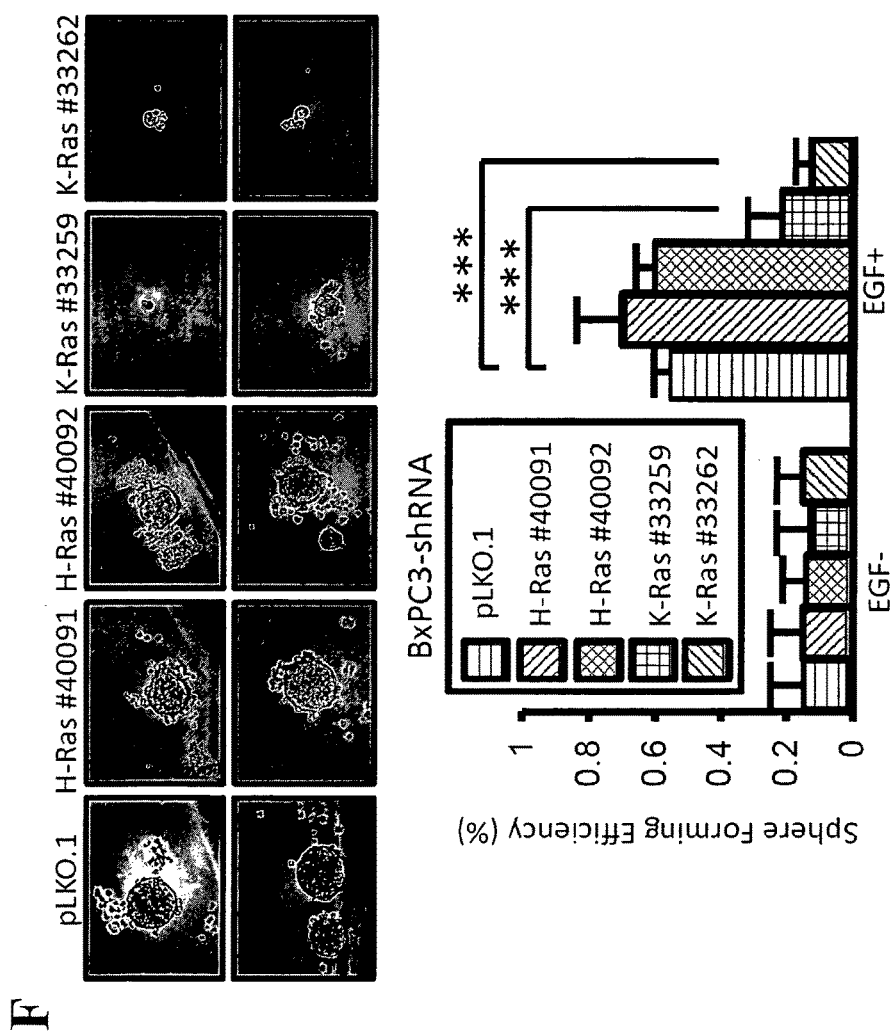
Figure 1:
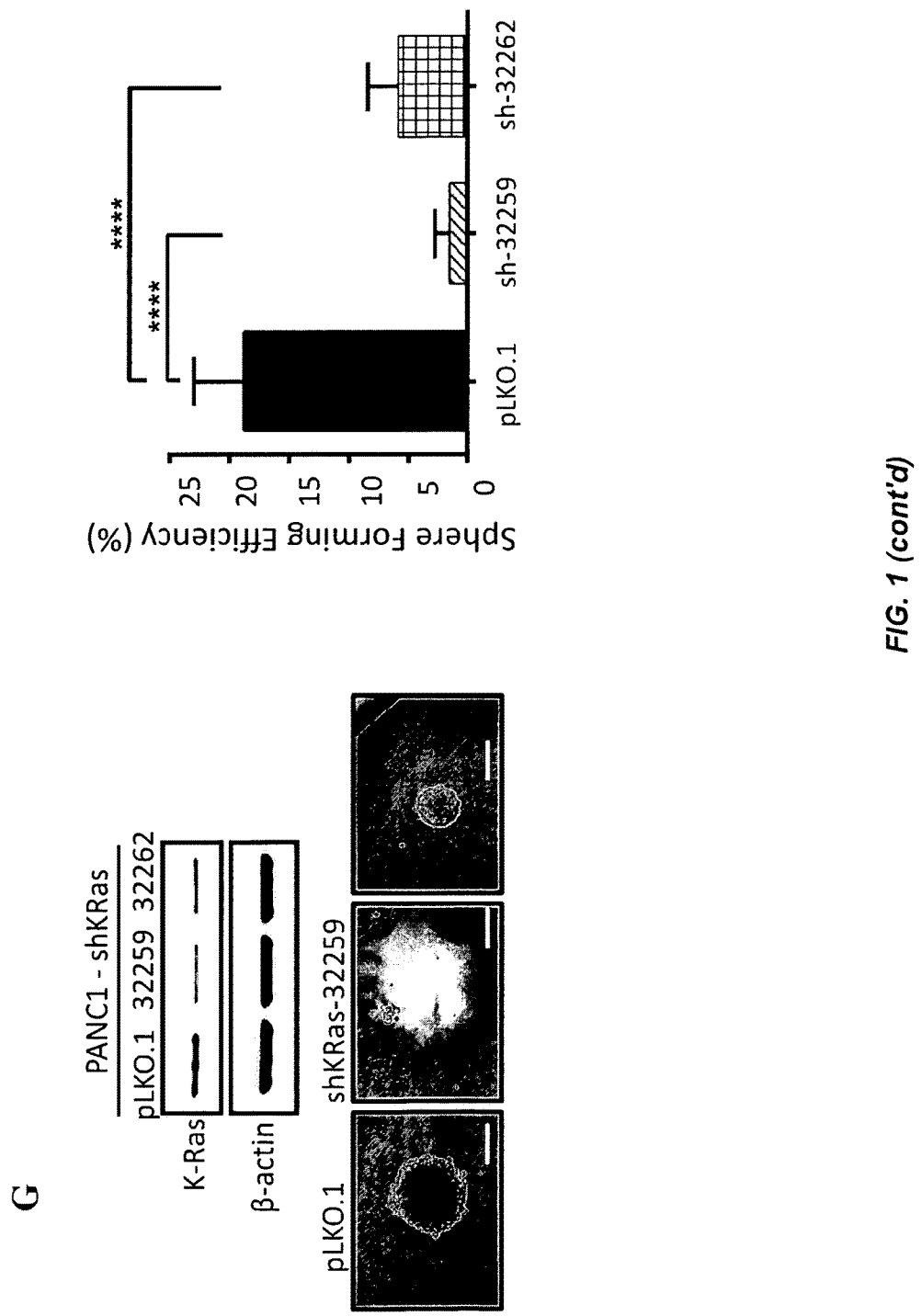
Figure 1:
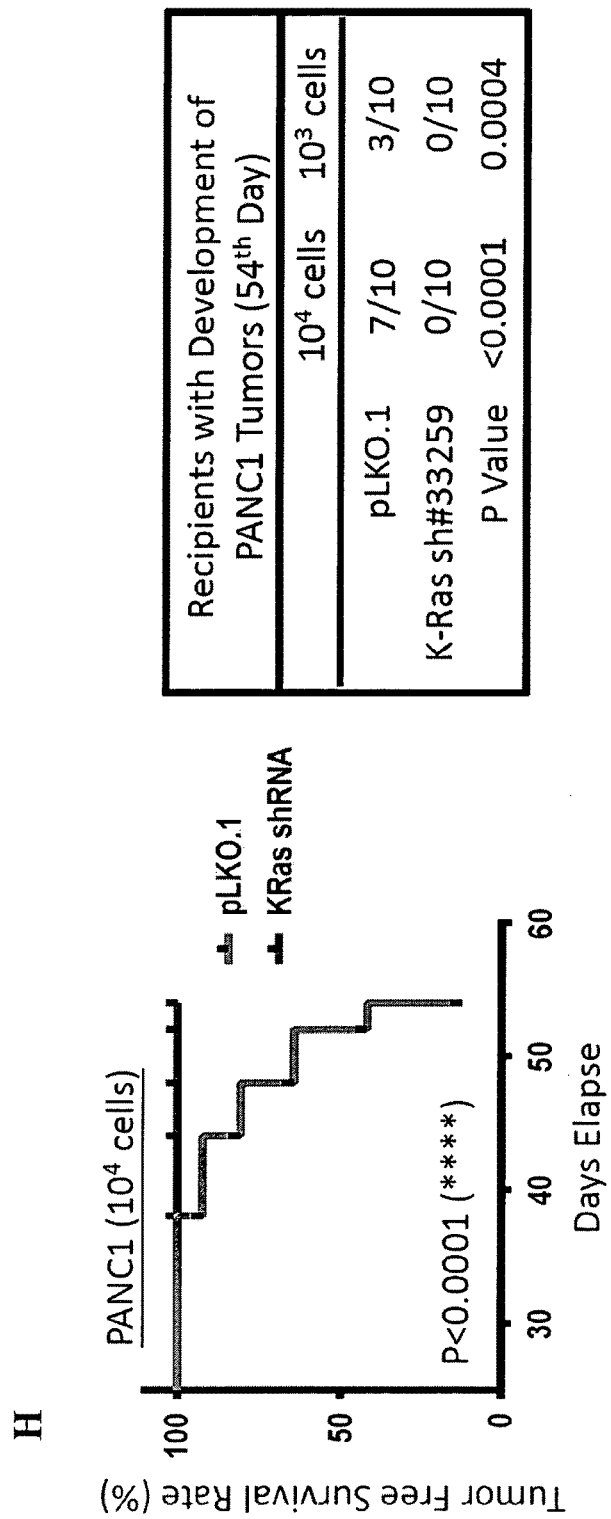

The present invention is based in part on the surprising discovery that although K-Ras and H-Ras share identical effectors and have similar properties, only oncogenic K-Ras, but not H-Ras, suppresses non-canonical Wnt/Ca$^{2+}$ signaling, an effect that contributes strongly to the tumorigenic properties of K-Ras. It has been discovered that K-Ras exerts its tumorigenic effect by binding to calmodulin, which reduces the activity of calmodulin-dependent kinase II and leads to a reduction in Fzd8 expression. It has further been shown that restoring Fzd8-mediated Wnt/Ca$^{2+}$ signaling using prostratin to promote dissociation of K-Ras to calmodulin suppresses tumor formation and growth. Accordingly, in one aspect the invention provides methods of treating a cancer, such as a cancer that expresses wild-type K-Ras or a cancer that expresses a mutated K-Ras, in a subject by administering a therapeutic amount of prostratin or a prostratin analog.

In another aspect, the invention also provides compositions and kits for treating a cancer, such as a K-Ras-expressing cancer, comprising prostratin or a prostratin analog.

II. Definitions

As used herein, the term "K-Ras" refers to "Kirsten rat sarcoma viral oncogene homolog." The protein encoded by the K-Ras gene is a small GTPase that functions in intracellular signal transduction. Human K-Ras gene and protein sequences are set forth in, e.g., Genbank Accession Nos. M54968.1 and AAB414942.1. Some common K-Ras genes and proteins found in human cancers contain mutations at codon 12, codon, codon 61, codon 146, and/or other concurrent sites. Non-limiting examples of K-Ras mutations include mutations at codon 5 (e.g., K5E), codon 9 (e.g., V9I), codon 12 (e.g., G12A, G12C, G12D, G12F, G12R, G12S, G12V, G12Y), codon 13 (e.g., G13C, G13D, G13V), codon 14 (e.g., V14I, V14L), codon 18 (e.g., A18D), codon 19 (e.g., L19F), codon 22 (e.g., Q22K), codon 23 (e.g., L23R), codon 24 (e.g., I24N), codon 26 (e.g., N26K), codon 33 (e.g., D33E), codon 36 (e.g., I36L, I36M), codon 57 (e.g., D57N), codon 59 (e.g., A59E, A59G, A59T), codon 61 (e.g., Q61H, Q61K, Q61L, Q61R), codon 62 (e.g., E62G, E62K), codon 63 (e.g., E63K), codon 64 (e.g., Y64D, Y64H, Y64N), codon 68 (e.g., R68S), codon 74 (e.g., T74P), codon 92 (e.g., D92Y), codon 97 (e.g., R97I), codon 110 (e.g., P110H, P110S), codon 117 (e.g., K117N), codon 118 (e.g., C118S), codon 119 (e.g., D119N), codon 135 (e.g., R135T), codon 138 (e.g., G138V), codon 140 (e.g., P140H), codon 146 (e.g., A146T, A146V), codon 147 (e.g., K147N), codon 153 (e.g., D153N), codon 156 (e.g., F156L), codon 160 (e.g., V160A), codon 164 (e.g., R164Q), codon 171 (e.g., I171M), codon 176 (e.g., K176Q), codon 185 (e.g., C185R, C185S), and codon 188 (e.g., M188V).

A "K-Ras-expressing cancer" refers to a cancer that has a detectable level of expression of K-Ras (either wild-type or its mutant forms). In some embodiments, a cancer has a detectable level of expression when at least 0.1% of cells in the cancer tissue sample are positive for K-Ras activation (e.g., wild-type K-Ras or a K-Ras activating mutation at codon 12, codon 13, codon 61, and/or other codons). In some embodiments, the cancer has a detectable level of expression of wild-type K-Ras. In some embodiments, the cancer has a detectable level of expression of a mutated K-Ras. In some embodiments, a K-Ras-expressing cancer has a level of expression of K-Ras (e.g., wild-type K-Ras or mutated K-Ras) that is at least 5%, 10%, 20%, 30%, 40%, 50%, 75%, 100%, 150%, or 200% greater than the level of K-Ras expression in a control (e.g., a non-diseased cell or tissue that does not express K-Ras, such as normal human peripheric lymphocytes).

The term "cancer" refers to a disease characterized by the uncontrolled growth of aberrant cells. The term includes all known cancers and neoplastic conditions, whether characterized as malignant, benign, soft tissue, or solid, and cancers of all stages and grades including pre- and postmetastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer, ovarian cancer; renal cancer; cancer of the central nervous system; skin cancer (e.g., melanoma); lymphomas; gliomas; choriocarcinomas; head and neck cancers; osteogenic sarcomas; and blood cancers. As used herein, a "tumor" comprises one or more cancerous cells. In some embodiments, the cancer is pancreatic cancer.

A "biological sample" includes blood and blood fractions or products (e.g., serum, plasma, platelets, red blood cells, and the like); sputum or saliva; kidney, lung, liver, heart, brain, nervous tissue, thyroid, eye, skeletal muscle, cartilage, or bone tissue; cultured cells, e.g., primary cultures, explants, and transformed cells, stem cells, stool, urine, etc. Such biological samples also include sections of tissues such as biopsy and autopsy samples, and frozen sections taken for histologic purposes. A biological sample is typically obtained from a "subject," i.e., a eukaryotic organism, most preferably a mammal such as a primate, e.g., chimpanzee or human; cow; dog; cat; a rodent, e.g., guinea pig, rat, or mouse; rabbit; or a bird; reptile; or fish.

A "therapeutic amount" or "therapeutically effective amount" of an agent (e.g., prostratin or a prostratin analog, or a salt or isomer thereof) is an amount of the agent which prevents, alleviates, abates, or reduces the severity of symptoms of a cancer (e.g., a K-Ras-expressing cancer) in a subject.

The term "prostratin," also referred to as 12-deoxyphorbol-13-acetate, refers to a compound having the following structure:

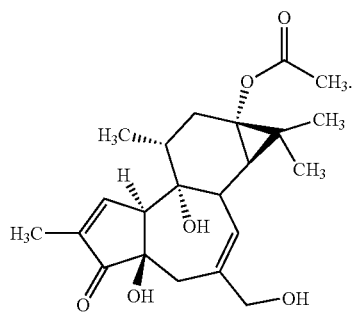

The term "prostratin analog" refers to a compound that is a structural derivative of prostratin, in which one or more atoms or functional groups is different from prostratin.

As used herein, the term "salt" refers to acid or base salts of a compound, e.g., prostratin or a prostratin analog. Illustrative examples of pharmaceutically acceptable salts are cationic salts such as alkali and alkaline earth metal (such as sodium, lithium, potassium, calcium, and magnesium) salts, ammonium (ammonium, trimethyl ammonium, diethylammonium, and tris-(hydroxymethyl)-methyl-ammonium) salts, mineral acid (hydrochloric acid, hydrobromic acid, phosphoric acid, and the like) salts, organic carboxylic acid (acetic acid, propionic acid, glutamic acid, citric acid, and the like) salts, organic sulfonic acid (methanesulfonic acid) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's, Pharmaceutical Sciences (current edition), Mack Publishing Co., Easton, Pa., which is incorporated herein by reference.

As used herein, the term "isomers" refers to compounds with the same chemical formula but which are structurally distinguishable.

The terms "administer," "administered," or "administering" refer to methods of delivering agents, compounds, or compositions to the desired site of biological action. These methods include, but are not limited to, topical delivery, parenteral delivery, intravenous delivery, intradermal delivery, intramuscular delivery, colonical delivery, rectal delivery, or intraperitoneal delivery. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

III. Methods of Treating Cancers

In one aspect, methods for treating or preventing a cancer in a subject are provided. In some embodiments, the method comprises administering to the subject a therapeutic amount of prostratin or a prostratin analog, or a salt or isomer thereof. In some embodiments, the subject is a human, e.g., a human adult or a human child.

In some embodiments, the cancer is a K-Ras-expressing cancer, e.g., a cancer that expresses or overexpresses wild-type K-Ras or a cancer that expresses a mutated form of K-Ras. In some embodiments, the K-Ras-expressing cancer is a pancreatic cancer, a colorectal cancer, or a lung cancer. In some embodiments, the K-Ras-expressing cancer is a pancreatic cancer, e.g., pancreatic ductal adenocarcinoma. In some embodiments, the method further comprises measuring the level of K-Ras expression in a sample (e.g., a tumor tissue sample) from the subject. In some embodiments, the method further comprises determining a K-Ras genotype that is expressed in a sample (e.g., a tumor tissue sample) from the subject.

In some embodiments, the method further comprises:
  detecting the level of K-Ras expression in a sample from the subject (e.g., a tumor cell or tumor tissue sample from the subject);
  determining whether the level of K-Ras expression in the sample from the subject is greater than the level of K-Ras expression of a control (e.g., a non-diseased cell or tissue that does not express K-Ras, such as normal human peripheric lymphocytes); and
  administering prostratin or a prostratin analog, or a salt or isomer thereof, to the subject when the level of K-Ras expression in the sample from the subject is greater than the level of K-Ras expression of a control.

In some embodiments, the cancer is not a K-Ras-expressing or -overexpressing cancer. As a non-limiting example, in some embodiments the cancer is a pancreatic cancer (e.g., a pancreatic ductal adenocarcinoma) that does not express or overexpress K-Ras.

K-Ras-Expressing Cancers

In some embodiments, the cancer is a cancer that expresses K-Ras at a detectable level. In some embodiments, a cancer has a detectable level of K-Ras expression when at least 0.1% of cells in the cancer tissue sample are positive for K-Ras activation (e.g., wild-type K-Ras or a K-Ras activating mutation at codon 12, codon 13, codon 61, and/or other codons). In some embodiments, the cancer has a detectable level of expression of wild-type K-Ras. In some embodiments, the cancer has a detectable level of expression of a mutated K-Ras. In some embodiments, the K-Ras mutation is an activating mutation at one or more of codon 5 (e.g., K5E), codon 9 (e.g., V9I), codon 12 (e.g., G12A, G12C, G12D, G12F, G12R, G12S, G12V, G12Y), codon 13 (e.g., G13C, G13D, G13V), codon 14 (e.g., V14I, V14L), codon 18 (e.g., A18D), codon 19 (e.g., L19F), codon 22 (e.g., Q22K), codon 23 (e.g., L23R), codon 24 (e.g., I24N), codon 26 (e.g., N26K), codon 33 (e.g., D33E), codon 36 (e.g., I36L, I36M), codon 57 (e.g., D57N), codon 59 (e.g., A59E, A59G, A59T), codon 61 (e.g., Q61H, Q61K, Q61L, Q61R), codon 62 (e.g., E62G, E62K), codon 63 (e.g., E63K), codon 64 (e.g., Y64D, Y64H, Y64N), codon 68 (e.g., R68S), codon 74 (e.g., T74P), codon 92 (e.g., D92Y), codon 97 (e.g., R97I), codon 110 (e.g., P110H, P110S), codon 117 (e.g., K117N), codon 118 (e.g., C118S), codon 119 (e.g., D119N), codon 135 (e.g., R135T), codon 138 (e.g., G138V), codon 140 (e.g., P140H), codon 146 (e.g., A146T, A146V), codon 147 (e.g., K147N), codon 153 (e.g., D153N), codon 156 (e.g., F156L), codon 160 (e.g., V160A), codon 164 (e.g., R164Q), codon 171 (e.g., I171M), codon 176 (e.g., K176Q), codon 185 (e.g., C185R, C185S), and codon 188 (e.g., M188V). In some embodiments, the K-Ras mutation is a mutation at amino acid residue G12 (e.g., a G12C, G12V, G12D, G12A, G12S, G12R, or G12F substitution). In some embodiments, the K-Ras mutation is a mutation at amino acid residue G13 (e.g., a G13C or G13D substitution). In some embodiments, the K-Ras mutation is a mutation at amino acid residue Q61 (e.g., a Q61H or Q61K substitution). In some embodiments, the K-Ras mutation is a mutation at amino acid residue A146 (e.g., an A146T or A146V substitution). In some embodiments, the cancer that expresses wild-type or mutated K-Ras at a detectable level is a pancreatic cancer, a lung cancer, or a colorectal cancer.

In some embodiments, the cancer is a cancer that overexpresses K-Ras. As used herein a cancer "overexpresses" K-Ras if the level of expression of K-Ras (e.g., wild-type K-Ras or mutated K-Ras) is increased relative to a threshold value or a control sample (e.g., a non-diseased cell or tissue that does not express K-Ras, such as normal human peripheric lymphocytes, or a cancer sample from a subject known to be negative for expression of K-Ras). In some embodiments, a cancer overexpresses K-Ras if the level of expression of K-Ras (e.g., wild-type K-Ras or mutated K-Ras) is at least 10%, 20%, 30%, 40%, 50%, 75%, 100%, 150%, or 200% greater than a threshold value or the level of K-Ras expression in a control sample (e.g., a cancer known to be negative for expression of K-Ras). In some embodiments, a cancer overexpresses K-Ras if the level of expression of K-Ras (e.g., wild-type K-Ras or mutated K-Ras) is at least 2-fold, 3-fold, 4-fold, 5-fold, 6-fold, 7-fold, 8-fold, 9-fold, or more relative to a threshold value or to the level of K-Ras expression in a control sample (e.g., a cancer known to be negative for expression of K-Ras). In some embodiments, the cancer that overexpresses wild-type or mutated K-Ras is a pancreatic cancer, a lung cancer, or a colorectal cancer.

The level of expression of K-Ras in a cancer can be measured according to methods known in the art. In some embodiments, the level of K-Ras gene expression in a cancer is measured. In some embodiments, the level of K-Ras protein expression in a cancer is measured. The level of K-Ras gene or protein expression, or the detection of a K-Ras genotype, can be measured in a biological sample from a subject. In some embodiments, the biological sample comprises a cancer cell (e.g., a cell obtained or derived from a tumor). In some embodiments, the biological sample is a tumor tissue sample.

The level of K-Ras protein expression can be measured using any of a number of immunoassays known in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Specific immunological binding of an antibody to a protein (e.g., K-Ras) can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Analysis of K-Ras nucleic acid expression levels or K-Ras genotype can be achieved using routine techniques such as Southern analysis, reverse-transcriptase polymerase chain reaction (RT-PCR), or any other methods based on hybridization to a nucleic acid sequence that is complementary to a portion of the coding sequence of interest (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid expression levels or genotype can also be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nat. Biotechnol.,* 16:381-384 (1998)), pyrosequencing (Ronaghi et al., *Science,* 281:363-365 (1998)), and sequencing by hybridization. Chee et al., *Science,* 274:610-614 (1996); Drmanac et al., *Science,* 260:1649-1652 (1993); Drmanac et al., *Nat. Biotechnol.,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis. In some embodiments, methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE), and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

The analysis can be carried out in a variety of physical formats. For example, the use of microtiter plates or automation could be used to facilitate the processing of large numbers of test samples.

Alternatively, for detecting the level of protein or nucleic acid expression, antibody or nucleic acid probes can be applied to subject samples immobilized on microscope slides. The resulting antibody staining or in situ hybridization pattern can be visualized using any one of a variety of light or fluorescent microscopic methods known in the art.

Analysis of the protein or nucleic acid can also be achieved, for example, by high pressure liquid chromatography (HPLC), alone or in combination with mass spectrometry (e.g., MALDI/MS, MALDI-TOF/MS, tandem MS, etc.).

Methods of determining K-Ras genotype are described in the art. See, e.g., Kramer et al., *Cell Oncol.* 31:161-167 (2009); Chen et al., *J. Chromatogr. A* 1216:5147-5154 (2009); Lamy et al., *Modern Pathology* 24:1090-1100 (2011); Galbiati et al., *PLoS ONE* 8(3):359939 (2013); and WO 2010/048691.

Prostratin and Prostratin Analogs

In some embodiments, a therapeutic amount of prostratin, or a salt or isomer thereof, is administered to a subject in need thereof (e.g., a subject having a cancer, e.g., a K-Ras-expressing or -overexpressing cancer). Prostratin (12-deoxyphorbol-13-acetate; CAS 60857-08-1) is commercially available from, for example, Santa Cruz Biotechnology (Dallas, Tex.) and abcam Biochemicals (Cambridge, Mass.).

In some embodiments, a therapeutic amount of a prostratin analog, or a salt or isomer thereof, is administered to a subject in need thereof (e.g., a subject having a cancer, e.g., a K-Ras-expressing or overexpressing cancer). In some embodiments, the prostratin analog is a structurally related compound to prostratin that has a comparable protein kinase C (PKC) binding affinity as prostratin. In some embodiments, the prostratin analog is a structurally related compound to prostratin that has an improved PKC binding affinity relative to prostratin.

In some embodiments, the prostratin analog is a compound disclosed in U.S. Pat. Nos. 5,021,549, 8,536,378, WO 2009/126949, US 2011/0014699, or US 2011/0224297, each of which is incorporated by reference herein.

In some embodiments, a structural analog of prostratin may share one or more structural characteristics with the parent prostratin compound, but may differ in which ester group is selected. In some embodiments, the prostratin analog is a compound having the structural formula:

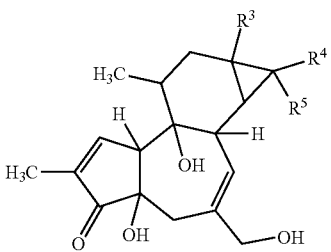

wherein:

$R^3$ is selected from the group consisting of OR, halo, SeR, SR, SOR, $SO_2R$, aryl, NHR, $NR_2$, and NHCOR, where R is a lower alkyl of 1-15 carbons (C1 to C15);

$R^4$ is selected from the group consisting of hydrogen, alkyl (C1 to C20), cyclic alkyl (C3 to C15), aryl (C6 to C10), hydroxyl, alkyl carbonate, carbamate, ester, ether, thiol, amine, phosphine, phosphate, phosphoramide, phosphoramidite, phosphoramidate, phosphite, phosphonate, sulfate, sulfonate, sulfonamide, sulfone, sulfite, amide, guanidine, and urea; and $R^5$ is selected from the group consisting of hydrogen, alkyl (C1 to C20), cyclic alkyl (C3 to C15), aryl (C6 to C10), hydroxyl, alkyl carbonate, carbamate, ester, ether, thiol, amine, phosphine, phosphate, phosphoramide, phosphoramidite, phosphoramidate, phosphite, phosphonate, sulfate, sulfonate, sulfonamide, sulfone, sulfite, amide, guanidine, and urea.

In some embodiments, the prostratin analog is a compound having the structural formula:

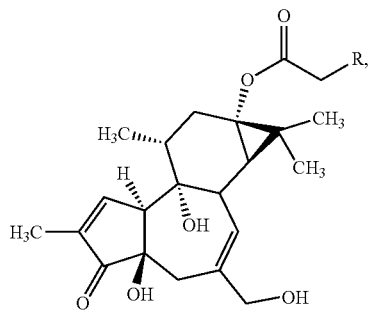

wherein R is ethyl, formate, propionate, butyrate, pentanoate, hexanoate, benzoate, phenyl acetate, cyclohexyl acetate, pentafluorophenyl acetate, 1-Naphthyl acetate, 2-Naphthyl acetate, (5,6,7,8)Tetrahydro-1-naphthyl acetate, biphenyl acetate, adamantyl acetate, or p-Benzyl phenyl acetate.

Methods of synthesizing prostratin and prostratin analogs are described in the art. See, e.g., Wender et al., *Science* 320:649-652 (2008); and Beans et al., *Proc. Natl. Acad. Sci USA* 110:11698-11703 (2013), each of which is incorporated by reference. Methods of testing the activity of prostratin and prostratin analogs, for example by PKC binding affinity assay, are also described in the art. See, e.g., Beans et al., *Proc. Natl. Acad. Sci USA* 110:11698-11703 (2013).

Administration and Combination Therapy

The route of administration of a therapeutic agent (e.g., prostratin or a prostratin analog, or a salt or isomer thereof) can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art. In some embodiments, the prostratin or the prostratin analog, or salt or isomer thereof, is administered orally, intravenously, or intraperitoneally.

In some embodiments, the prostratin or the prostratin analog, or a salt or isomer thereof, is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

In some embodiments, prostratin or a prostratin analog, or a salt or isomer thereof, is administered in combination with a second therapeutic agent. In some embodiments, the second therapeutic agent is a chemotherapeutic agent. In some embodiments, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel). In some embodiments, the chemotherapeutic agent is gemcitabine.

Co-administered therapeutic agents (e.g., prostratin or a prostratin analog, or a salt or isomer thereof, and a second therapeutic agent as described herein) can be administered together or separately, simultaneously or at different times. When administered, the therapeutic agents independently can be administered once, twice, three, four times daily or more or less often, as needed. In some embodiments, the administered therapeutic agents are administered once daily. In some embodiments, the administered therapeutic agents are administered at the same time or times, for instance as an admixture. In some embodiments, one or more of the therapeutic agents is administered in a sustained-release formulation.

In some embodiments, prostratin or a prostratin analog, or a salt or isomer thereof, and a second therapeutic agent are administered concurrently. In some embodiments, prostratin or a prostratin analog is administered first, for example for about 1, 2, 3, 4, 5, 6, 7, 8, 9, 10, 15, 20, 25, 30, 40, 50, 60, 70, 80, 90, 100 days or more prior to administering the second therapeutic agent (e.g., chemotherapeutic agent). In some embodiments, the second therapeutic agent (e.g., chemotherapeutic agent) is administered first, for example for about 1, 2, 3, 4, 5, 6, 7, 8, 9, 10, 15, 20, 25, 30, 40, 50, 60, 70, 80, 90, 100 days or more prior to administering the prostratin or prostratin analog.

In some embodiments, prostratin or a prostratin analog, or a salt or isomer thereof (and optionally a second therapeutic agent, e.g., a chemotherapeutic agent as described herein) is administered to the subject over an extended period of time, e.g., for at least 30, 40, 50, 60, 70, 80, 90, 100, 150, 200, 250, 300, 350 day or longer.

IV. Compositions and Kits

In another aspect, compositions and kits for use in treating or preventing a cancer (e.g., a K-Ras-expressing or -overexpressing cancer) in a subject are provided.

In some embodiments, pharmaceutical compositions comprising prostratin or a prostratin analog, or a salt or isomer thereof, for use in administering to a subject having a cancer (e.g., a cancer in which wild-type K-Ras or mutated K-Ras is expressed or overexpressed) are provided. In some embodiments, the prostratin or prostratin analog (or salt or isomer thereof) is as described in Section III above. In some embodiments, a combination of prostratin or a prostratin analog, or a salt or isomer thereof, and a second therapeutic agent (e.g., a chemotherapeutic agent as described herein) are formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Guidance for preparing formulations for use in the present invention is found in, for example, in *Remington: The Science and Practice of Pharmacy*, 21$^{st}$ Ed., 2006, supra; *Martindale: The Complete Drug Reference*, Sweetman, 2005, London: Pharmaceutical Press; Niazi, *Handbook of Pharmaceutical Manufacturing Formulations*, 2004, CRC Press; and Gibson, *Pharmaceutical Preformulation and Formulation: A Practical Guide from Candidate Drug Selection to Commercial Dosage Form*, 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In some embodiments, prostratin or a prostratin analog, or a salt or isomer thereof (and optionally a second therapeutic agent, e.g., a chemotherapeutic agent as described herein) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more.

Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplary extended release formulations include those described in U.S. Pat. Nos. 6,635,680; 6,624,200; 6,613,361; 6,613,358; 6,596,308; 6,589,563; 6,562,375; 6,548,084; 6,541,020; 6,537,579; 6,528,080 and 6,524,621, each of which is hereby incorporated herein by reference. Exemplary controlled release formulations include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, prostratin or a prostratin analog, or a salt or isomer thereof (and optionally a second therapeutic agent, e.g., a chemotherapeutic agent as described herein) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

The prostratin or a prostratin analog, or a salt or isomer thereof (and optionally a second therapeutic agent, e.g., a chemotherapeutic agent as described herein) can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

The prostratin or a prostratin analog or a salt or isomer thereof (and optionally a second therapeutic agent, e.g., a chemotherapeutic agent as described herein) can be administered systemically by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplary transdermal delivery formulations include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

In some embodiments, a pharmaceutical composition comprises an acceptable carrier and/or excipients. A pharmaceutically acceptable carrier includes any solvents, dispersion media, or coatings that are physiologically compatible and that preferably does not interfere with or otherwise inhibit the activity of the therapeutic agent. In some embodiments, the carrier is suitable for intravenous, intramuscular, oral, intraperitoneal, transdermal, topical, or subcutaneous administration. Pharmaceutically acceptable carriers can contain one or more physiologically acceptable compound (s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, 21st Edition, Philadelphia, Pa. Lippincott Williams & Wilkins, 2005. Various pharmaceutically acceptable excipients are well-known in the art and can be found in, for example, Handbook of Pharmaceutical Excipients (5$^{th}$ ed., Ed. Rowe et al., Pharmaceutical Press, Washington, D.C.).

In some embodiments, kits for use in administering to a subject having a cancer (e.g., a cancer in which wild-type K-Ras or mutated K-Ras is expressed or overexpressed) are provided. In some embodiments, the kit comprises:

prostratin or a prostratin analog, or a salt or isomer thereof; and a second therapeutic agent.

In some embodiments, the prostratin or prostratin analog (or salt or isomer thereof) is as described in Section III above. In some embodiments, the second therapeutic agent is a chemotherapeutic agent. In some embodiments, the chemotherapeutic agent is an alkylating agent, an anthracycline, a cytoskeletal disruptor, a histone deacetylase inhibitor, an inhibitor of topoisomerase, a kinase inhibitor, a nucleoside analog or precursor analog, a peptide antibiotic, a platinum-based agent, or a plant alkaloid. In some embodiments, the chemotherapeutic agent is a nucleoside analog. In some embodiments, the chemotherapeutic agent is gemcitabine.

In some embodiments, the kits can further comprise instructional materials containing directions (i.e., protocols) for the practice of the methods of this invention (e.g., instructions for using the kit for treating a cancer). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

V. Examples

The following examples are offered to illustrate, but not to limit, the claimed invention.

Example 1

K-Ras Promotes Tumorigenicity Through Suppression of Non-Canonical Wnt Signaling Introduction Small GTPases of the Ras superfamily are critical components of multiple signaling pathways. The three canonical members in the Ras subfamily, H-Ras, N-Ras and K-Ras, are frequently mutated in human tumors and disturb a multitude of cellular process, such as gene expressions, cell cycle progression and evasion of apoptosis (Giehl, *Biol Chem* 386:193-205, 2005). Extensive studies in the past three decades have established Ras proteins as drivers of malignant transformation, tumor initiation as well as tumor progression and metastasis, suggesting that oncogenic Ras is a highly attractive therapeutic target (Stephen et al., *Cancer Cell* 25:272-281, 2014). An unresolved question is whether H-Ras, N-Ras and K-Ras proteins play unique or redundant roles in physiological and pathological processes. Due to their high degree of sequence homology, as well as overlapping upstream activators and downstream effectors, these three Ras isoforms have long been considered functionally redundant. However, increasing evidence suggests that these Ras isoforms may also have distinct biological properties. First, genetic ablation of each of the three Ras loci leads to dramatically different phenotypes in transgenic animals. K-Ras4B deficiency results in embryonic lethality, whereas N-Ras, H-Ras, and K-Ras4A knock-out mice exhibit no apparent abnormalities (Johnson et al., *Genes Dev.* 11:2468-2481, 1997; Koera et al., *Oncogene* 15:1151-1159, 1997; Malumbres and Barbacid, *Nat Rev Cancer* 3:459-465, 2003). However, it remains to be determined whether this unique biological phenotype of K-Ras is caused by specific function(s) of its gene product or by its distinct expression pattern (Esteban et al., *Mol. Cell Biol* 21:1444-1452, 2001). Secondly, activating mutations in H-Ras, N-Ras or K-Ras have been found in 20% to 30% of all human tumors, but display a striking degree of tissue-specificity. N-Ras mutations are frequent in acute leukemias, where H-Ras and K-Ras mutations are rare (Sakamoto et al., *Hum Pathol* 32:1225-1231, 2001). Conversely, oncogenic K-Ras mutations occur at high frequency in pancreatic (90%), colorectal (50%), and lung (35%) carcinomas, while N-Ras and H-Ras mutations are extremely uncommon (Prior et al., *Cancer Res.* 72:2457-2467, 2012).

Given that K-Ras4B, but not N-Ras, H-Ras or K-Ras4A, is essential for embryonic development, it is possible that K-Ras4B plays a vital and unique role in embryonic stem cells (ESCs). In fact, several embryonic genes and signaling pathways, such as Myc, Notch signaling and Wnt signaling, have been shown to have overlapping regulatory roles in both normal ESCs and the tumor initiations of cancer cells (Harris et al., *Expert Opin Ther Targets* 16:131-145, 2012). Hence, it is an intriguing possibility that oncogenic K-Ras plays a crucial but previously unknown role in inducing tumor-initiating, stem-cell like characteristics, and that these characteristics contribute to the aggressive nature of K-RAS-mutant tumors.

Of the Ras proteins, K-Ras is the most frequently mutated and, therefore, is an attractive target for cancer therapy, especially in pancreatic cancers for which no effective therapies exist. However, despite the tremendous interests in K-Ras as a therapeutic target, there has been no successes in developing small molecule inhibitors that directly block K-Ras function and show efficacy in pre-clinical models (Downward, *Nat Rev Cancer* 3:11-22, 2003; Kamoub and Weinberg, *Nat Rev Mol Cell Biol* 9:517-531, 2008; Stephen et al., 2014). In this study, we provide evidence that oncogenic K-Ras elicits a tumorigenic phenotype through downregulation of non-canonical Wnt/$Ca^{2+}$ signaling and repression of Fzd8 expression. This was not observed in H-Ras-transformed cells, thereby establishing a bona fide isoform-specific role for K-Ras. Binding of calmodulin (CaM) to K-Ras (the 4B isoform, specifically), but not to H-Ras, appears to be responsible for this major difference: CaM binding to K-Ras reduces the activity of CaM-dependent kinsae II (CaMKii), a major downstream effector of the Wnt/$Ca^{2+}$ signaling pathway, and leads to reduction in Fzd8 expression. Restoration of Fzd8-mediated Wnt/$Ca^{2+}$ signaling by increased Fzd8 expression, or be preventing K-Ras binding to CaM impaired K-Ras-mediated tumorigenicity, providing a potential novel avenue to inhibit this "undruggable" protein. Indeed, treatment of mice with prostratin, a natural product that promotes dissociation of K-Ras from CaM, suppressed tumor formation and growth in pancreas cancer models and papillomas driven specifically by K-Ras$^{G12V}$, but not those driven by H-Ras$^{G12V}$.

Figure 8:
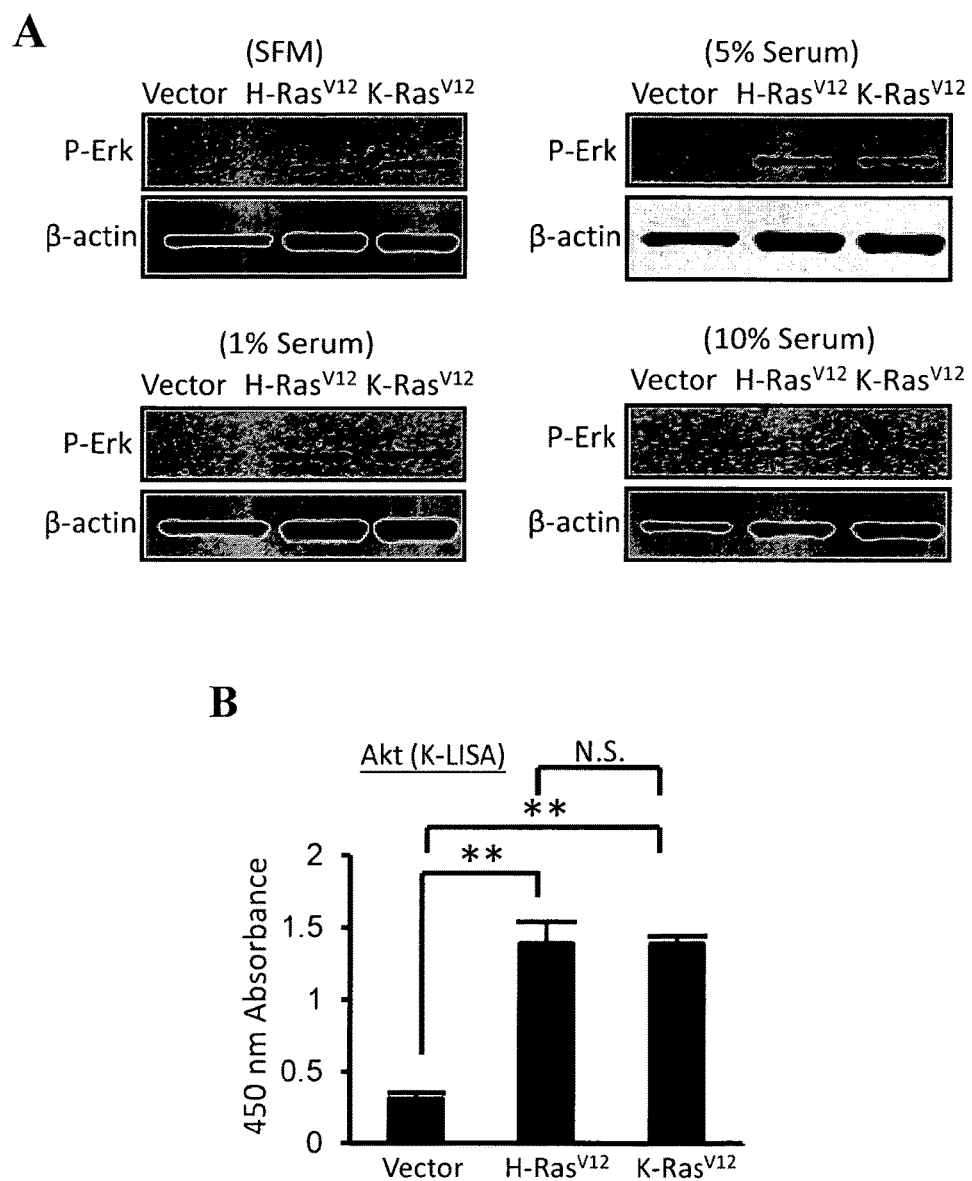
FIG. 8. (A) Similar level of phosphor-Erk in NIH/3T3 cells transformed by H-Ras$^{V12}$ or K-Ras$^{V12}$ despite the serum concentration in culture medium. (B) Similar Akt activity in cells transformed by H-Ras$^{V12}$ or K-Ras$^{V12}$ as measured by K-LISA (N=4). (C) Increased re-plating efficiency of spheres formed by K-Ras$^{V12}$-transformed NIH/3T3 cells. Left panel: morphology of spheres and its subsequent changes after placing in serum containing media. Middle panel: crystal violet staining of viable cells. Right panel: re-plating efficiency (N=8). (D) Signaling potency of EGF in BxPC3 cells with wild type Ras proteins as indicated by Erk phosphorylation. (E-F) Selective knockdown of H-Ras or K-Ras in BxPC3 cells by shRNAs. (G) Morphology of PANC2.13 (left) and PANC1 (right) cells after K-Ras had been knocked down. (H-I) Knockdown of K-Ras reduced stemness signatures at protein (H) or mRNA (I) levels in PANC2.13 or PANC1 cells. (J) Knockdown of mutant K-Ras reduced the formation and re-plating of spheres in PANC2.13 cells (N=6). * $P<0.05$;  $P<0.01$; * $P<0.001$.
Figure 8:
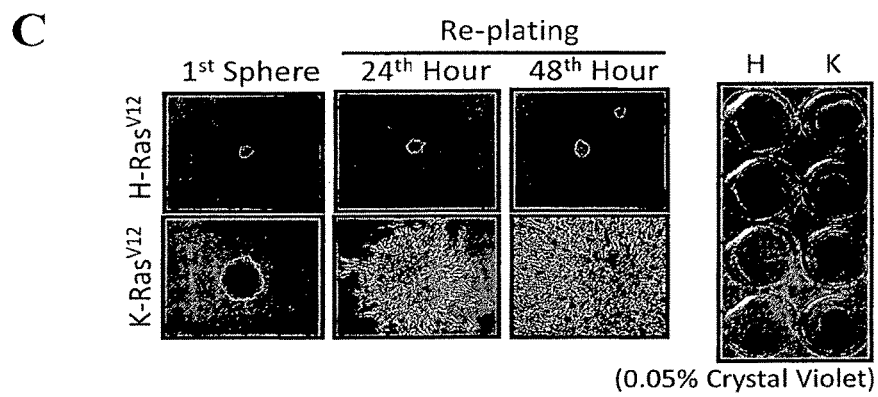
Figure 8:
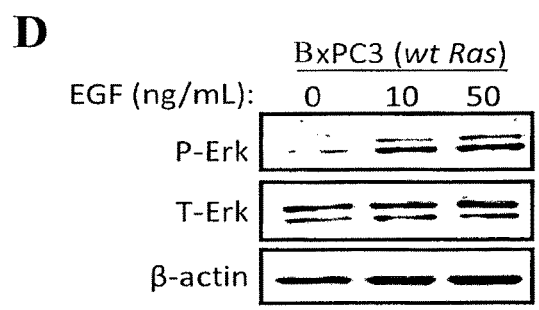
Figure 8:
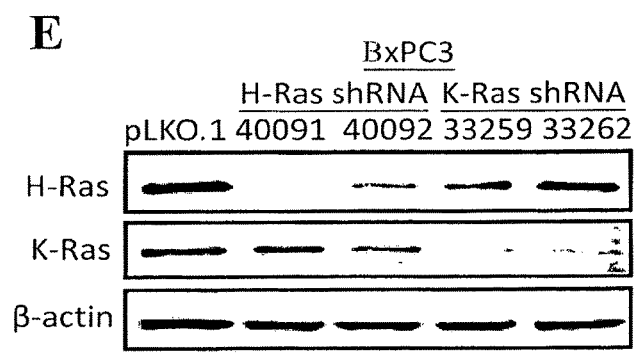
Figure 8:
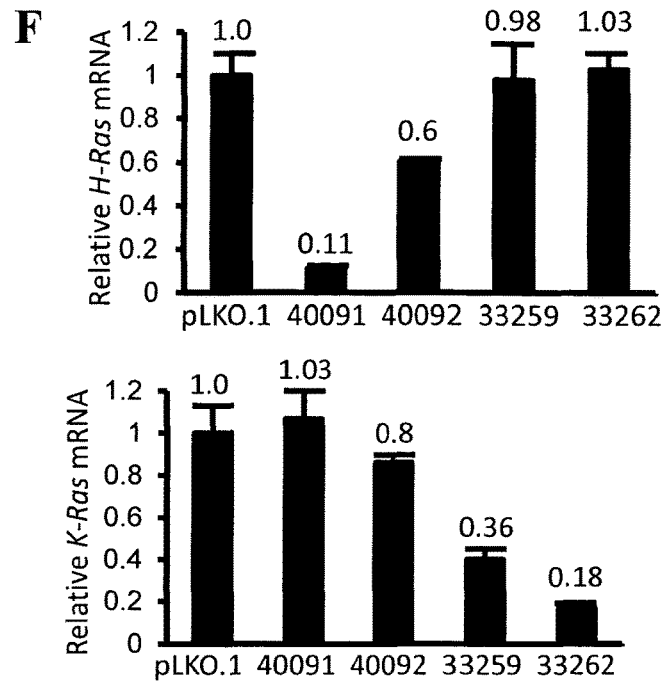
Figure 8:
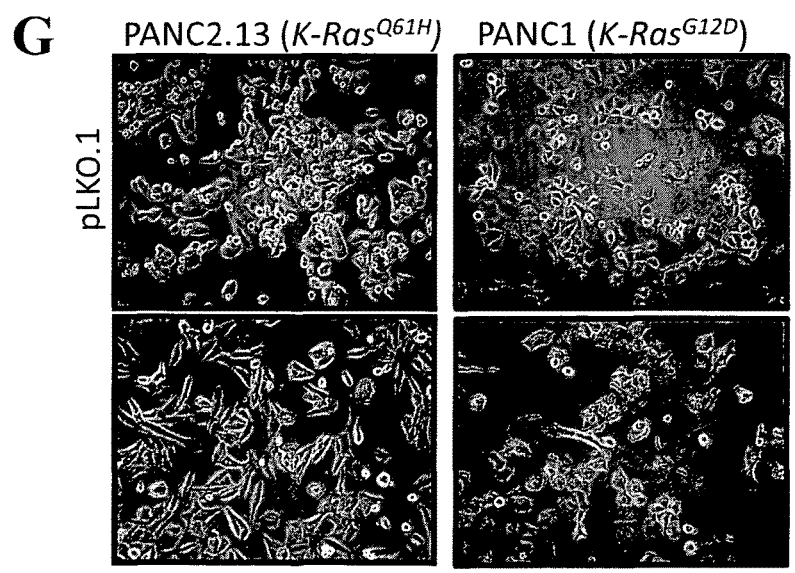
Figure 8:
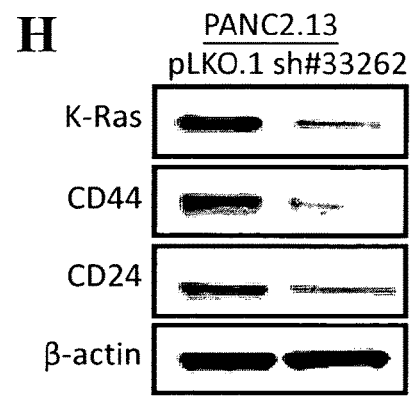
Figure 8:
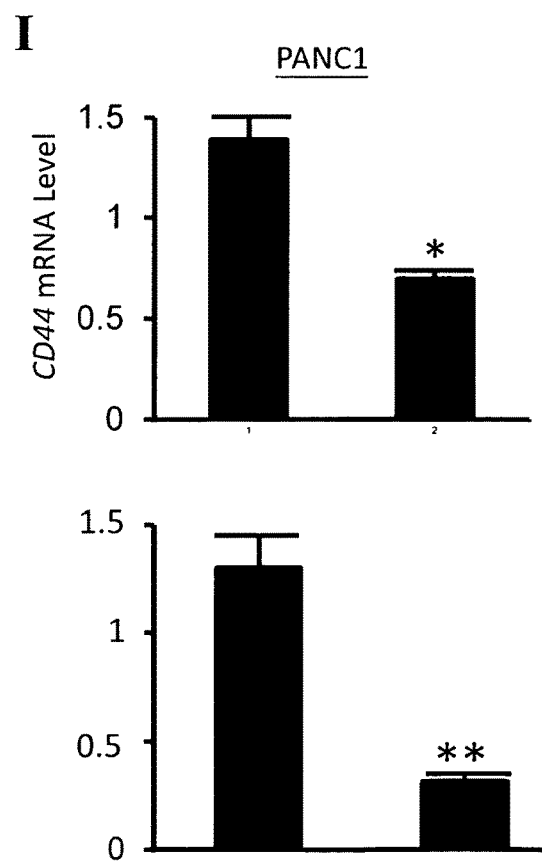
Figure 8:
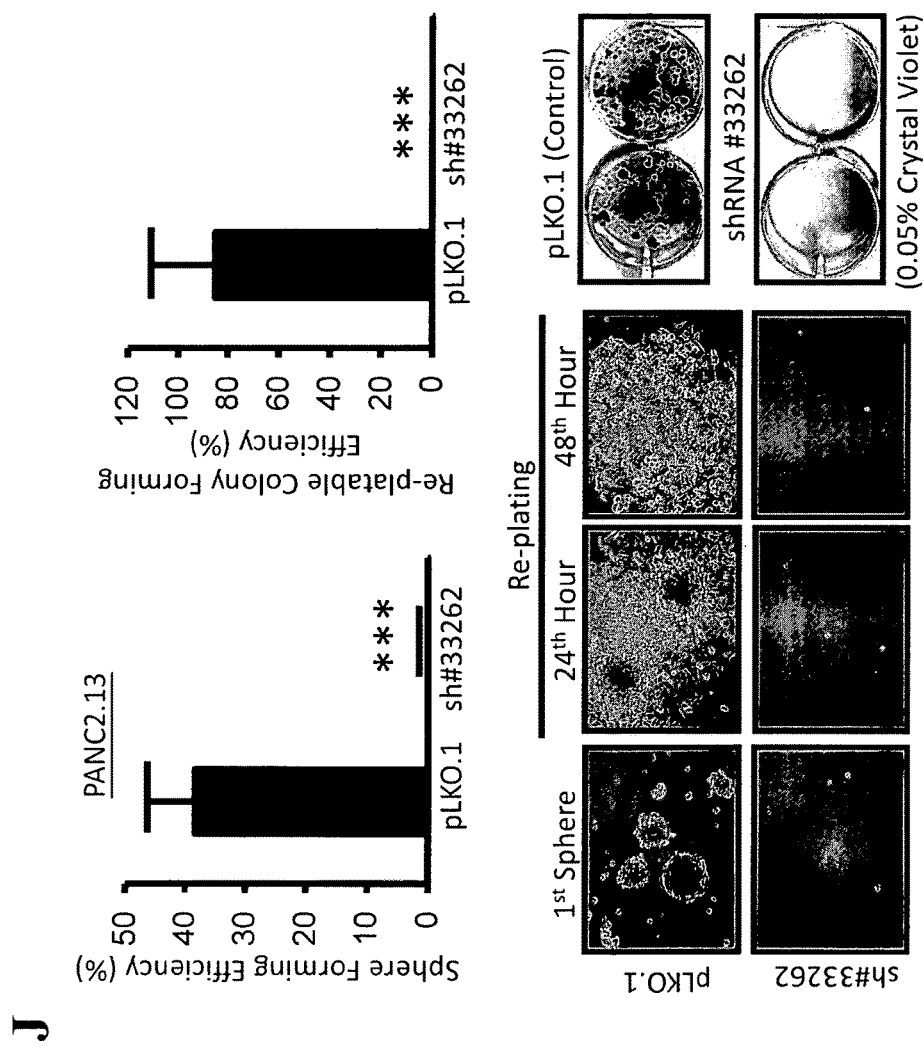

K-Ras$^{v12}$ and H-Ras$^{v12}$ Differ in Initiating Tumor Formation Despite Comparable Canonical MAPK and Akt Signaling To elucidate distinct properties of K-Ras and H-Ras, we expressed oncogenic H-Ras and K-Ras under the control of the cytomegalovirus promoter in isogenic NIH/3T3 cells and looked for phenotypic differences between cells with these two oncogenes. Both H- and K-Ras$^{V12}$-transformed NIH/3T3 cells showed similar morphological changes, indicative of transformation (data not shown). GTP-bound Ras binds to and activates numerous downstream effectors, and levels of Ras-GTP can be measured by co-immuno-precipitation of Ras-GTP with the Ras-binding domain (RBD) of C-Raf or RalGDS (Santarpia et al., *Expert Opin Ther Targets* 16:103-119, 2012). H-Ras$^{V12}$ and K-Ras$^{V12}$ transformed cells had comparable levels of GTP-loaded Ras, as revealed by C-Raf-RBD- and RalGDS-RBD-pull down assays (FIG. 1A), and exhibited similar levels of phosphorylated Erk1/2 and Akt (FIG. 1B), regardless of the presence of serum in the culturing condition (FIG. 1B; FIG. 8A). Furthermore, an ELISA-based assay utilizing a biotinylated peptide substrate of Akt confirmed that H-Ras$^{V12}$- and K-Ras$^{V12}$-transformed NIH/3T3 cells had similar Akt kinase activities, both of which were elevated when compared to vector control cells (FIG. 8B). Collectively, these data suggest that the Ras$^{V12}$-transformed cells contain similar levels of active H-Ras and K-Ras, as well as comparable levels of activation of canonical downstream signaling pathways.

Next we examined whether Ras$^{V12}$-transformed cells exhibited stem cell-like qualities and the ability to self-renew at the single cell level in vitro. One measure of stem-ness or self-renewal in vitro is sphere formation and the subsequent ability of spheres to recapitulate the exponential growth of cells in 2D cultures (Fang et al., *Cancer Res* 65:9328-9337, 2005; Fujii et al., *Int J Oncol* 34:1381-1386, 2009; Gou et al., *Pancreas* 34:429 -435, 2007; Ponti et al, *Cancer Res.* 65:5506-5511, 2005; Singh et al., *Cancer Res.* 63:5821-5828, 2003). With limited numbers of seeded cells, K-Ras$^{V12}$-transformed NIH/3T3 cells showed significantly increased sphere forming efficiency when compared with H-Ras$^{V12}$-transformed and vector controls (FIG. 1C). Re-plating revealed that spheres from K-Ras$^{V12}$-transformed NIH/3T3 cells were viable and able to re-initiate exponentially growing cells in 2D culture, in contrast to the reduced viability and re-plating efficiency of spheres from H-Ras$^{V12}$-transformed cells (FIG. 8C). The increased sphere forming efficiency of K-Ras$^{V12}$-transformed NIH/3T3 cells was not due to higher proliferation rates, since H-Ras$^{V12}$-transformed cells actually had higher rates of DNA synthesis than K-Ras transformed cells when seeded at low density (data not shown).

We next evaluated the tumorigenic potential of K-Ras$^{V12}$-transformed NIH/3T3 cells, using limited and serial transplantation in vivo (Clarke et al., *Cancer Res.* 66:9339-9344, 2006). Mice were subcutaneously injected with H-Ras$^{V12}$ or K-Ras$^{V12}$ transformed -NIH/3T3 cells and tumor free survival was determined. When 1,000 cells were engrafted, H- and K-Ras$^{V12}$ tumors arose at similar rates. However, when the number of engrafted cells was reduced to 100, K-Ras$^{V12}$-transformed cells displayed significantly enhanced tumor initiating rates when compared with H-Ras$^{V12}$ cells (FIG. 1D, left panel). To further examine their renewal ability in vivo, we re-transplanted the cells isolated from primary tumors (initiated by 1,000 engrafted cells) into a second cohort of recipient mice. Upon injection of 500 NIH/3T3-K-Ras$^{V12}$ cells, all 10 injections gave rise to tumors. In contrast, only 2 out of 10 injections of H-Ras$^{V12}$ cells successfully initiated tumors (FIG. 1D, right panel). K-Ras$^{V12}$-transformed NIH/3T3 cells therefore exhibited increased tumor-initiating frequency and elevated ability to recapitulate tumor formation in vivo when compared to H-Ras$^{V12}$-transformed cells.

Activating mutations in different Ras isoforms occurs in human cancers in a highly tissue-specific manner (Hezel et al., *Genes Dev.* 20:1218-1249, 2006), but it is not clear whether these differences reflect distinct properties of each isoform. To examine whether K-Ras and H-Ras play distinct roles in inducing tumorigenicity, we examined the roles of H-Ras and K-Ras in BxPC3 cells, a pancreatic cancer cell line expressing wild-type H- and K-Ras, in regulating malignancy. Stimulation of BxPC3 cell with EGF activated MAPK signaling pathway and significantly increased sphere-forming efficiency (FIG. 1E and FIG. 8D). Knockdown of K-Ras, not H-Ras, significantly reduced EGF-stimulated sphere forming efficiency and reduced the size of initiated spheres, supporting the ideas that K-Ras has unique properties that may contribute to malignancy in human pancreatic cancer cells (FIG. 1F and FIG. 8E-F).

Figure 9:
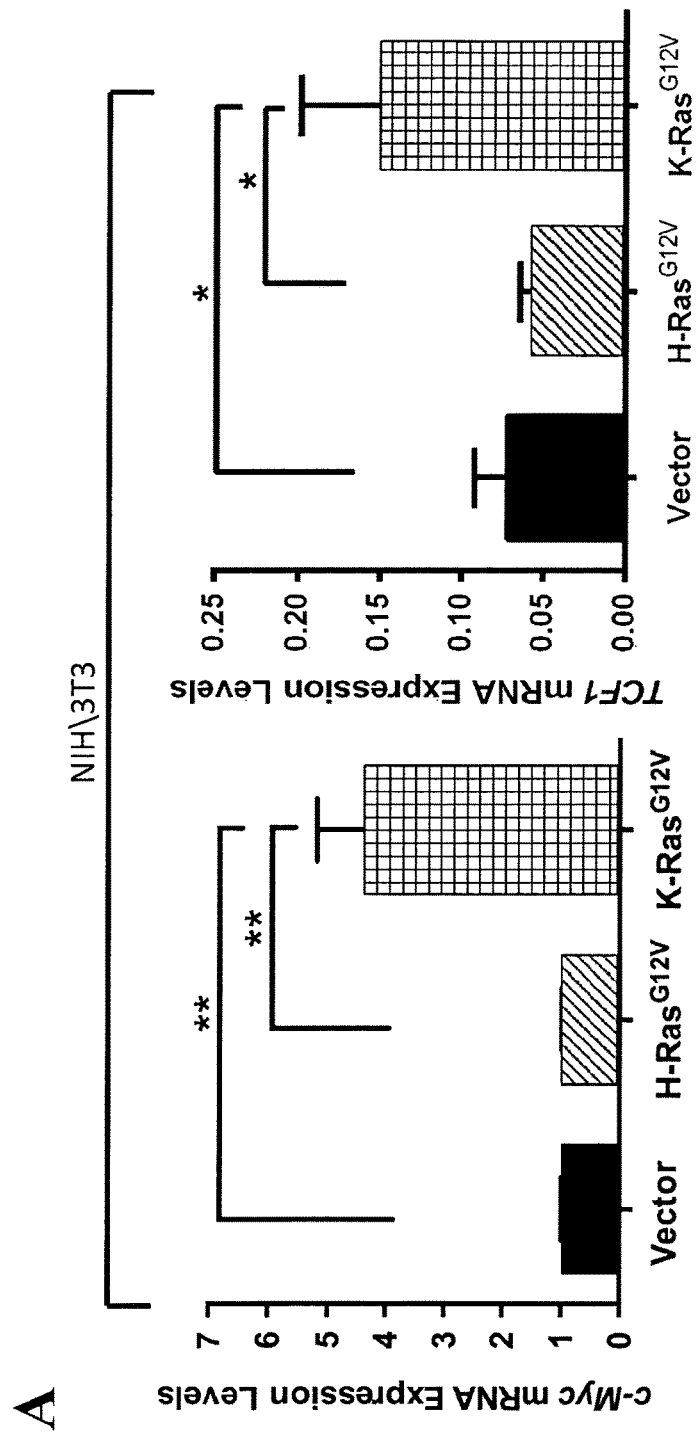
FIG. 9. (A) Increased c-Myc and TCF1 expressions at mRNA level in NIH/3T3 cells transformed with K-Ras$^{V12}$ when compared to vector control and H-Ras$^{V12}$ (N=3). (B) Repressed Fzd8-mediated non-canonical signaling pathway in Rasless MEF-K-Ras$^{G12V}$ cells. (Left panel) Western blot showed decreased phosph-CaMKii in Rasless MEFs expressing K-Ras$^{G12V}$. (Right panel) qPCR arrays of mouse Fzd8 in H-Ras$^{G12V}$ and K-Ras$^{G12V}$-expressing Rasless MEFs (N=3). (C) Rasless MEF K-Ras$^{G12V}$ cells showed higher tumor initiation frequency than Rasless MEF H-Ras$^{G12V}$ cells in the same number of injected cells. (D) Tumors derived from Rasless MEF K-Ras$^{G12V}$ cells showed dramatically increased proliferation rate. Data are means±SEM. (E) NIH/3T3 transformed by H- and K-Ras$^{V12}$ showed similar levels of Wnt3a and Wnt5a expressions. (F) Western blot probed for phosphor-CaMKii in NIH/3T3 cells cultured in serum free medium with or without the presence of Wnt3a or Wnt5a. (G) TOPFlash assays in NIH/3T3 cells with or without the presence of Wnt3a or Wnt5a in the culture medium (N=4). (H) Sphere formation assay in NIH/3T3 cells in response to Wnt3a or Wnt5a.  $P<0.01$; * $P<0.001$; **** $P<0.0001$.
Figure 9:
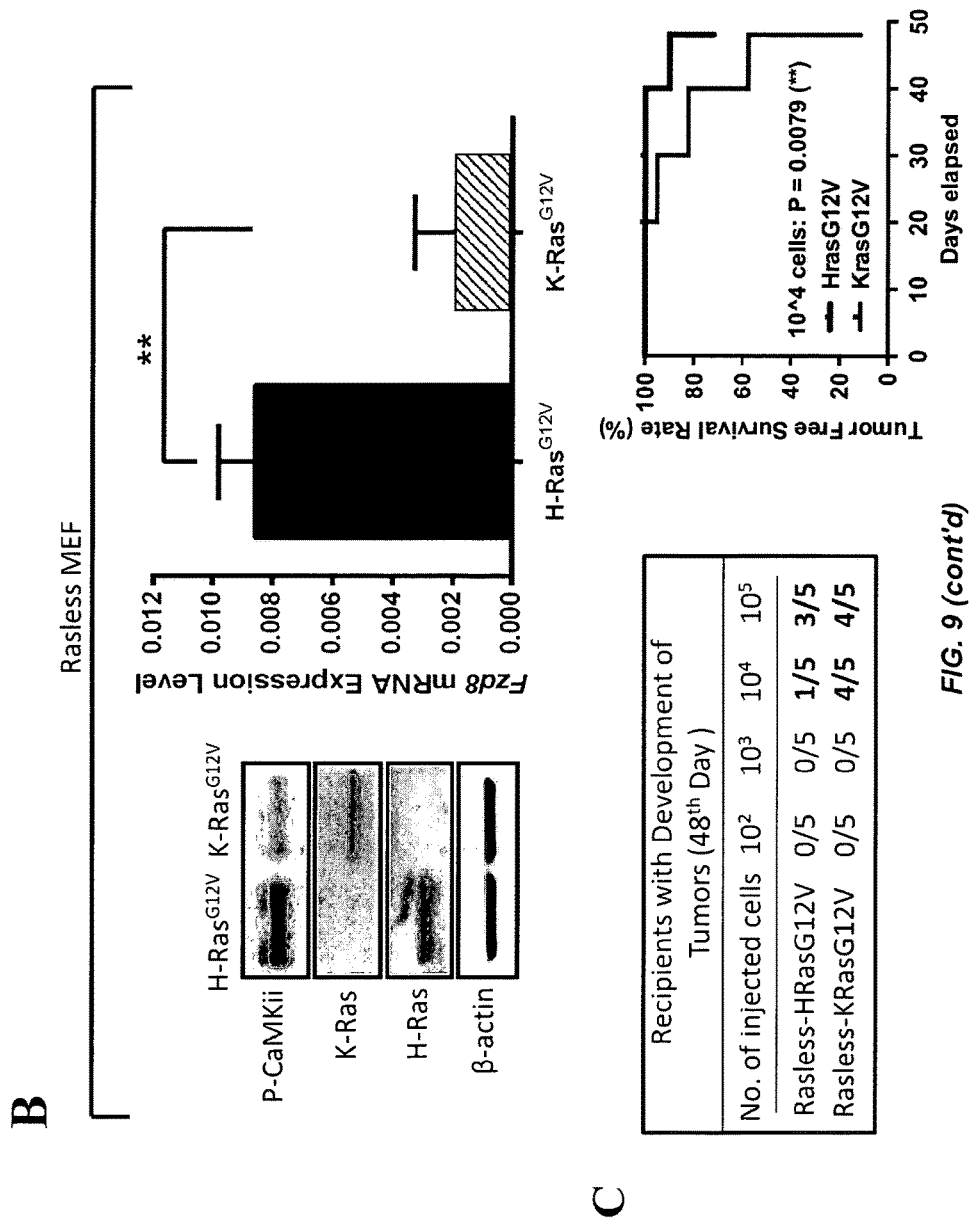
Figure 9:
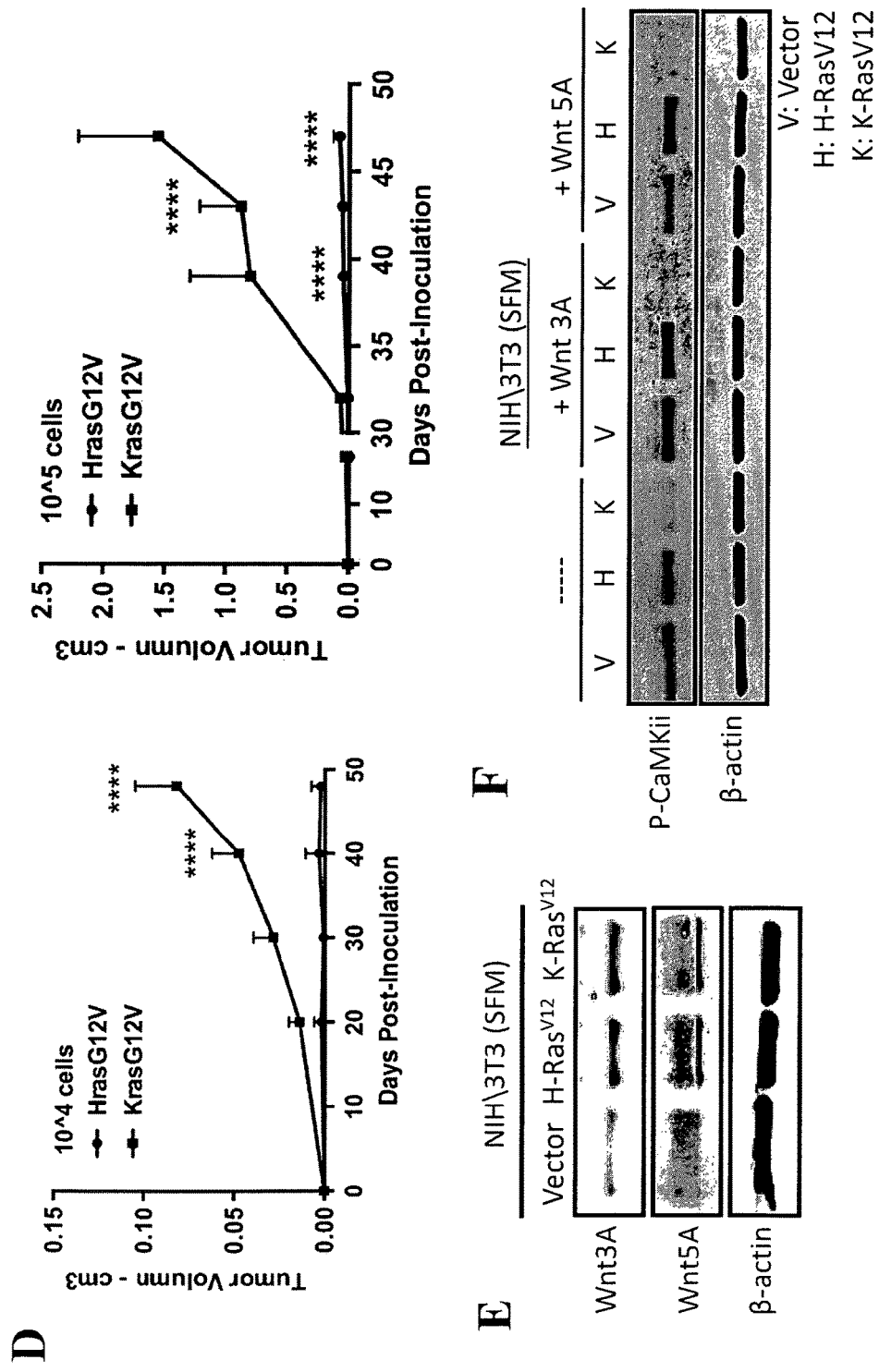
Figure 9:
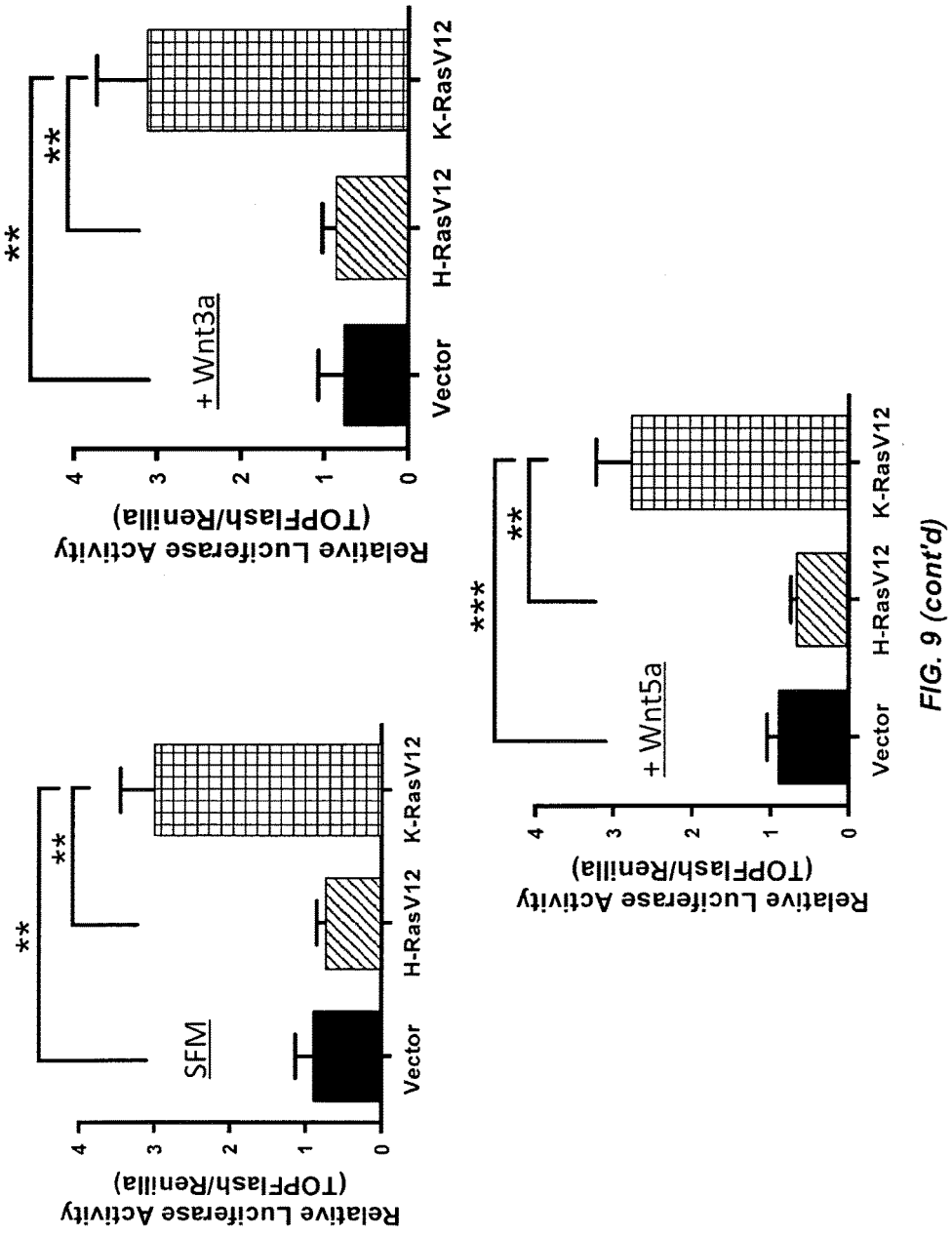
Figure 9:
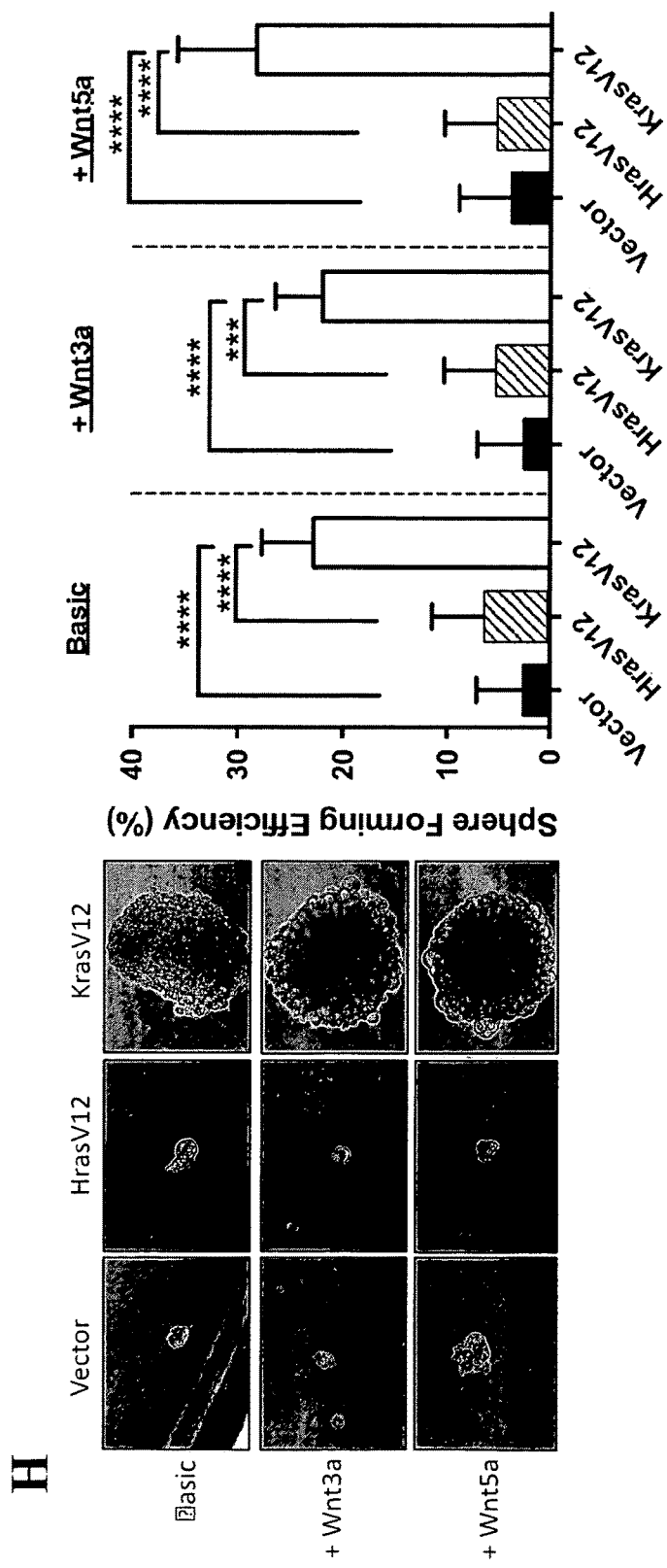

We next determined whether oncogenic K-Ras is required for the maintenance of tumorigenic properties in human pancreatic tumor cells. PANC2.13 and PANC1 cell lines harbor different mutations and exhibit different dependencies on K-Ras. Both cell lines showed a differentiated morphology upon knockdown of K-Ras by shRNAs (FIG. 8G). The expression of cell surface antigens CD44 and CD24 have been shown to be highly correlated with poor clinical diagnosis in pancreatic cancer patients (Ohara et al., *Cancer Sci* 104:1127-1134, 2013). Depletion of oncogenic K-Ras in PANC2.13 and PANC1 cells markedly reduced the expression of CD44 and CD24 (FIG. 9H-I). K-Ras-depleted PANC2.13 cells displayed significantly reduced ability to form spheres with re-plating potential in vitro (FIG. 1G and FIG. 9J), again suggesting a critical role for K-Ras in maintaining phenotypes relating to malignancy.

PANC1 has previously been described as a K-Ras independent cell line (Scholl et al., Cell 137:821-834, 2009; Singh et al., Cancer Cell 15:489-500, 2009; Wei et al., Cancer Lett 322:58-69, 2012). Consistent with these reports, K-Ras knockdown slowed down cell proliferation but did not affect the viability of PANC1 cells growing in 2D (data not shown). However, using a limited number of transplanted cells, we found that K-Ras knockdown significantly reduced the rate of tumor initiation when compared with control PANC1 cells (FIG. 1H). These data suggests that oncogenic K-Ras mediates tumorigenic phenotypes in human pancreatic cancer cell lines, a function which appears distinct from its role in maintaining cell viability and proliferation in 2D cultures.

K-Ras Suppresses Frizzled 8 and CaMKii Activity

Next, we sought to investigate the underlying mechanisms through which K-Ras promotes tumorigenicity much more efficiently than H-Ras, despite comparable levels of canonical Ras signaling. K-Ras4B, but not N-Ras, H-Ras or K-Ras4A, is essential for embryonic development in genetically engineered animal models (Johnson et al., Genes Dev. 11:2468-2481, 1997; Koera et al., Oncogene 15:1151-1159, 1997; Malumbres and Barbacid, Nat Rev Cancer 3:459-465, 2003). Furthermore, K-Ras(4B)$^{V12}$, but not H-Ras$^{V12}$ or N-Ras 12, prevents retinoic acid-induced differentiation in mouse embryonal carcinoma stem cells while maintaining their proliferation and stemness (Quinlan et al., Mol Cell Biol 28:2659-2674, 2008). Therefore, it is possible that K-Ras4B plays a vital and unique role in embryonic stem cells (ESCs). Signaling-focused PCR arrays (SABiosciences, PAMM047A) were used to profile stem cell-related genes mediated by H-Ras or K-Ras (FIG. 2A; Table 1 and Table 2 below). Three mouse stem cell signaling-related genes were identified that were expressed with greater than four-fold change between H-Ras$^{V12}$- and K-Ras$^{V12}$-transformed NIH/3T3 cells (FIG. 2B; Table 3 below). Bone marrow protein receptor type 1B (bmpr1b) was up-regulated in K-Ras$^{V12}$-transformed cells, whereas Gli2 and Frizzled 8 (Fzd8) were down-regulated significantly in NIH/3T3-K-Ras$^{V12}$ cells. We decided not to pursue bmpr1b due to its low endogenous expression level, or Gli2, because its N-terminal repressor domain is shortened in humans when compared to mice, suggesting different roles in these two species (Sasaki et al., Development 126:3915-3924, 1999).

TABLE 1

Quality control of the qPCR array for H-Ras-transformed NIH/3T3 cells

| Array | NIH-3t3-BH-H-RasV12 | NIH-3t3-BH-H-RasV12 | NIH-3t3-BH-H-RasV12 |
|---|---|---|---|
| $C_t$ (GDC) | 35 | 35 | 35 |
| Genomic DNA | Pass | Pass | Pass |

TABLE 2

Quality control of the qPCR array for K-Ras-transformed NIH/3T3 cells

| Array | NIH-3t3-BH-K-RasV12 | NIH-3t3-BH-K-RasV12 | NIH-3t3-BH-K-RasV12 |
|---|---|---|---|
| $C_t$ (GDC) | 35 | 35 | 35 |
| Genomic DNA | Pass | Pass | Pass |

TABLE 3

Layout of genes and expression changes of genes in qPCR array of H-Ras$^{V12}$ and K-Ras$^{V12}$-transformed NIH/3T3 cells

| Layout | 1 | 2 | 3 | 4 | 5 | 6 | 7 | 8 | 9 | 10 | 11 | 12 |
|---|---|---|---|---|---|---|---|---|---|---|---|---|
| A | Acvr1 | Acvr1b | Acvr1c | Acvr2a | Acvr2b | Acvrl1 | Amhr2 | Bcl9 | Bcl9l | Bmpr1a | Bmp1b | Bmpr2 |
|   | −1.06 | −1.15 | 1.92 | 1.04 | −1.04 | 2.92 | 1.47 | 1.08 | −1.89 | −1.07 | 7.79 | −1.13 |
| B | Cdx2 | Crebbp | Ctnnb1 | E2f5 | Eng | Ep300 | Fgfr1 | Fgfr2 | Fgfr3 | Fgfr4 | Fzd1 | Fzd2 |
|   | 1.85 | −1.1 | −1.16 | 1.32 | 1.13 | 1.01 | −1.55 | −2.2 | −1.13 | 2.54 | −1.34 | −1.5 |
| C | Fzd3 | Fzd4 | Fzd5 | Fzd6 | Fzd7 | Fzd8 | Fzd9 | Gli1 | Gli2 | Gli3 | Il6st | Lef1 |
|   | 1.14 | −1.09 | 1.5 | −1.31 | −1.87 | −9.18 | −1.1 | −1.07 | 25.49 | −1.12 | −1.07 | 1.37 |
| D | Lifr | Lrp5 | Lrp6 | Ltbp1 | Ltbp2 | Ltbp3 | Ltbp4 | Ncstn | Nfat5 | Nfatc1 | Nfatc2 | Nfatc3 |
|   | 1.14 | −1.09 | −1.05 | 1.37 | −1.88 | −1.41 | −1.2 | −1.17 | −1.08 | 1.09 | −1.15 | −1.19 |
| E | Nfatc4 | Notch1 | Notch2 | Notch3 | Notch4 | Psen1 | Psen2 | Psenen | Ptch1 | Ptchd2 | Pygo2 | Rbl1 |
|   | −1.63 | 3.57 | 1.96 | 3.94 | 2.79 | 1.01 | −1.5 | 1.04 | 1.32 | 1.12 | −1.14 | −1.07 |
| F | Rbl2 | Rbpjl | Rgma | Smad1 | Smad2 | Smad3 | Smad4 | Smad5 | Smad6 | Smad7 | Smad9 | Smo |
|   | 1.09 | −1.05 | 1 | 1.82 | 1.09 | 1.02 | 1.1 | 1.6 | −2.72 | 1.15 | −3.3 | −1.76 |
| G | Sp1 | Stat3 | Sufu | Tcf3 | Tcf7 | Tcf7l2 | Tgfbr1 | Tgfbr2 | Tgfbr3 | Tgfbrap1 | Vangl2 | Zeb2 |
|   | 1.06 | −1.15 | −1.15 | −1.22 | 2.52 | −2.06 | −1.15 | −1.07 | −1.7 | −1.11 | −1.14 | 1.18 |

Frizzled 8 (Fzd8), a seven-transmembrane G protein-coupled receptor, is a member of the frizzled gene family involved in the regulation of Wnt/β-catenin signaling pathways. Among 10 frizzled family members, Fzd1, Fzd4, and Fzd10 have been identified as activators of the Wnt/β-catenin pathway (Lhomond et al., Development 139:816-825, 2012; Nagayama et al., Cancer Sci 100:405-412, 2009). Recently, Fzd8 has been reported as a major mediator of non-canonical Wnt/Ca$^{2+}$ signaling that maintains the quiescence of hematopoietic stem cells (Sugimura et al., Cell 150:351-365, 2012). The non-canonical Wnt/Ca$^{2+}$ pathway, which entails the activation of CaMKii and the transcription factor NF-AT, inhibits β-catenin/TCF signaling (Saneyoshi et al., Nature 417:295-299, 2002; Semenov et al., Cell 131:1378, 2007; Sugimura and Li., Birth Defects Res C Embryo Today 90:243-256, 2010). Therefore we determined whether down-regulation of Fzd8 in oncogenic K-Ras transformed cells led to repression of non-canonical Wnt/Ca$^{2+}$ signaling and subsequent activation of β-catenin/TCF activity.

Figure 2:
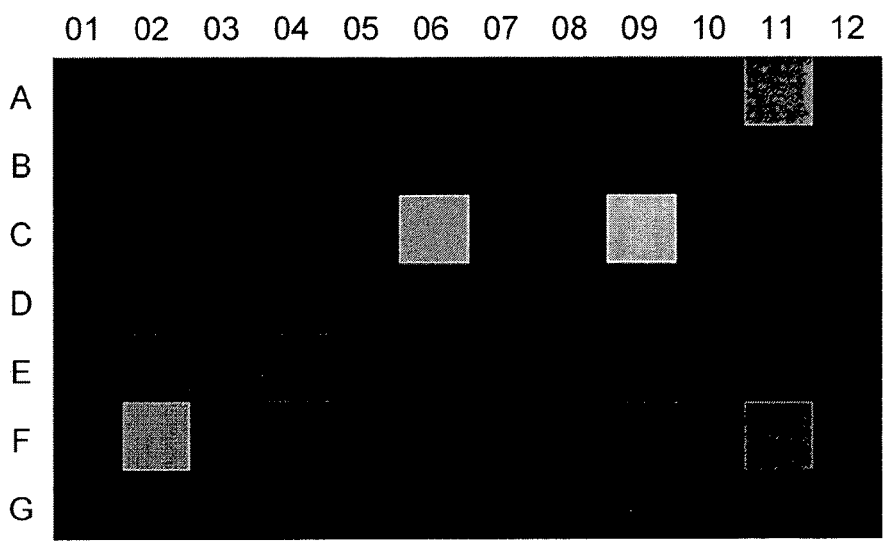
FIG. 2. K-Ras, but not H-Ras, suppresses Fzd8. (A) Heat map of stem cell factors differentially expressed in H-Ras$^{V12}$ and K-Ras$^{V12}$-transformed NIH/3T3 cells as evaluated by qPCRarray (N=3). (B) Scatter plot (left) and identification of Bmpr1b, Fzd8, and Gli2 as genes differentially expressed in H-Ras$^{V12}$ and K-Ras$^{V12}$-transformed NIH/3T3 cells. (C) Reduced Fzd8 expression and Wnt/Ca$^{2+}$ signaling in K-Ras transformed NIH/3T3 cells when compared with the vector control or H-Ras$^{V12}$-transformed cells (Top eight panels) and in mouse PDAC cells with oncogenic K-Ras mutation when compared with those with mutant Raf (Bottom four panels). (D) Increased TCF4 and β-catenin complexes in K-Ras$^{V12}$-transformed NIH/3T3 cells (Top panel) and in mouse PDAC cells with K-Ras mutations (Bottom panel) when compared to those with H-Ras$^{V12}$ or B-Raf, respectively. (E) Increased TCF/β-catenin activities in K-Ras$^{V12}$-transformed NIH/3T3 cells as compared to the vector control or H-Ras$^{V12}$-transformed NIH/3T3 cells (N=4). (F) Knockdown of K-Ras led to increased Fzd8 expression at mRNA level in PANC2.13 and PANC1 cells (N=3). (G) Reduction in the levels of Fzd8 expression and CaMKii phosphorylation in skin tumors harboring wt H-Ras KO with mutations in either Kras and HrasKI alleles. (H) Knockdown of K-Ras increased Fzd8 protein level, non-canonical Wnt signaling (p-CaMKii), and increased phosphorylation of β-catenin. (I) Knockdown of K-Ras in PANC2.13 cells reduced canonical Wnt signaling as revealed by TOPFlash assay (N=4).
Figure 2:
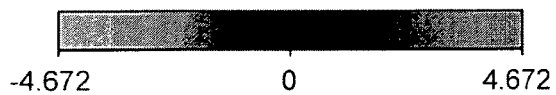
Figure 2:
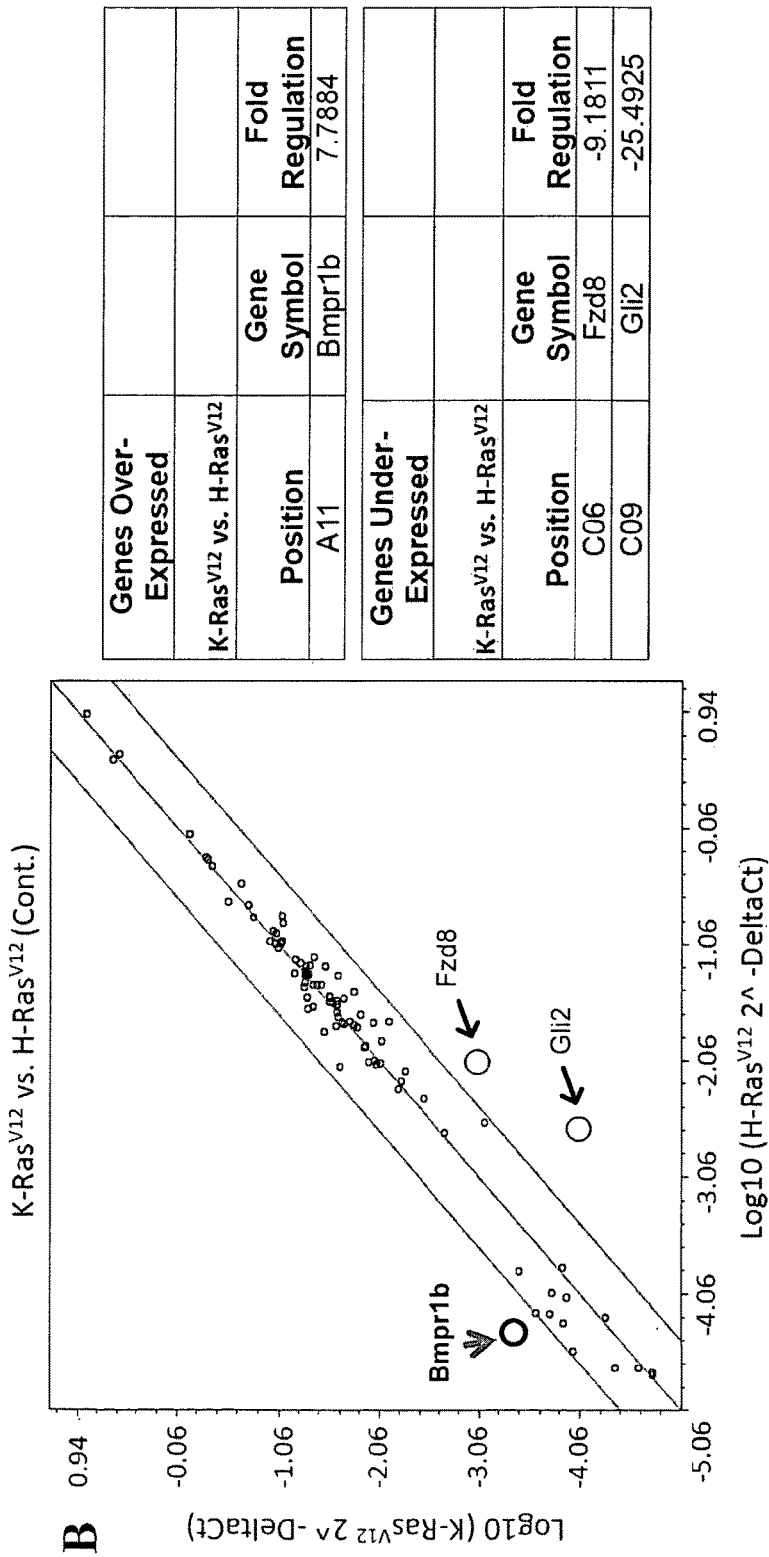
Figure 2:
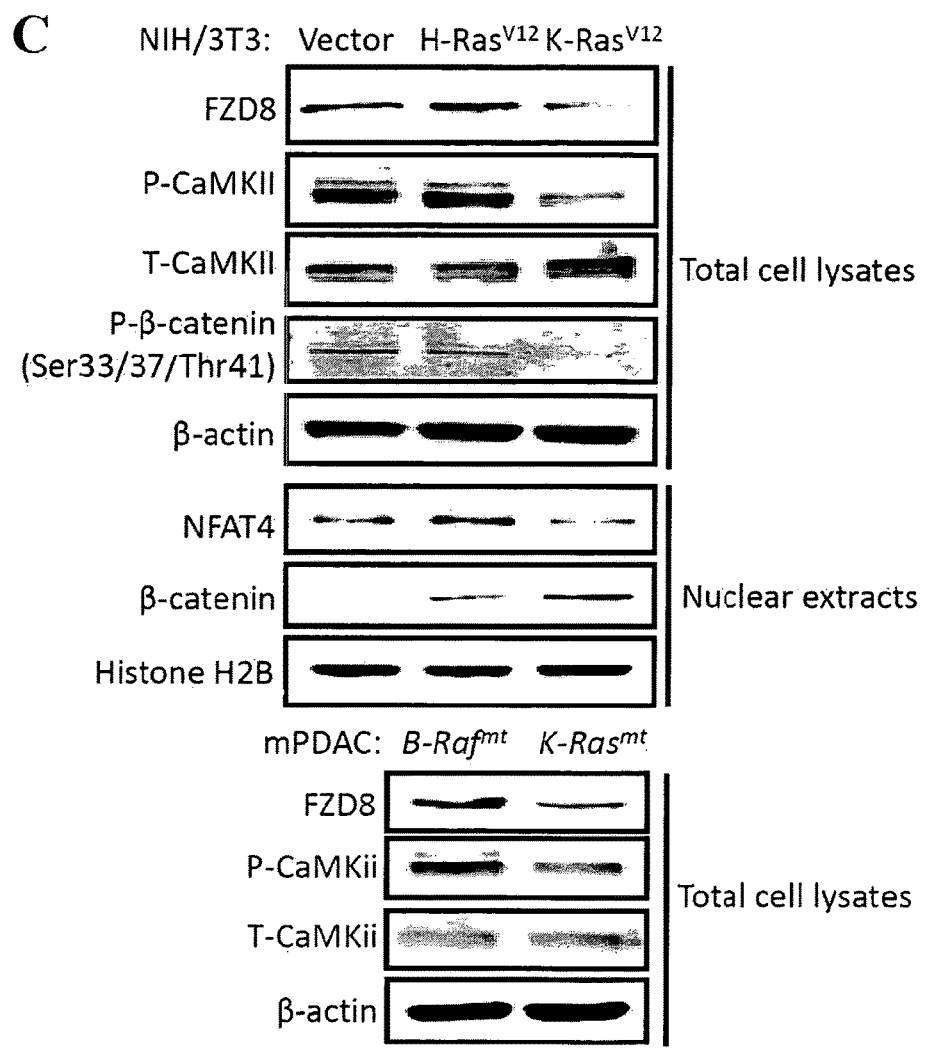
Figure 2:
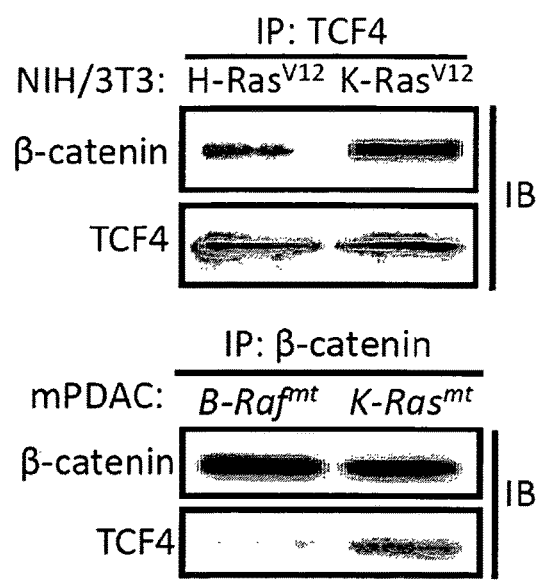
Figure 2:
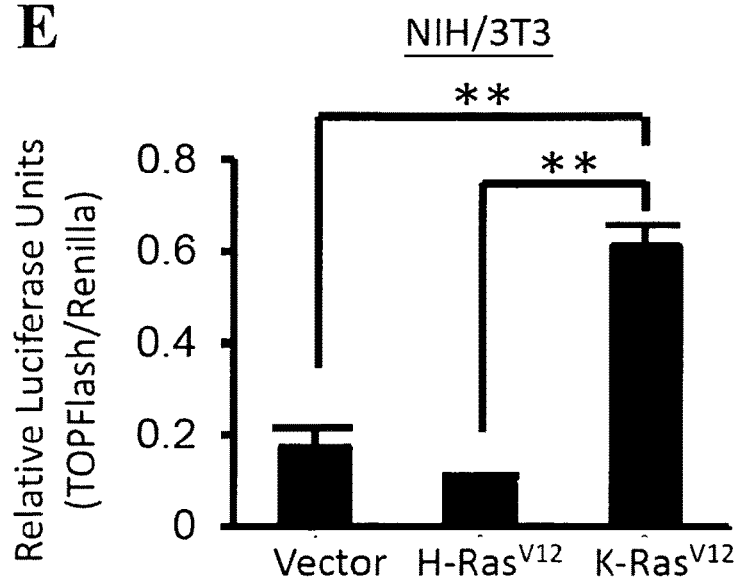
Figure 2:
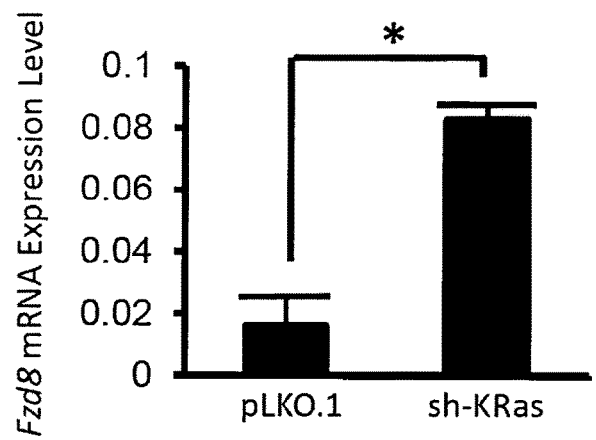
Figure 2:
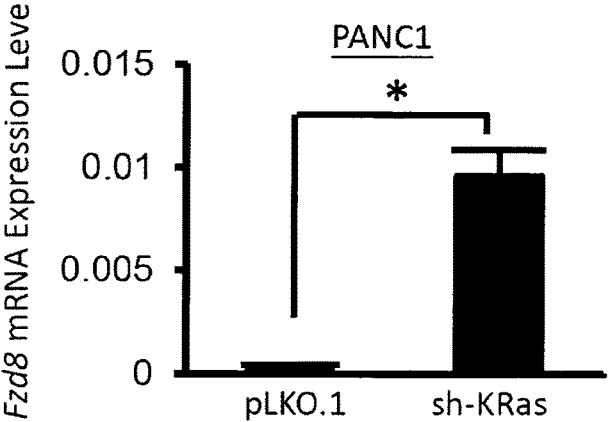
Figure 2:
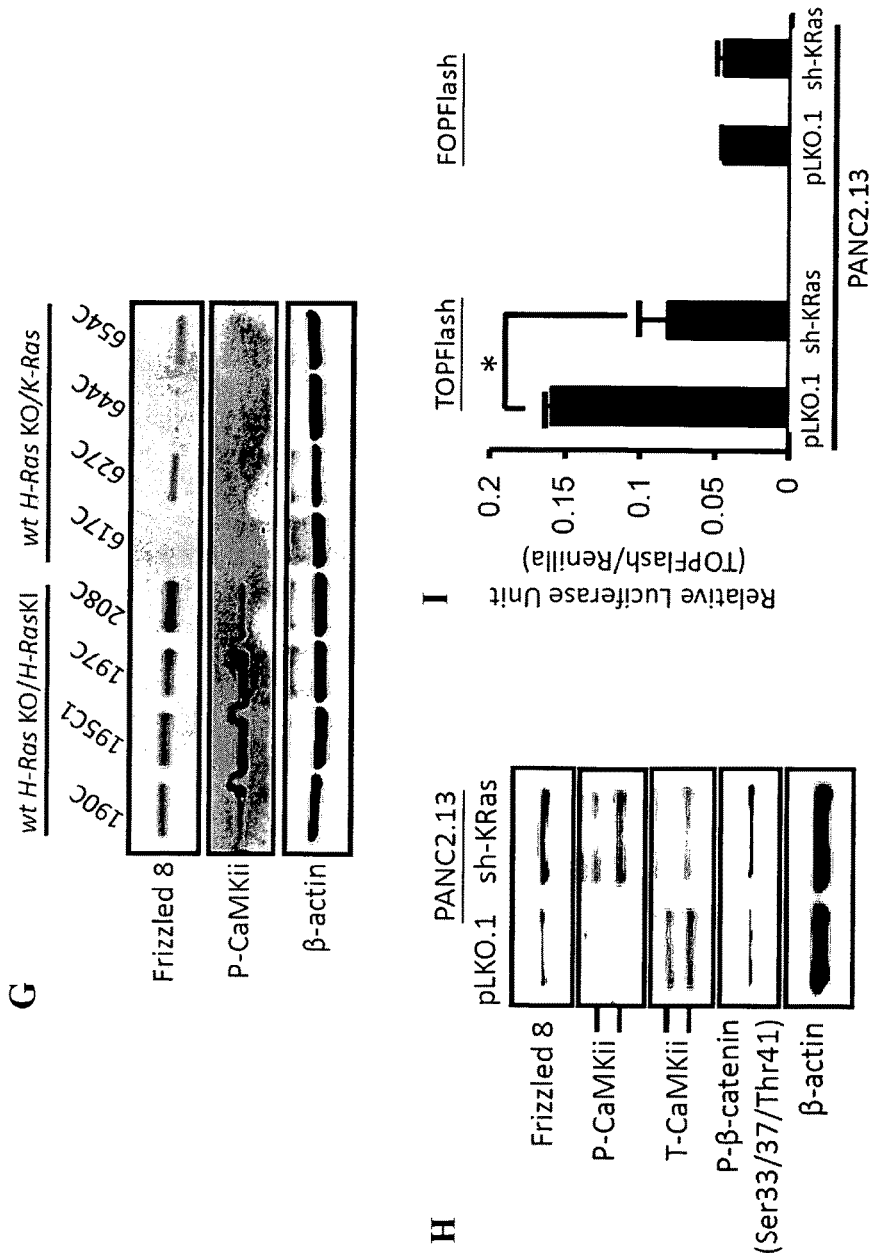

Western blot analysis confirmed that Fzd8 was downregulated in K-Ras$^{V12}$-transformed NIH/3T3 cells compared with H-Ras$^{V12}$-transformed cells and vector controls (FIG. 2C). K-Ras$^{V12}$-transformed cells also had drastically reduced levels of activated CaMKii, as indicated by the decrease in auto-phosphorylation at Thr286 (FIG. 2C). The gene products of active NF-AT inhibit disheveled-mediated GSK3β repression, resulting in phosphorylation, cytosolic accumulation, and degradation of β-catenin (Saneyoshi et al., *Nature* 417:295-299, 2002). Cell fractionation analyses revealed that activation and nuclear translocation of NF-AT was reduced in NIH/3T3-K-Ras$^{V12}$ cells in comparison with vector control and NIH/3T3-H-Ras$^{V12}$ cells (FIG. 2C). Western blotting analysis further suggested that the phosphorylated form of β-catenin was reduced in these cells (FIG. 2C). Interestingly, tumor cells isolated from oncogenic K-Ras driven mouse PDACs (mPDACs) also displayed reduced Fzd8 expression and repressed levels of phospho-CaMKii when compared with mPDACs induced by oncogenic B-Raf (FIG. 2C).

Activation of the CaMKii pathway also suppresses canonical Wnt signaling by blocking β-catenin and TCF interaction, thus inhibiting β-catenin-dependent transcription (Semenov et al., *Cell* 131:1378, 2007; Sugimura and Li., *Birth Defects Res C Embryo Today* 90:243-256, 2010). Co-immunoprecipitation indicated that K-Ras$^{V12}$-transformed NIH3T3 cells, in which CaMKii was barely phosphorylated, showed increased interaction between β-catenin and TCF4 when compared with H-Ras$^{V12}$-transformed cells, in which CaMKii activity was elevated (FIG. 2D). Furthermore, reduced activation of CaMKii and NF-AT in NIH/3T3-K-Ras$^{V12}$ cells led to increased nuclear localization of β-catenin, whereas in vector controls and NIH/3T3-H-Ras$^{V12}$ cells, in which CaMKii and NF-AT were highly activated, nuclear β-catenin was barely detectable (FIG. 2C). In comparison with B-Raf$^{mt}$-induced mouse mPDACs, tumor cells harboring mutant K-Ras showed increased β-catenin-TCF4 interaction (FIG. 2D). TOPFlash assays further confirmed that the transcriptional activity of β-catenin was greatly elevated in NIH/3T3-K-Ras$^{V12}$ cells when compared with the vector and NIH/3T3-H-Ras$^{V12}$ cells (FIG. 2E). Consequentially, the mRNA expression of β-catenin-target genes, c-Myc and TCF1, were upregulated in K-Ras$^{V12}$-transformed cells in comparison with vector control or H-Ras$^{V12}$-transformed cells (FIG. 9A).

Mutant/oncogenic Ras-drive signaling activities and tumorigenicity were long considered independent of wild-type Ras isoforms. However, there is mounting evidence to suggest that the biological outputs of oncogenic K-Ras are subject to wild-type Ras protein-dependent modulation (Grabocka et al., *Cancer Cell* 25:243-256, 2014; Young et al., *Cancer Discov* 3:112-123, 2013). To determine whether the presence of wild-type Ras alleles affect the Fzd8-CaMKii signaling pathway distinctly mediated by oncogenic K-Ras, we expressed N-, H-, or K-Ras$^{V12}$ in mouse embryo fibroblasts (MEFs) that are devoid of Ras proteins (H-Ras$^{-/-}$; N-Ras$^{-/-}$ and K-Ras$^{lox/lox}$) (Drosten et al., *EMBO J* 29:1091-1104, 2010). As shown in FIG. 9B, the "Rasless" MEF expressing only K-Ras(4B)$^{V12}$ showed lower expression of Fzd8 and phospho-CaMKii than the cells expressing only H-Ras$^{V12}$. Interestingly, an in vivo limited transplantation assay suggested that Ras$^{-/-}$ MEF-K-Ras(4B)$^{V12}$ initiated tumor formation at higher frequency than Ras$^{-/-}$ MEF-H-Ras$^{V12}$ (FIG. 9C). In addition, the tumors derived from Ras$^{-/-}$ MEF-K-Ras(4B)$^{V12}$ displayed significantly higher growth rates than the tumors initiated by Ras$^{-/-}$ MEF-H-Ras$^{V12}$ (FIG. 9D). Taken together, our data in NIH\3T3 and rescued Rasless cells suggest that, regardless of whether wild-type Ras proteins are present or not, K-Ras and H-Ras differ unequivocally in tumorigenicity as well as in signaling through the non-canonical Wnt/Ca$^{2+}$ signaling pathway.

Next, we asked whether non-canonical Wnt/Ca$^{2+}$ signaling differs in tumors driven by H-Ras or K-Ras. To do this, we compared tumors from wild-type mice with tumors from a genetically engineered mouse model devoid of endogenous H-Ras, but expressing wild-type H-Ras knocked into the endogenous K-Ras locus. Tumorigenesis and K- or H-Ras mutations were then induced by topical treatment with DMBA/TPA. This model allows equal comparison of K- and H-Ras oncogenes under control of the same endogenous regulatory elements (Potenza et al., *EMBO Rep* 6:432-437, 2005; To et al., *Nat Genet* 40:1240-1244, 2008) in the same cellular background. Intriguingly, mutant H-Ras driven skin tumors in this model had elevated level of Fzd8 protein and increased levels of phosphorylated-CaMKii when compared to skin tumors with K-Ras mutations (FIG. 2G). The data further suggest that this unique K-Ras-mediated signaling cannot be recapitulated by H-Ras even when it is knocked in at the K-Ras locus.

Despite their different downstream effectors, active canonical and non-canonical Wnt signal transduction cascades are commonly regulated by the binding of frizzled receptors to Wnt ligands. Distinct from other WNT family members, such as WNT3a which preferably activate Wnt/β-catenin/TCF signaling transduction, WNT5a is a classic non-canonical Wnt signaling pathway activator (Weekes and Winn, *Cancers* 3:3676-3686, 2011). To assess whether different WNT ligands are involved in modulating the distinguishable Wnt/Ca$^{2+}$ signaling activity of oncogenic H- and K-Ras, we further evaluated the expression levels and functions of WNT-5a and -3a in Ras$^{V12}$-transformed NIH\3T3 cells. As shown in FIG. 9E, oncogenic Ras$^{V12}$ transformed cells expressed more WNT-3a and -5a protein than control cells, but there was no evident difference in expression levels between H- and K-Ras$^{V12}$. Furthermore, the additional presence of WNT ligands did not alter CaMKii activity, β-catenin/TCF/LEF transcriptional activity, as well as sphere forming efficiency in H- or K-Ras$^{V12}$ transformed cells (FIG. 9F-H). The data suggest that the substantial divergence between H- and K-Ras in non-canonical Wnt/Ca$^{2+}$ signaling is not dependent upon the presence of WNT ligands.

Since oncogenic K-Ras led to suppression of Fzd8 expression and decreased CaMKii phosphorylation in NIH/3T3 cells, we next determined the effects of knockdown of oncogenic K-Ras on Fzd8 in cancer-derived cell lines. In human pancreatic cancer cells, K-Ras knockdown increased Fzd8 expression and increased phosphorylation of CaMKii in human pancreatic cancer cell lines (FIG. 2H). When K-Ras expression was knocked down, PANC2.13 cells displayed significantly reduced β-catenin activity as evaluated by the TOPFlash assay (FIG. 2I). Based on the above results, we conclude that oncogenic K-Ras, but not H-Ras, represses Fzd8 expression and CaMKii activity, a major effector of the Wnt/Ca$^{2+}$ pathway, in mouse and human cancer cells.

Here we report that the activity of the canonical Wnt/β-catenin signaling pathway is modulated by the Fzd8-mediated non-canonical Wnt/Ca$^{2+}$ pathway in K-Ras$^{V12}$-transformed cells and in pancreatic cancer cells containing oncogenic K-Ras. However, mutations in genes involved in canonical Wnt/β-catenin activity occur in many types of cancers. In colorectal cancers, in which K-Ras mutations occur in around 50% of cases, mutations in the Wnt/β-catenin signaling pathway acts as a major initiating drivers, usually through mutations that inactivate the APC (adenomatous polyposis coli) gene. Therefore, we sought to investigate whether APC loss/mutation makes the malignant features associated with K-Ras irrelevant to Fzd8 downregulation and stem-ness in colorectal cancer cells. Knock down of K-Ras promoted the expression of Fzd8 and the activation of NF-AT or CaMKii in multiple colon cancer cell lines regardless of the status of wild type or mutant APC (FIG. 10A). As expected from our model, knock-down of K-Ras significantly repressed β-catenin/TCF/LEF transcriptional activity in SW480 (mutant APC), which express wild type β-catenin, yet not in either HCT15 (mutant APC) or HCT116 (wild type APC) which have gain of function mutation in β-catenin (FIG. 10B). Even though repression of K-Ras expression by shRNA did not after β-catenin/TCF/LEF transcriptional activity in HCT15 and HCT116 cells, it still inhibited their sphere formation ability in 3D culture (FIG. 10C). However, the cell proliferation rate indicated by BrdU incorporation was not inhibited in HCT15 and HCT116 upon K-Ras knock down (FIG. 10D). This result led to an interesting question: Is the K-Ras-mediating malignancy independent from canonical Wnt/β-catenin/TCF/LEF transcriptional activity?

To address this question, we treated NIH/3T3 cells transformed by oncogenic H- or K-Ras$^{V12}$ with a series of tankyrase inhibitors, JW55, JW67 and cardionogen1. JW55 and JW67 function as potent inhibitors of canonical Wnt/β-catenin signaling pathway by directly degrading β-catenin, and cardionogen1 inhibits the transcriptional activity of Wnt/β-catenin/TCF/LEF. TOPFlash assay revealed that tankyrase inhibitors successfully repressed β-catenin/TCF/LEF transcriptional activity in Ras$^{V12}$-transformed cells (FIG. 10E). However, the repressed β-catenin function did not correspondingly affect their growth in 3D culture: K-Ras$^{V12}$ transformed cells still maintained their sphere forming efficiency in the presence of JW55, JW67 or cardionogen1, while these compounds inhibited sphere formation in vector control or H-Ras$^{V12}$ transformed NIH/3T3 (FIG. 10F). The data suggest that, despite the fact that we used changes in β-catenin/TCF/LEF transcriptional activity as the readout of non-canonical Wnt/Ca$^{2+}$ signaling activity in cells with wild type β-catenin, the K-Ras driven malignancy is independent from the functions of Wnt/β-catenin signaling pathway.

Inhibition of CaMKii Enhances Sphere Formation by H-Ras$^{v12}$ Cells

Figure 3:
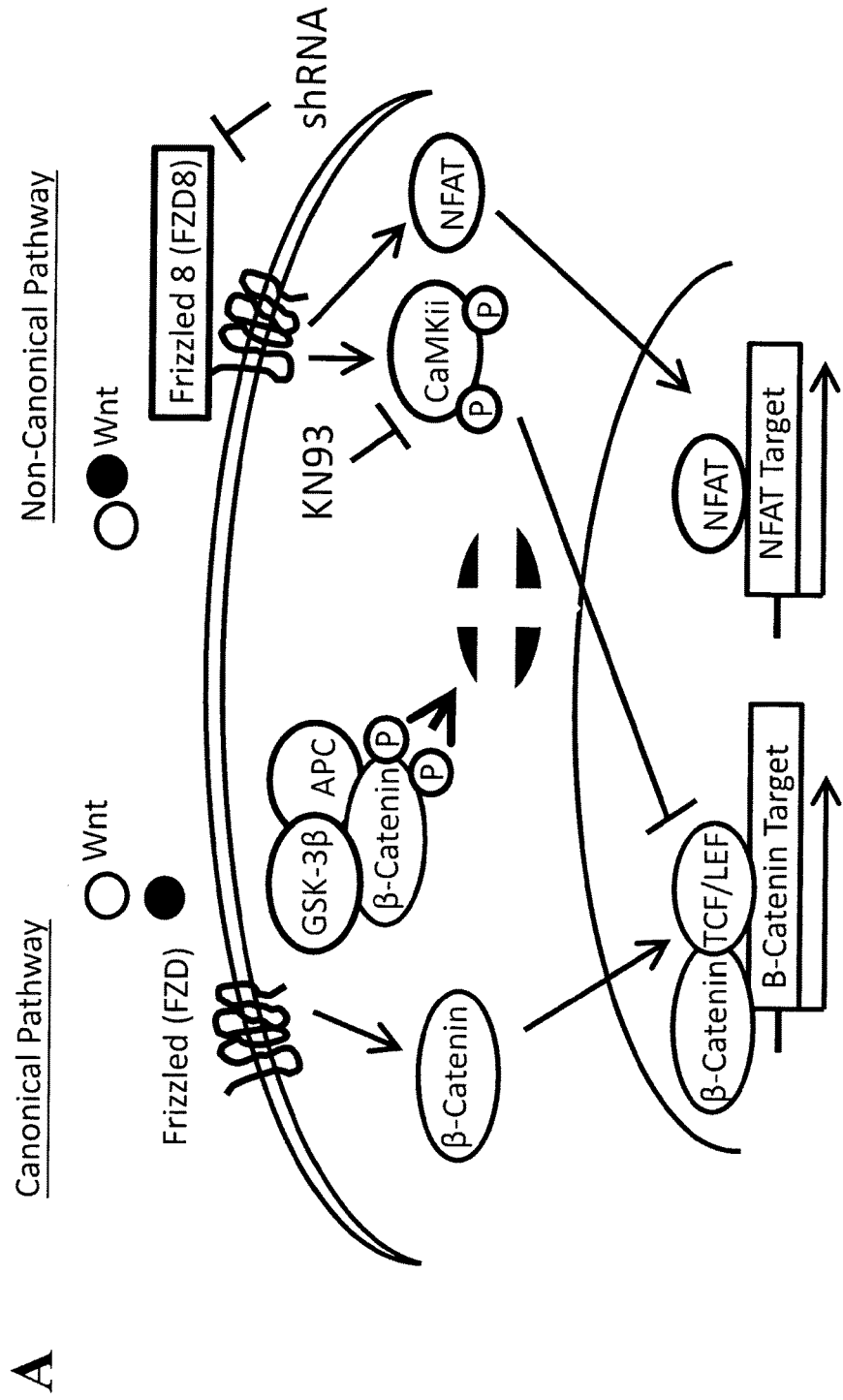
FIG. 3. Fzd8-mediated non-canonical Wnt/Ca2+ signaling suppresses the tumor promoting properties of H-Ras$^{V12}$-transformed NIH/3T3 cells. (A) Schematic illustration of Fzd8 in non-canonical Wnt/Ca$^{2+}$ signaling pathway and its crosstalk with canonical Wnt signaling. Small molecule, KN-93, and shRNA against Fzd8 were used to block CaM-Kii activity and Fzd8 expression for following experiments. (B) Inhibition of CaMKii by KN-93 reduced phosphorylation of CaMKii and reduced the expression of Fzd8. (C) KN-93 treatment stimulated β-catenin transcriptional activities in H-Ras$^{V12}$-transformed NIH/3T3 cells (N=4). (D) Inhibition of CaMKii by KN-93 enhanced sphere formation in H-Ras$^{V12}$-transformed NIH/3T3 cells, but not in K-Ras$^{V12}$-transformed NIH/3T3 cells (N=6). (E-F) Knockdown of Fzd8 in H-Ras$^{V12}$-transformed NIH/3T3 cells reduced phospho-CaMKii levels (E) and stimulated β-catenin transcriptional activities (N=4) (F). (G) Knockdown of Fzd8 in H-Ras$^{V12}$-transformed NIH/3T3 cells promoted sphere formation and re-plating efficiency (N=6). (H) Knockdown of Fzd8 in H-Ras$^{V12}$-transformed NIH/3T3 cells enhanced their tumor initiating abilities. * $P<0.05$;  $P<0.01$; * $P<0.001$.
Figure 3:
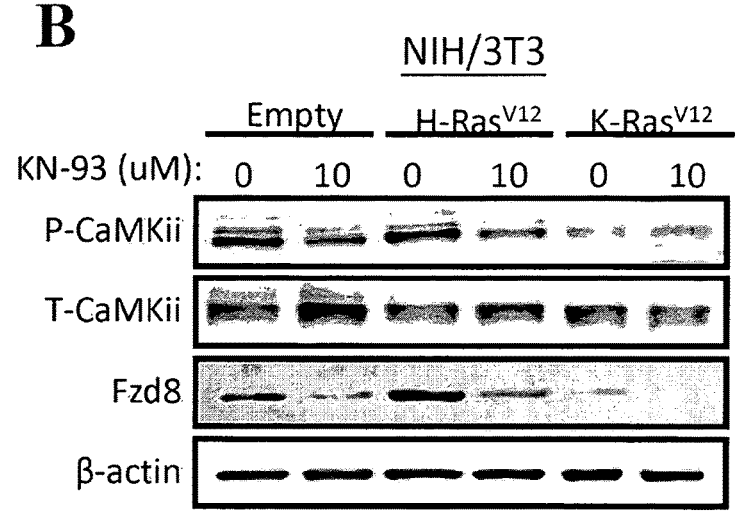
Figure 3:
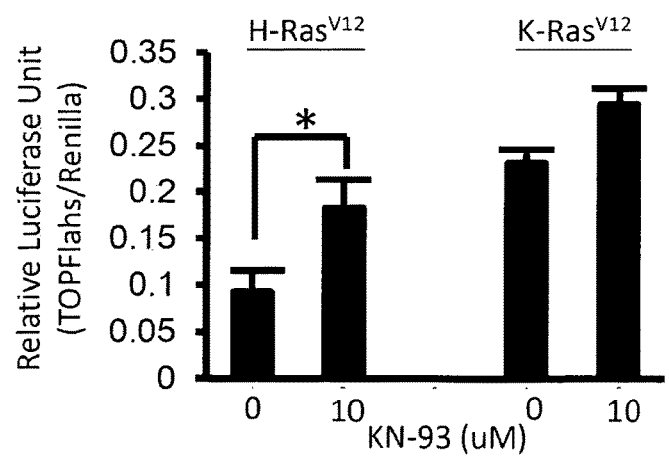
Figure 3:
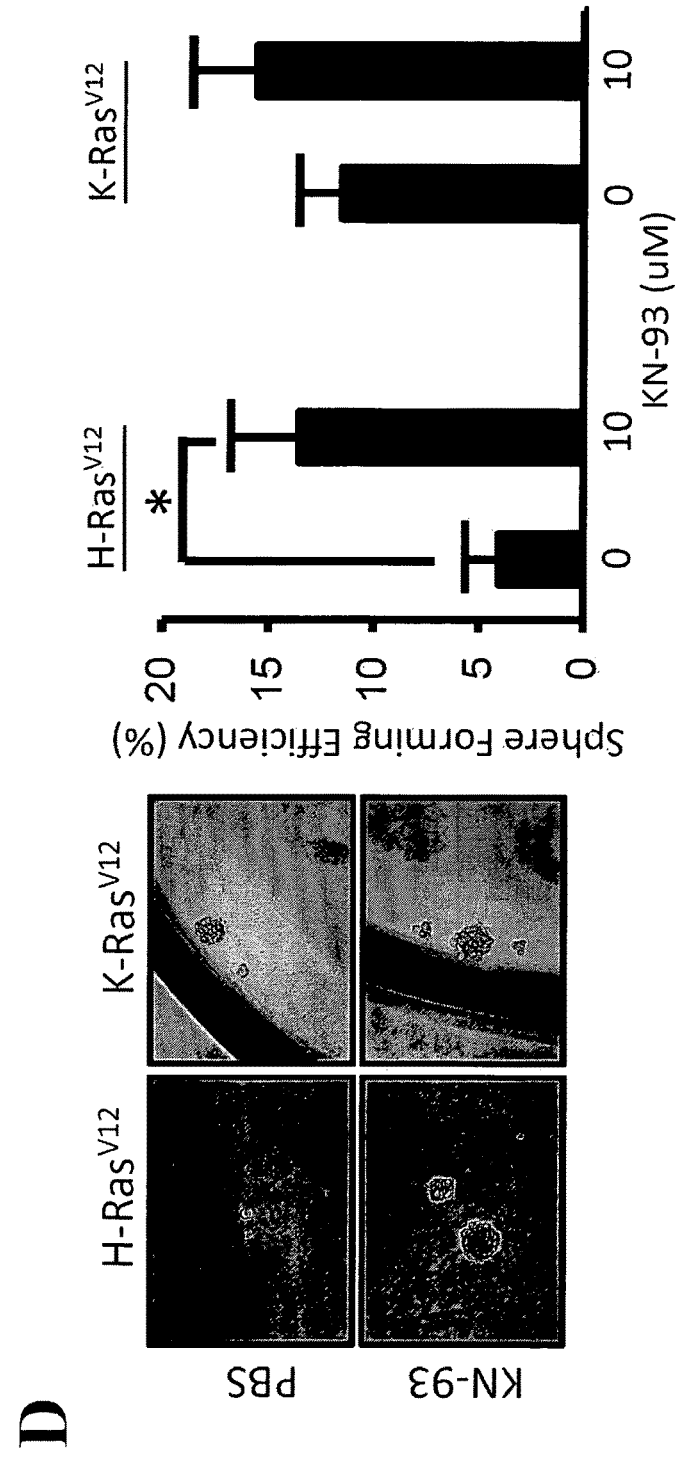
Figure 3:
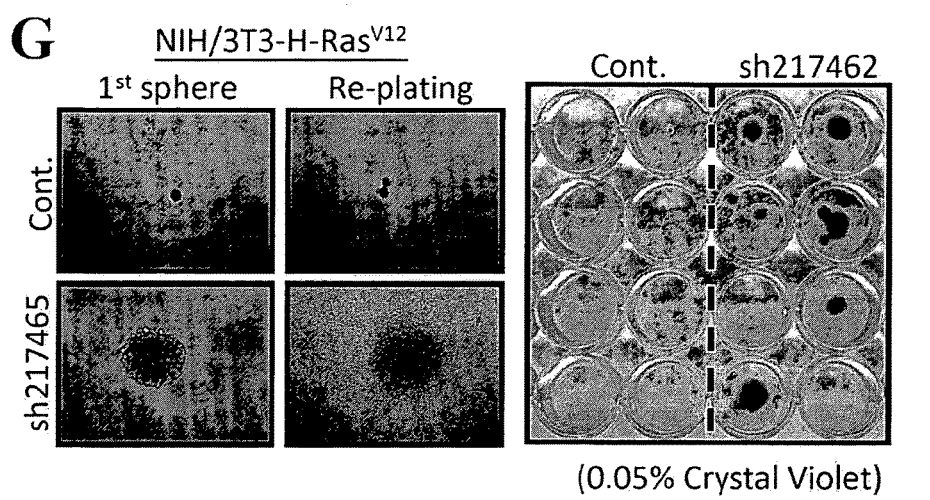
Figure 3:
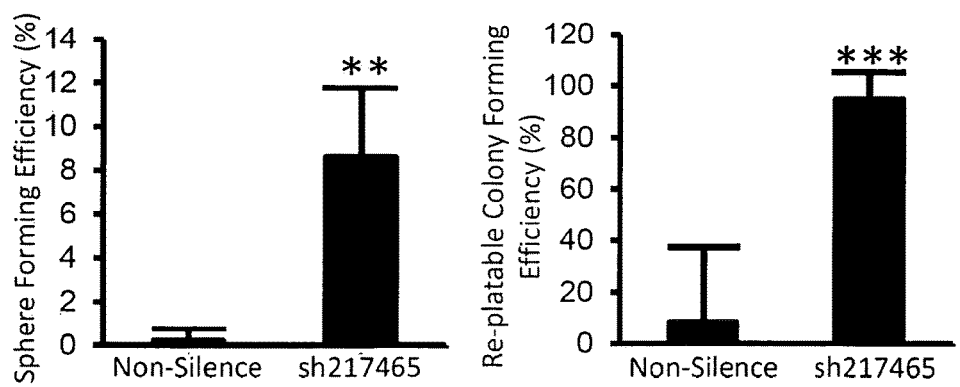
Figure 3:
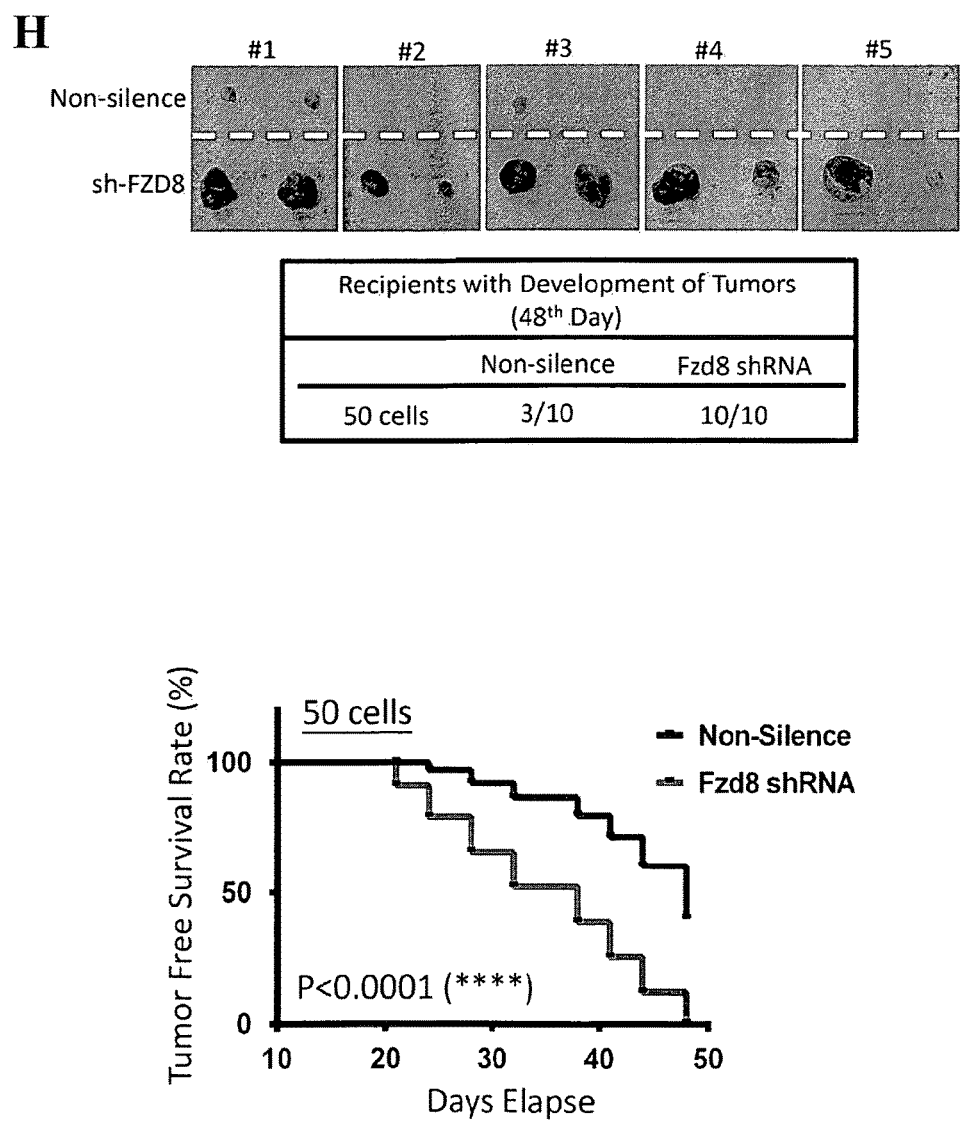

To determine whether suppression of the Wnt/Ca$^{2+}$ signaling pathway observed in K-Ras transformed cells is responsible for the acquisition of stem-like properties, we treated NIH/3T3-H-Ras$^{V12}$ and vector control cells with KN-93, a selective CaMKii inhibitor (FIG. 3A). The treatment reduced phosphorylation of CaMKii (FIG. 3B). Strikingly, KN-93 also reduced Fzd8 expression (FIG. 3B) and increased β-catenin transcriptional activity in NIH/3T3-H-Ras$^{V12}$ cells, confirming the inhibitory effects of Wnt/Ca$^{2+}$/CaMKii signaling on the canonical Wnt pathway (FIG. 3C). Moreover, KN-93 treatment dramatically enhanced the sphere forming efficiency and the size of spheroid colonies in NIH/3T3-H-Ras$^{V12}$ cells (FIG. 3D), suggesting that down-regulation of CaMKii activity is essential for the induction of malignant features observed in K-Ras transformed cells.

Knock-Down of Fzd8 Induces Tumorigenicity in H-Ras$^{v12}$ Cells

To further determine the role of Fzd8 in Wnt/Ca$^{2+}$ signaling, we knocked Fzd8 down in NIH/3T3-H-Ras$^{V12}$ cells with shRNA (FIGS. 3A & E). We observed reduced phospho-CaMKii levels, and enhanced β-catenin activity (FIG. 3E-F). In vitro formation of spheres with re-plating ability was also enhanced upon Fzd8 knockdown in NIH/3T3-H-Ras$^{V12}$ cells (FIG. 3G). Importantly, in a limited transplantation assay, mice subcutaneously injected with 50 NIH/3T3-H-Ras$^{V12}$ shFzd8 cells showed significantly reduced tumor-free survival, when compared with the parental control cells that expressed Fzd8 (FIG. 3H). Thus, suppression of Fzd8 expression and subsequent repression of the Wnt/Ca$^{2+}$ pathway enhances tumor initiation in H-Ras$^{V12}$-transformed NIH/3T3 cells, phenocopying the effects of oncogenic K-Ras.

Roles of Fzd8 in K-Ras-Driven Cancers

Figure 4:
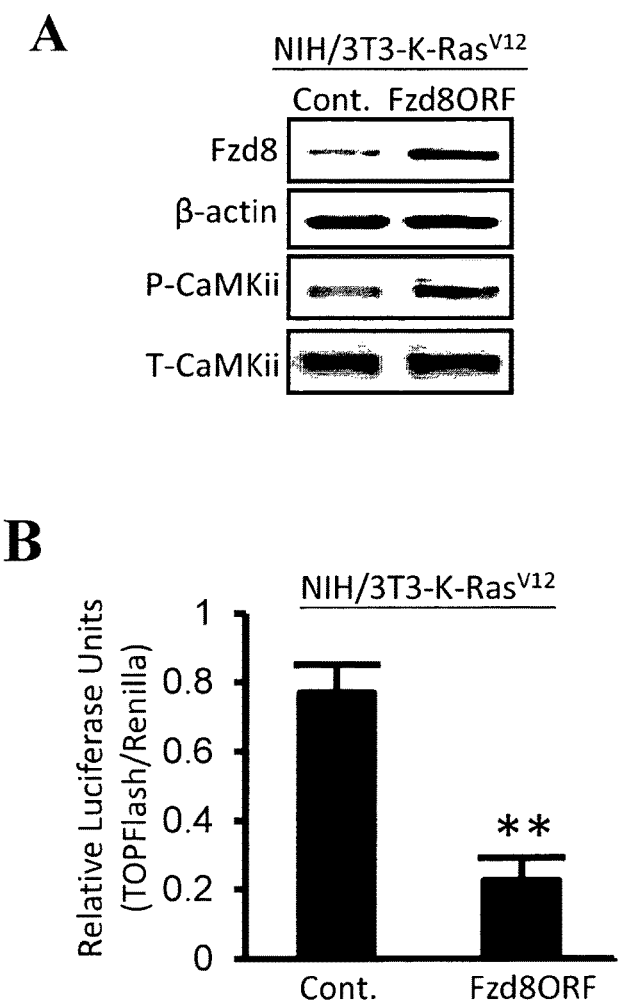
FIG. 4. Downregulation of Fzd8 is required for K-Ras to enhance tumor initiation. (A-B) Restoration of Fzd8 expression in K-Ras$^{V12}$-transformed NIH/3T3 cells enhanced Wnt/Ca$^{2+}$ signaling (A) and reduced β-catenin transcriptional activities (B) (N=4). (C) Restoration of Fzd8 in K-Ras$^{V12}$-transformed NIH/3T3 cells reduced sphere formation and re-plating efficiency (N=6). (D) Restoration of Fzd8 reduced tumor initiating capacity of K-Ras$^{V12}$-transformed NIH/3T3 cells. (E) Fzd8 restoration in PANC1 cells enhanced Wnt/Ca$^{2+}$ signaling as revealed by NF-AT transcriptional activities (N=4) and reduced β-catenin activities (N=4). (F) Fzd8 restoration reduced the tumor initiating ability of PANC1 cells. (G) Down-regulation of Fzd8 in human pancreatic tumor tissues. Left panels: Micrographs of tissue sections immunostained for Fzd8 in human pancreatic normal and malignant tissues. (H) H-scores of Fzd8 immunoreactivities in pancreatic tissue arrays including normal or malignant pancreatic tissues. (I) RNAscope in situ hybridization probed for human Fzd8 in cancer adjacent pancreatic normal tissue and pancreatic adenocarcinoma. * $P<0.05$;  $P<0.01$; * $P<0.001$.
Figure 4:
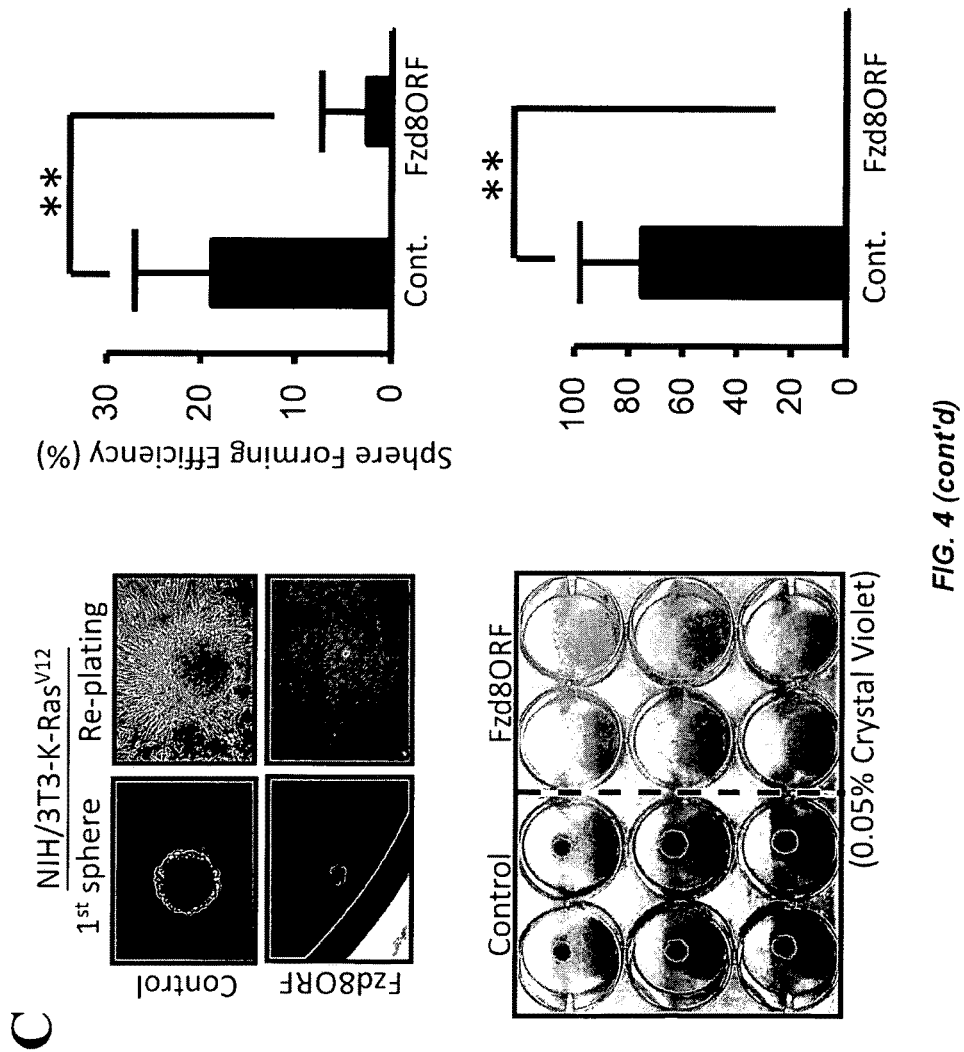
Figure 4:
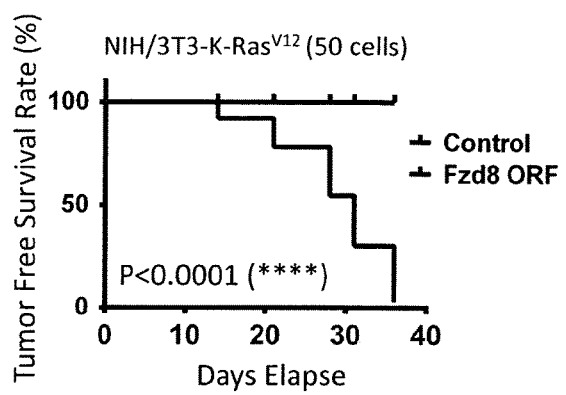
Figure 4:
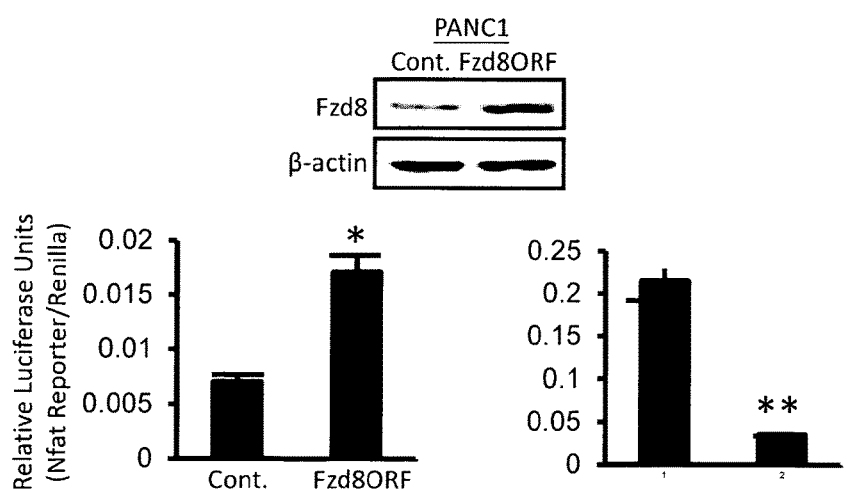
Figure 4:
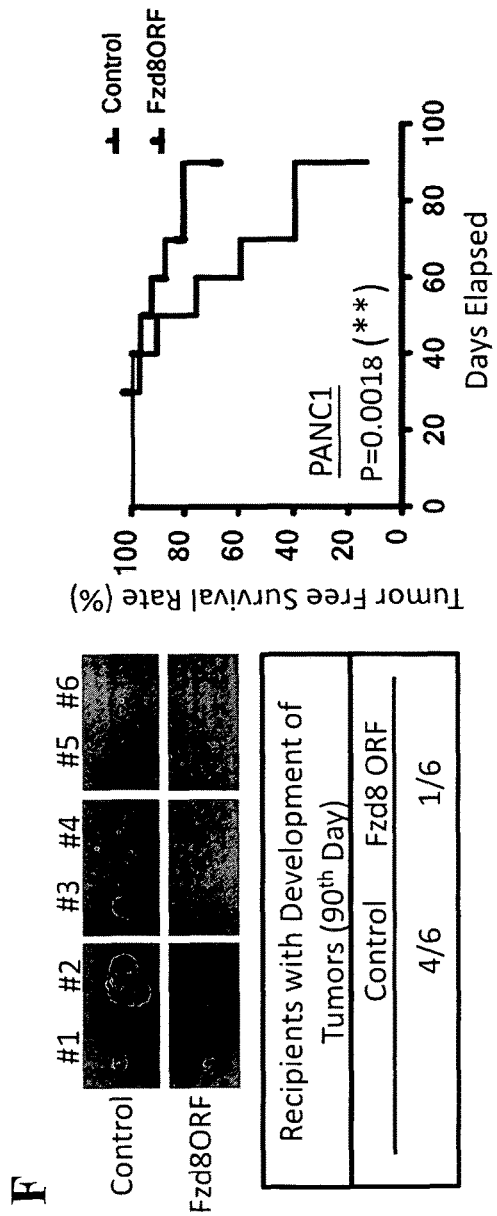
Figure 4:
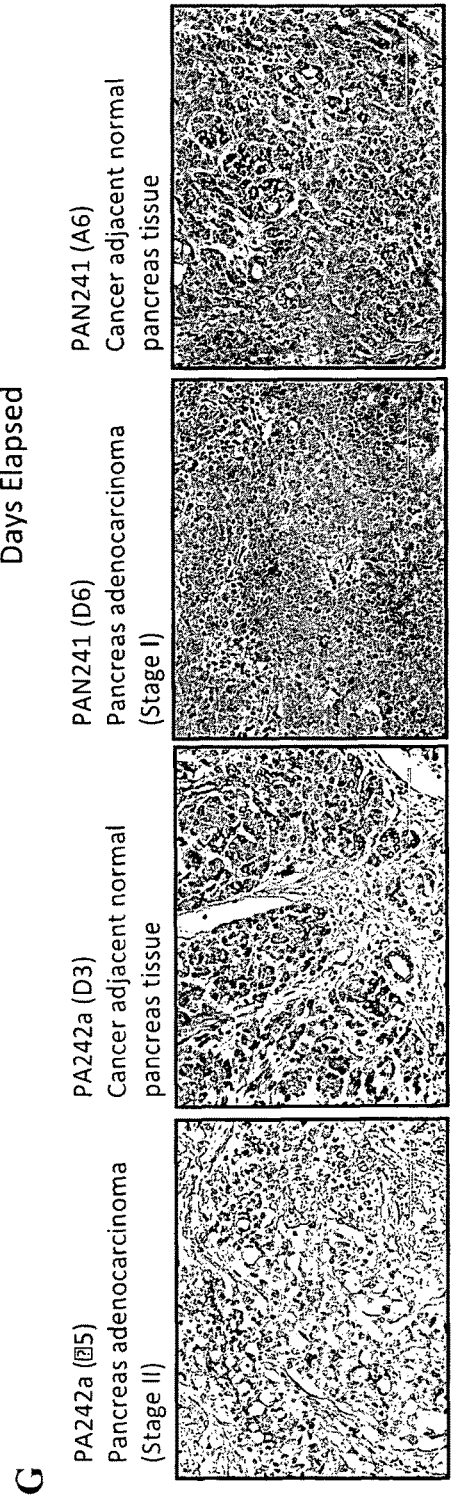
Figure 4:
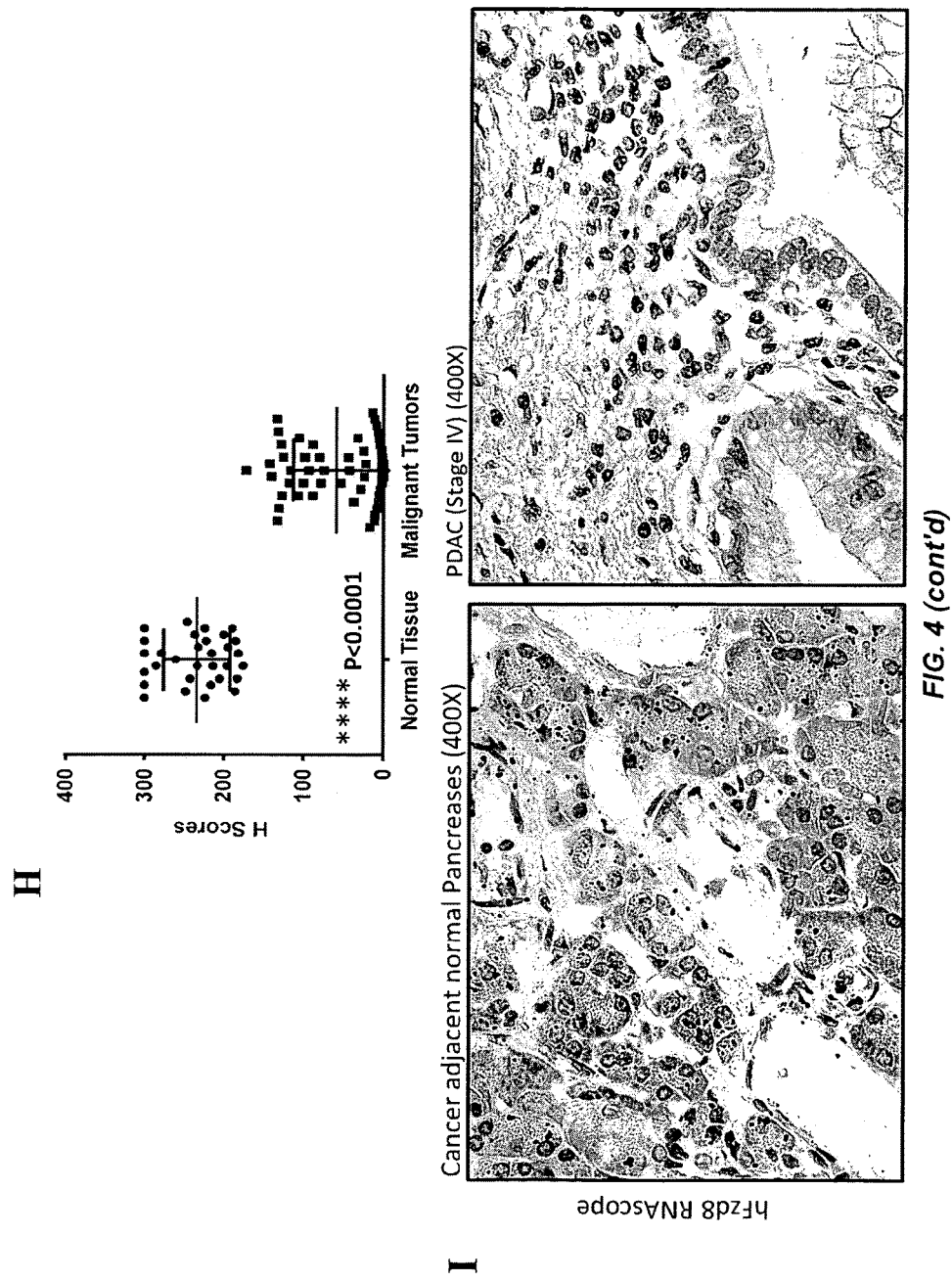

Next, we tested whether downregulation of Fzd8 is required for NIH/3T3-K-Ras$^{V12}$ cells to initiate tumor formation. Restoration of Fzd8 expression in NIH/3T3-K-Ras$^{V12}$ cells enhanced the levels of phosphorylated CaMKii, reduced cell growth, and reduced β-catenin activity (FIG. 4A-B). Furthermore, restoration of Fzd8 significantly reduced in vitro sphere forming efficiency in NIH/3T3-K-Ras$^{V12}$ cells, as well as their recapitulating ability after serial passage (FIG. 4C). Fzd8 over-expression completely abolished tumor formation in nude mice with subcutaneous injections of 50 NIH3T3-K-Ras$^{V12}$ cells, while control cells still maintained high tumor initiating rate in vivo (9/10) (FIG. 4D).

Figure 11:
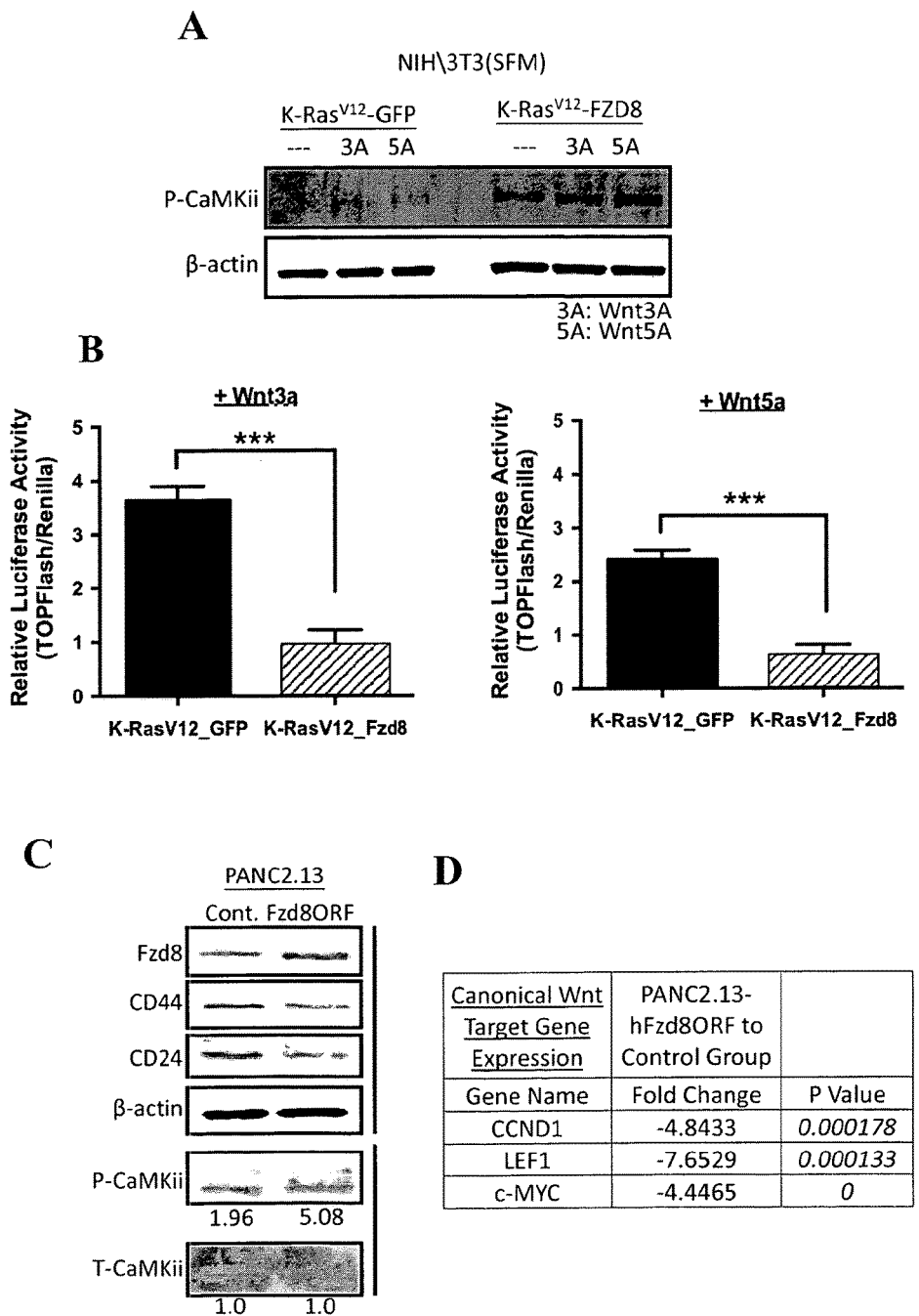
FIG. 11. (A) The presence of Wnt3a or Wnt5a did not affect the level of phosphor-CaMKii in NIH/3T3-K-Ras$^{V12}$ cells with or without Fzd8 overexpression. (B) TOPFlash assay in Fzd8 overexpressing NIH/3T3-K-Ras$^{V12}$ cells treated with Wnt3a or Wnt5a. GFP-vector expressing cells were used as control (N=3). (C-D) Restoration of Fzd8 in PANC2.13 cells reduced stem-ness signature and enhanced phosphorylation of CaMKii (C), and reduced the expression of target genes in canonical Wnt pathways (D) (N=3). (E) Overexpression of Fzd8 reduced the expression of CD44 and CD24 at mRNA in PANC1 cells (N=3). (F) Fzd8 restoration in PANC2.13 or PANC1 cells phenocopied K-Ras knockdown. (G) Micrographs of tissue sections immunostained for Fzd8 in human pancreatic normal and malignant tissues and in human pancreatic tumor tissues at different stages. (H) Oncomine analysis of human Fzd8 expression in different published data sets. * P<0.05;  P<0.01; * P<0.001.
Figure 11:
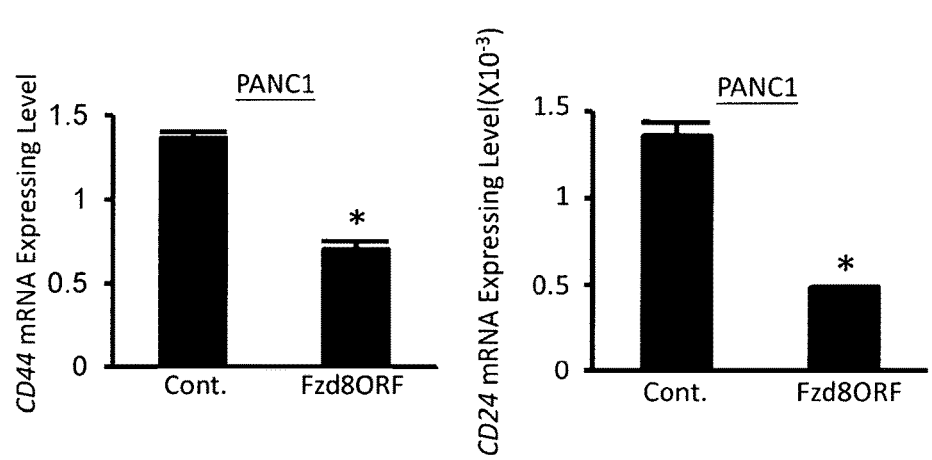
Figure 11:
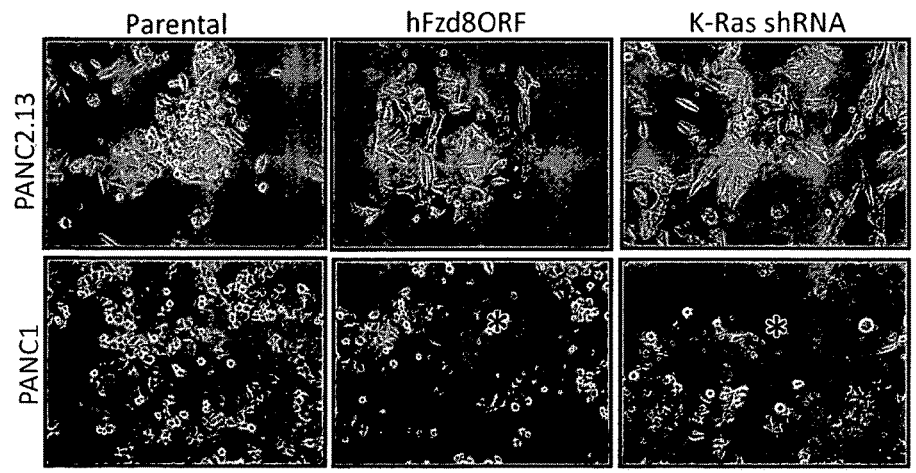
Figure 11:
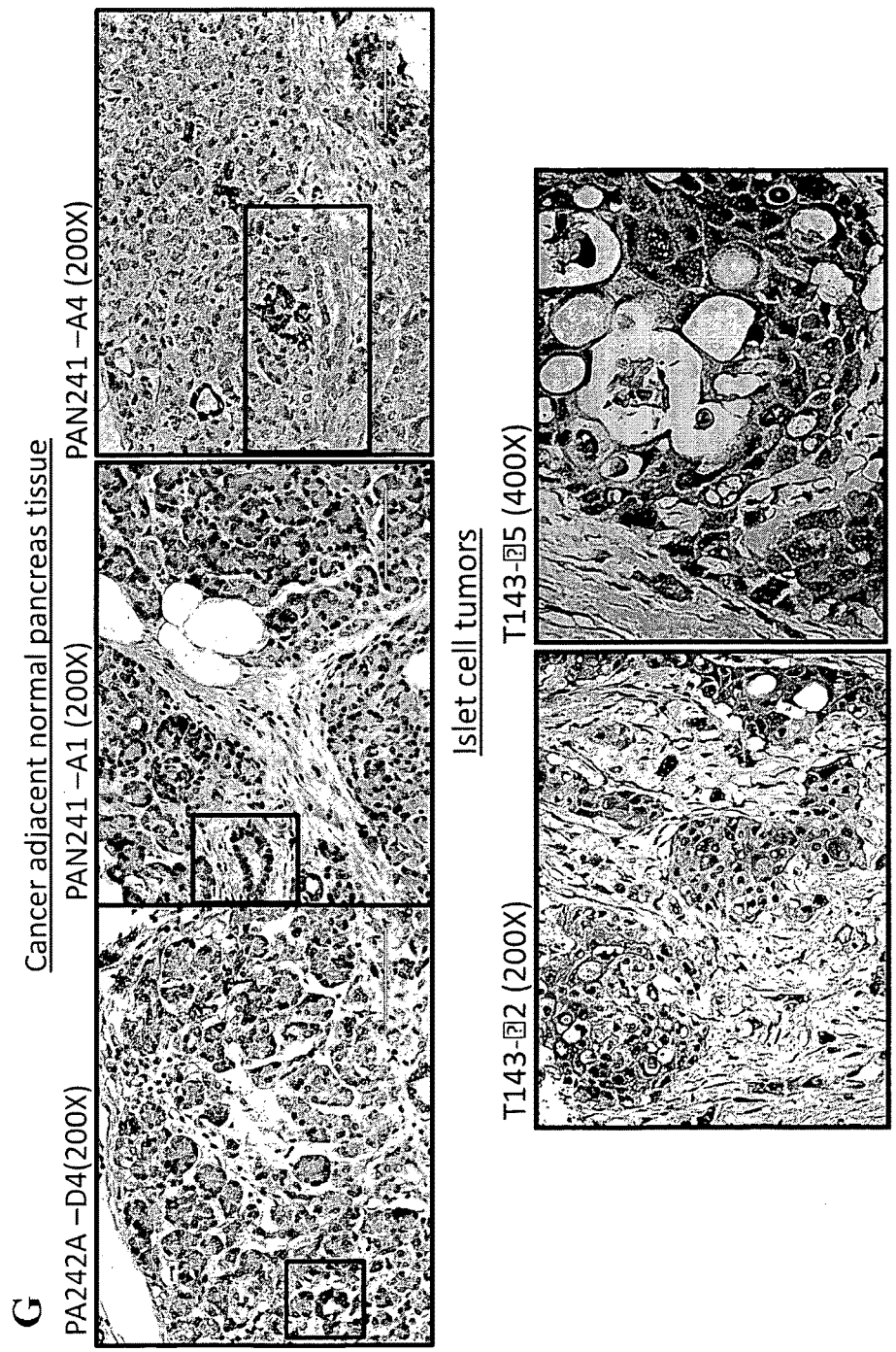
Figure 11:
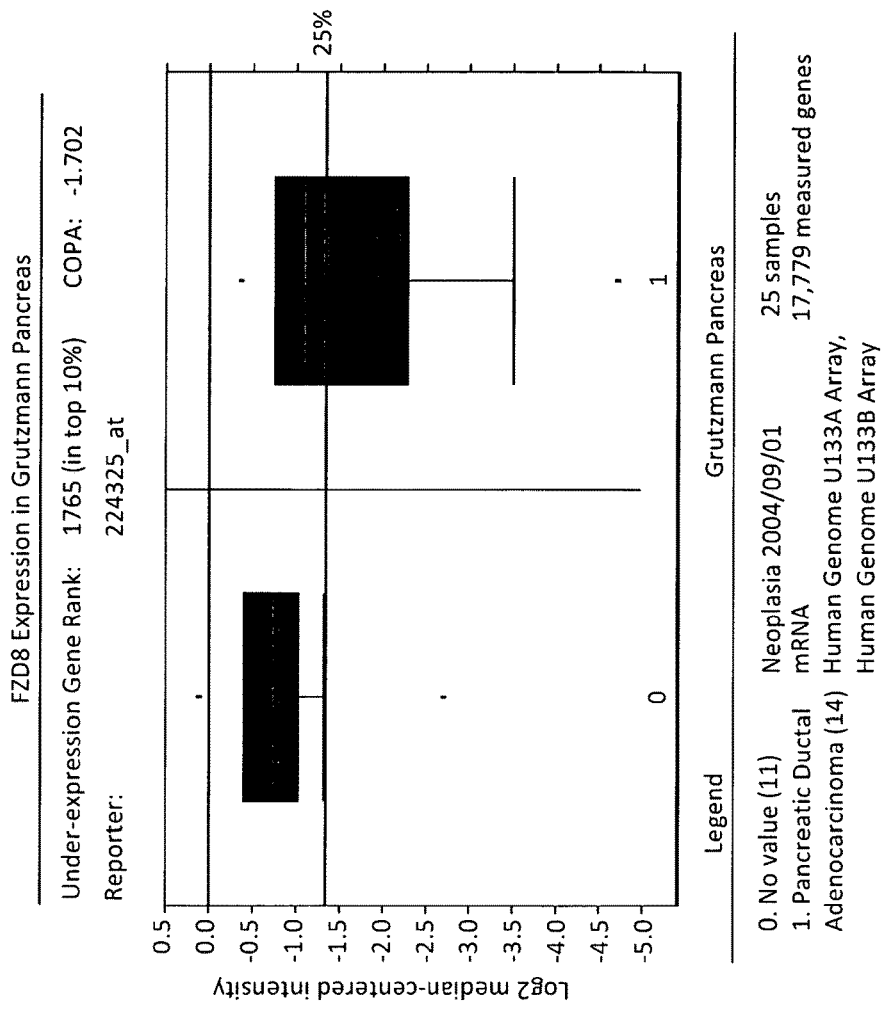
Figure 11:
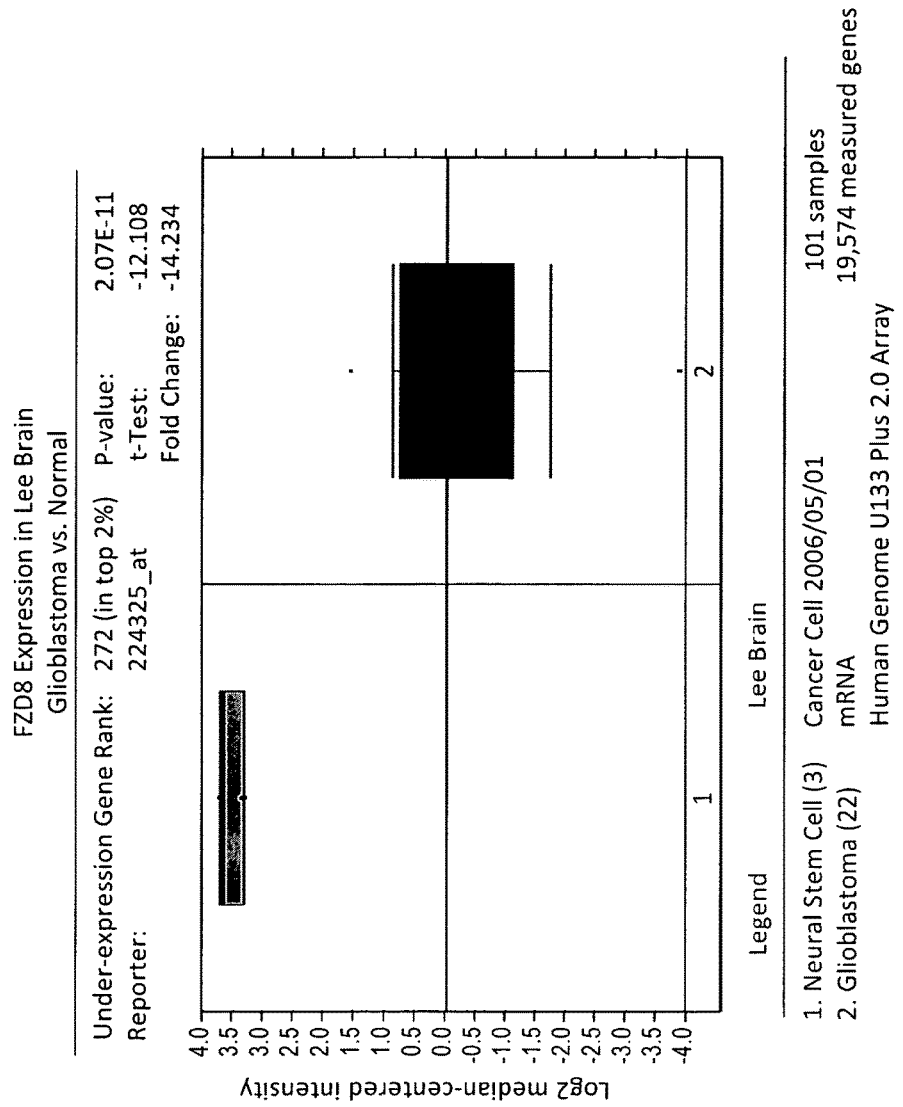
Figure 11:
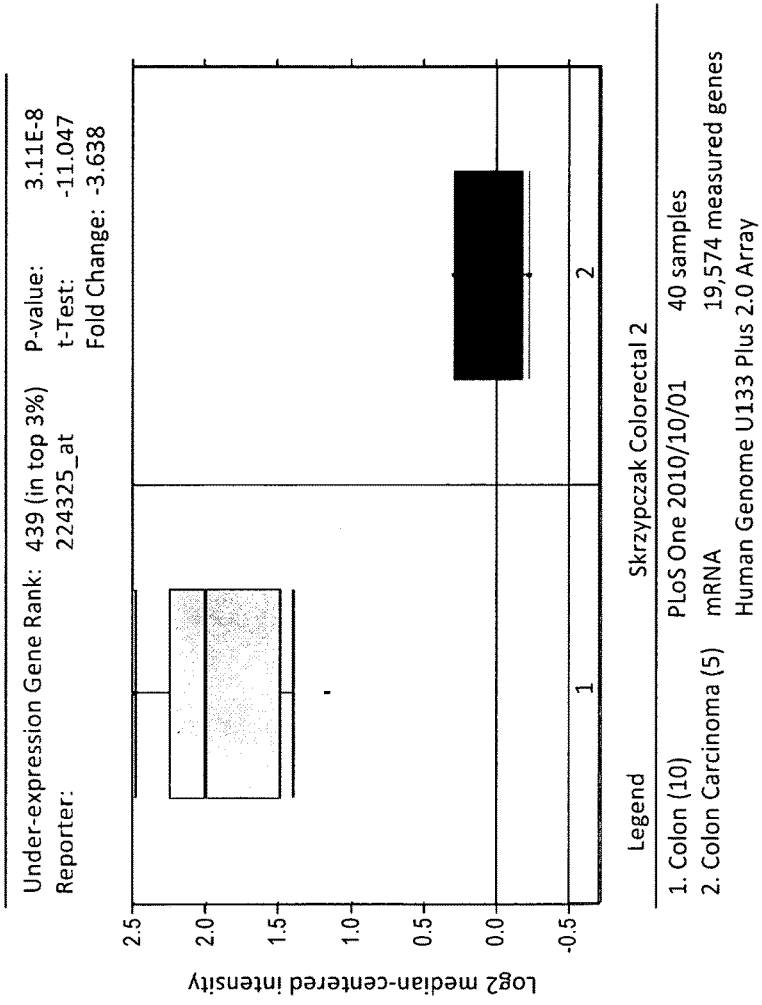

Interestingly, exogenously added WNT3a or WNT5a ligand did not affect the increased phospho-CaMKii and inhibited β-catenin activity caused by the over-expression of Fzd8 in NIH3T3-K-Ras$^{V12}$ cells (FIG. 11A-B). These data suggest that the altered Wnt/Ca$^{2+}$ signaling pathway and β-catenin activity in K-Ras$^{V12}$ transformed cells as results of Fzd8 overexpression cannot be rescued by canonical or non-canonical Wnt pathway ligands.

When Fzd8 was over-expressed in K-Ras-dependent human pancreas cancer PANC2.13 cells, we observed an increase in the levels of phospho-CaMKii, with a concurrent reduction in the expression of CD44 and CD24 (FIG. 11C). When compared with control cells, Fzd8-over-expressing PANC2.13 cells displayed significant down-regulation of multiple β-catenin targeted genes, including CCND-1, LEF1, and c-Myc, consistent with repressed β-catenin/TCF transcriptional activity (FIG. 11D). Over-expression of Fzd8 in PANC1 cells resulted in elevated NF-AT transcriptional activity, decreased activity of β-catenin, as assessed by luciferase reporter assays, and reduced expression of CD44 and CD24 (FIG. 4E and FIG. 11E). Interestingly, overexpression of Fzd8 in these pancreatic cancer lines induced differentiation-like morphological changes, pheno-copying those observed upon K-Ras knock-down (FIG. 11F). Furthermore, when compared with the control group, nude mice with subcutaneous xeno-transplants of PANC1 with over-expression of Fzd8 had increased tumor-free survival rates up to 90 days post-injections (FIG. 4F). The results establish that restoring Fzd8 expression, which enhances Wnt/Ca$^{2+}$ signaling and suppresses canonical Wnt signaling, reduces tumor formation by K-Ras$^{V12}$-transformed cells or pancreatic tumor cells possessing oncogenic K-Ras.

Human Fzd8 is normally expressed in brain, heart, kidney, skeletal muscle, as well as in the pancreas (Saitoh et al., *Int J Oncol* 18:991-996, 2001). However, expression patterns of Fzd8 during pancreatic tumor initiation and progression have not been investigated. Immunohistochemistry of four different human pancreatic tissue arrays (BioMax, PAN241, PA242a, PA483b and T143) revealed that while Fzd8 expression was abundant in normal pancreatic acini and islet cells, its expression was frequently lost in malignant pancreatic tissues (FIG. 4G and FIG. 11G). Interestingly, tissue array T143, B1, B2, B5 and B6 revealed that there was no evident reduction on Fzd8 expression in islet cell tumors, which are mostly benign and in which K-Ras is rarely mutated (FIG. 11G). In addition, Fzd8 expression was strongly repressed in stage I pancreatic adenocarcinomas (FIG. 4G), suggesting that the suppression of Fzd8 expression occurs at the early stages of pancreatic carcinogenesis where oncogenic activation of K-Ras has most likely already occurred. H-scoring further provided semi-quantitative analysis indicating Fzd8 was significantly repressed in human malignant pancreatic specimens when compared with normal tissues (FIG. 4H).

To further confirm the expression of Fzd8 in human pancreas tissues, we used RNAscope, a novel RNA in situ hybridization method. Single-molecule visualization in individual cells is achieved through use of a novel probe design strategy and a hybridization-based signal amplification system to simultaneously amplify signals and suppress background (Wang et al., *J. Mol Diagn* 14:22-29, 2012). As shown in FIG. 4I, normal pancreases and cancer adjacent normal tissues were hybridized with the probes specifically for human Fzd8 (Advanced Cell Diagnostics), whereas malignant pancreatic tissue showed no detection of Fzd8 expression in RNAcope in situ hybridization assay. In addition, Oncomine online software (Life Technologies), which allowed us to investigate human Fzd8 expression levels at RNA level across multiple published microarray data sets, suggested that Fzd8 was significantly down-regulated in not only human pancreatic ductal adenocarcinomas, but also multiple types of human cancers, including breast cancers, glioblastomas, and colon cancers (see, e.g., FIG. 11H).

Wnt/Ca2+ Signaling Modulated by K-Ras-CaM Interaction

Calmodulin (CaM), a calcium-binding messenger protein that activates CaMKii through direct binding, binds preferentially to GTP-bound K-Ras4B, but not to H-, N-, or K-Ras4A (Klee and Vanaman, *Adv Protein Chem* 35:213-321, 1982; Schulman, *Curr Opin Cell Biol* 5:247-253, 1993; Villalonga et al., *Mol Cell Biol* 21:7345-7354, 2001). This binding can change the subcellular localization of CaM and so reduce the pool of CaM available to activate CaMKii and subsequently the non-canonical Wnt/Ca$^{2+}$ signaling pathway. Therefore, we sought to determine whether the interaction between K-Ras and CaM is responsible the down-regulation of Wnt/Ca$^{2+}$ signaling by K-Ras.

Figure 5:
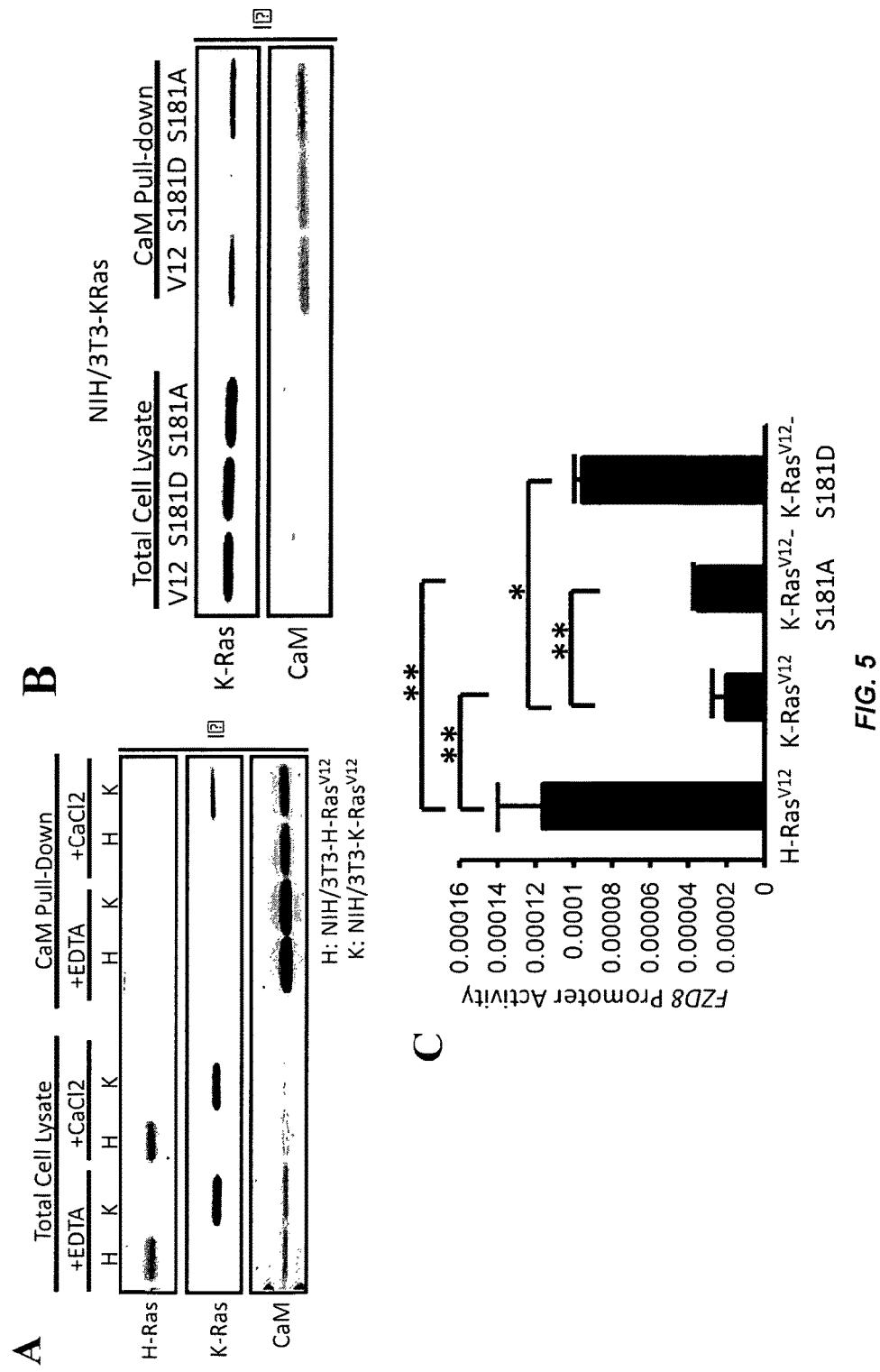
FIG. 5. Calmodulin (CaM)-K-Ras interaction is essential for suppression of calmodulin kinase II (CaMKii) activity and Fzd8 expression in K-Ras$^{V12}$-transformed NIH/3T3 cells. (A) Calmodulin interaction with K-Ras$^{V12}$, but not with H-Ras$^{V12}$, as revealed by CaM pull-down assay in the presence of EDTA or Ca$^{2+}$. (B) Loss of interaction between CaM with K-Ras$^{V12}$-S181D mutant when compared with K-Ras$^{V12}$ or K-Ras$^{V12}$-S181A mutant. (C) K-Ras$^{V12}$-S181D mutant presented reduced capability to suppress Fzd8 promoter activities when compared with K-Ras$^{V12}$ or K-Ras$^{V12}$-S181A mutant. (D) Increased Fzd8 expressions in NIH3T3-K-Ras$^{V12}$-S181D cells when compared with K-Ras$^{V12}$- or -S181A group at RNA level (N=3). (E) K-Ras$^{V12}$-S181D-expressing NIH/3T3 cells showed increased levels of Fzd8 expression and phospho-CaMKii when compared with NIH/3T3-K-Ras$^{V12}$ or -S181A cells. There was no significant difference in the levels of K-Ras protein and phosphor-Erk among three cell lines. (F) NIH/3T3-K-Ras$^{V12}$-S181D cells presented significantly increased NF-AT transcriptional activity (Left panel) and reduced Wnt/β-catenin activity (Right panel) when compared with K-Ras$^{V12}$-or-S181A group (N=4). (G) Schematic illustration of CaM-K-Ras interaction in K-Ras-mediated repression of Fzd8 expression and -promoted stem-ness through the Wnt/β-catenin signaling pathway. Prostratin is proposed to interfere the interaction through phosphorylation of K-Ras by the activation of PKC. (H) Calmodulin interaction with K-Ras$^{V12}$ was suppressed by the treatments of prostratin, as revealed by CaM pull-down assay. WCB: whole Cell Lysate. IB: immunoblotting. (I) Elevated activation of CaMKii by prostratin treatments in NIH/3T3 cells transformed by K-Ras$^{V12}$, not K-Ras$^{V12}$-S181A mutant or H-Ras$^{V12}$. (J) Cell morphologies of NIH/3T3 cells transformed by K-Ras$^{V12}$, K-Ras$^{V12}$-S181A mutant and H-Ras$^{V12}$ in the response to prostratin treatments. DMSO was used as the vehicle control. * $P<0.05$;  $P<0.01$; * $P<0.001$.
Figure 5:
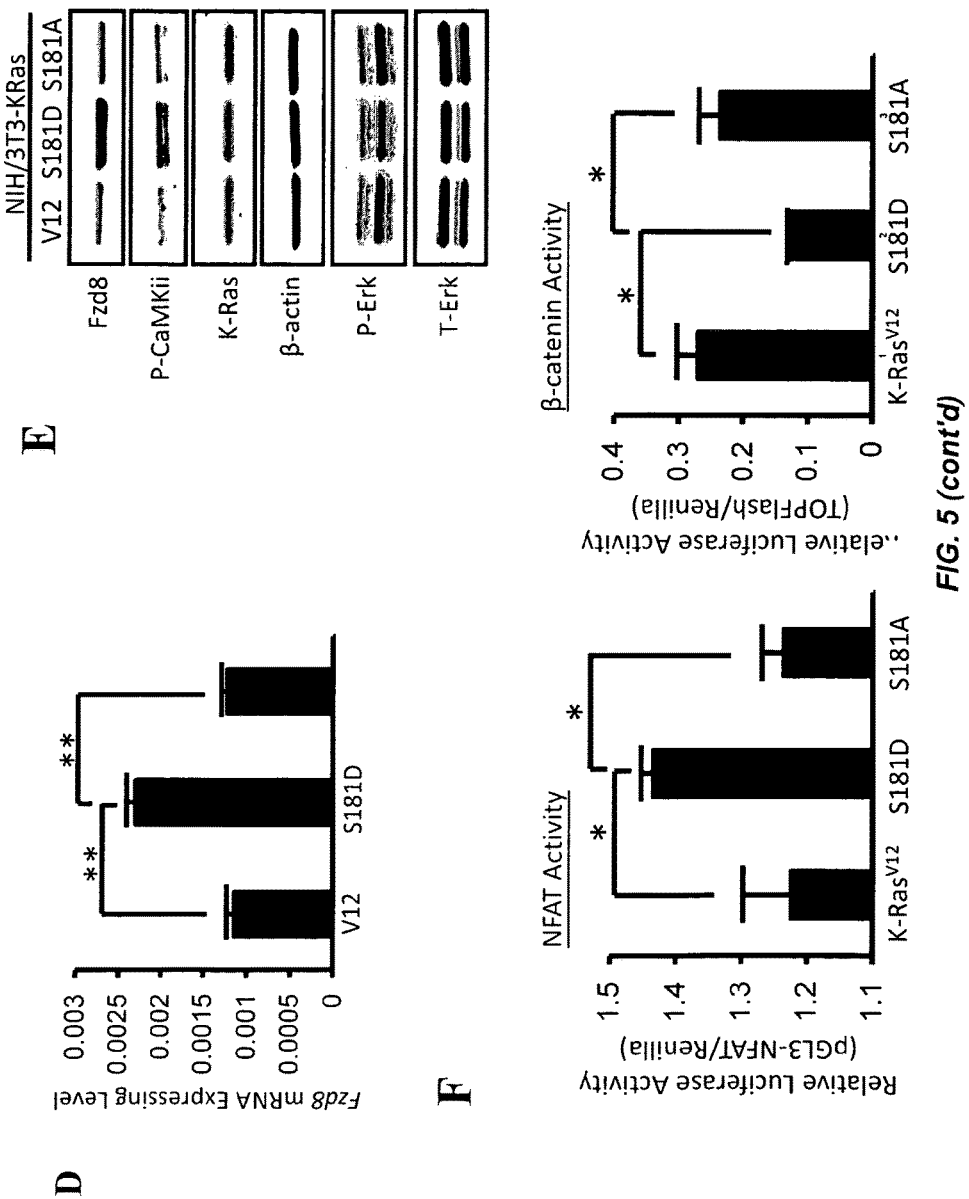
Figure 5:
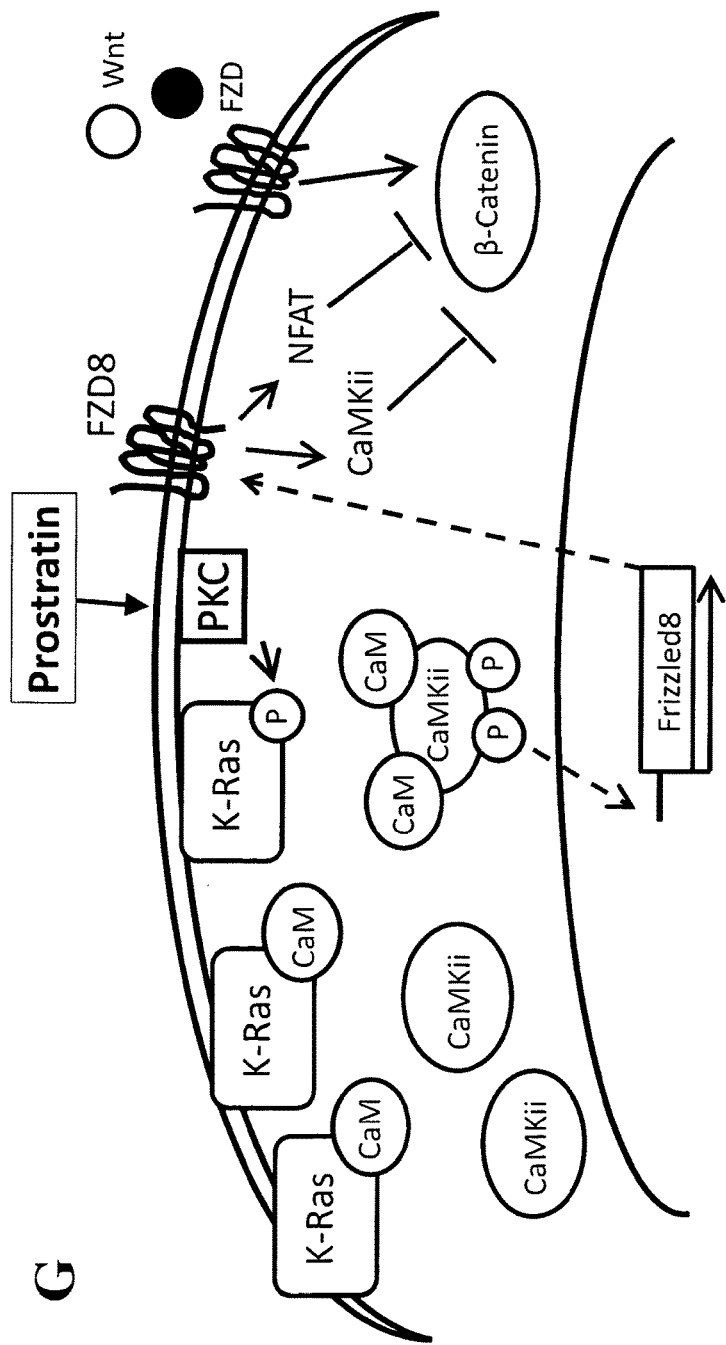
Figure 5:
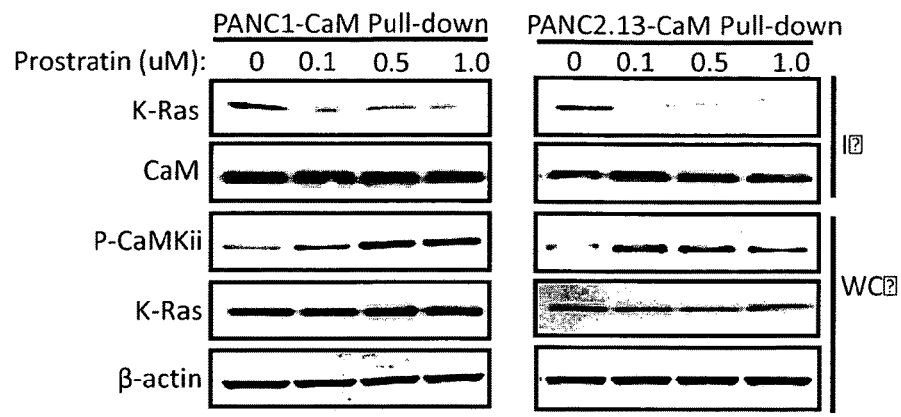
Figure 5:
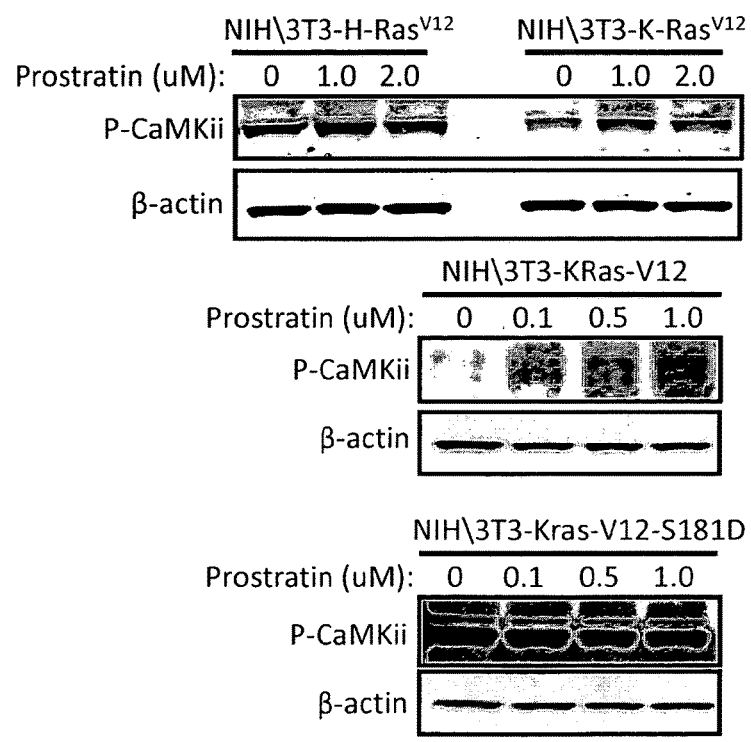
Figure 5:
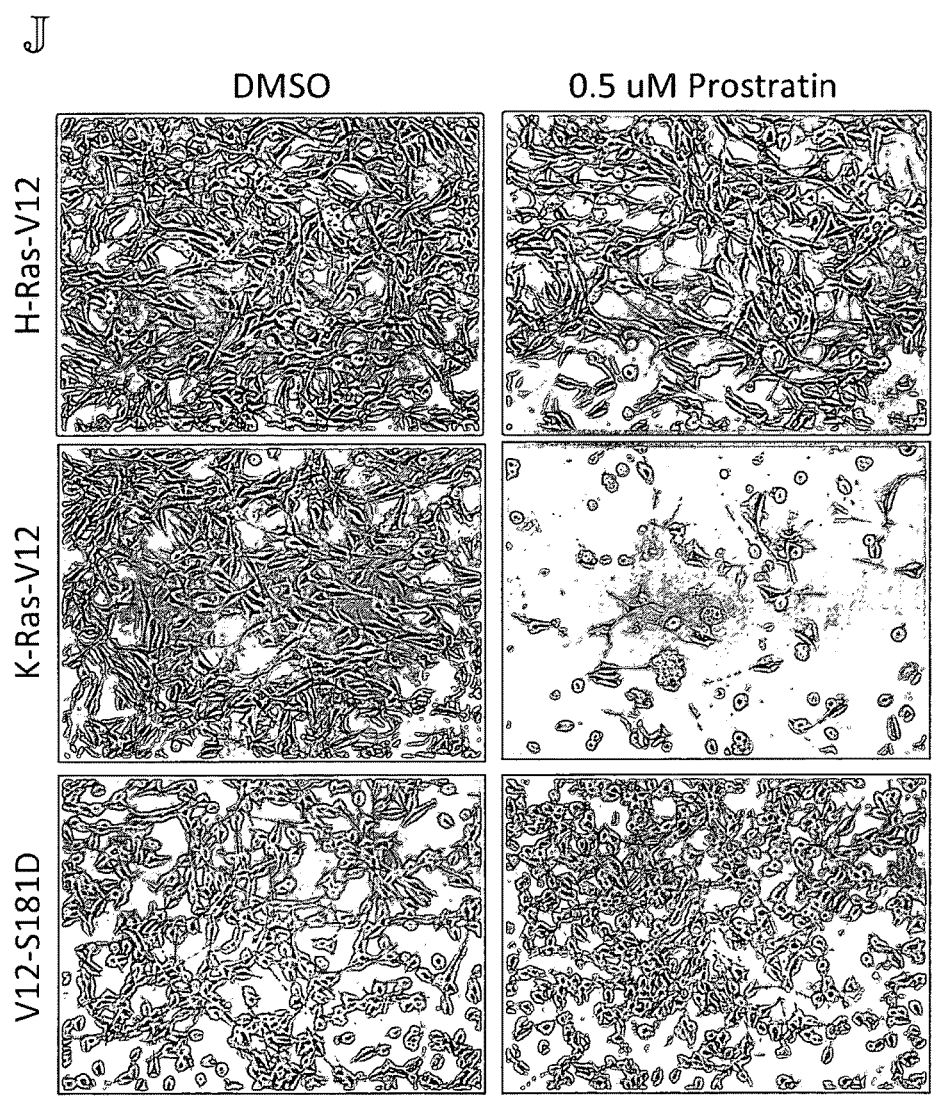
Figure 12:
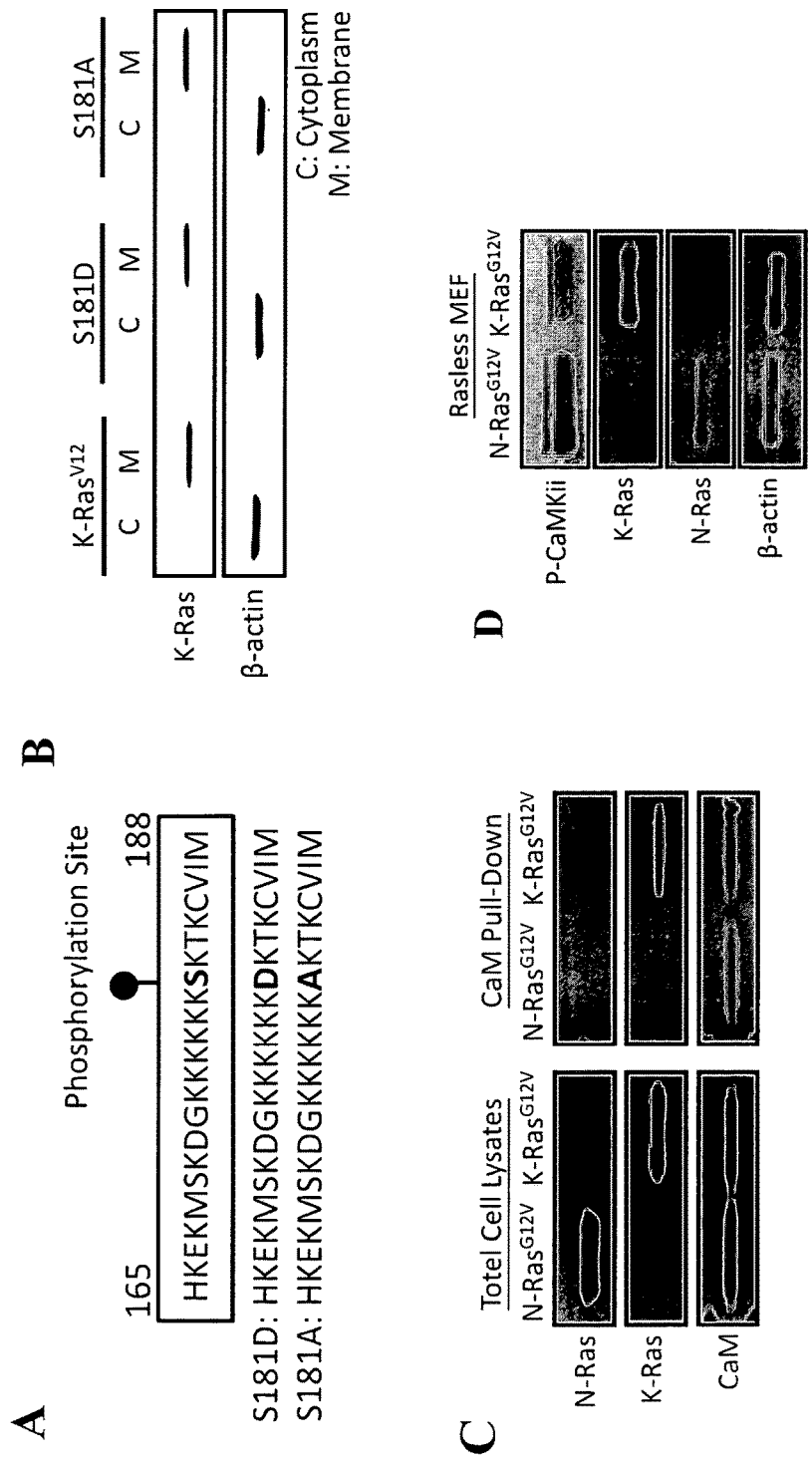
FIG. 12. (A) Schematic illustration of point mutation on K-Ras$^{V12}$ expression construct used for NIH/3T3 transformation (SEQ ID NOS:1-3, respectively). (B) Membrane localization of K-Ras protein in NIH/3T3 cells with K-Ras$^{V12}$, -S181D, and -S181A expression. (C) Calmodulin interaction with K-Ras$^{V12}$, but not N-Ras$^{V12}$, as revealed by CaM pull-down assay in the presence of EDTA or Ca$^{2+}$. (D) Rasless MEF overexpressing N-Ras$^{G12V}$ showed higher level of phosphor-CaMKii than Rasless MEF-K-Ras$^{G12V}$. (E) N-Ras$^{G12V}$ enhanced Fzd8expression at mRNA in Rasless MEFs when compared to K-Ras$^{G12V}$ (N=3). (F) TOP-Flash assay in Rasless MEFs overexpressing N-Ras$^{G12V}$ or K-Ras$^{G12V}$ (N=4). **P<0.01.
Figure 12:
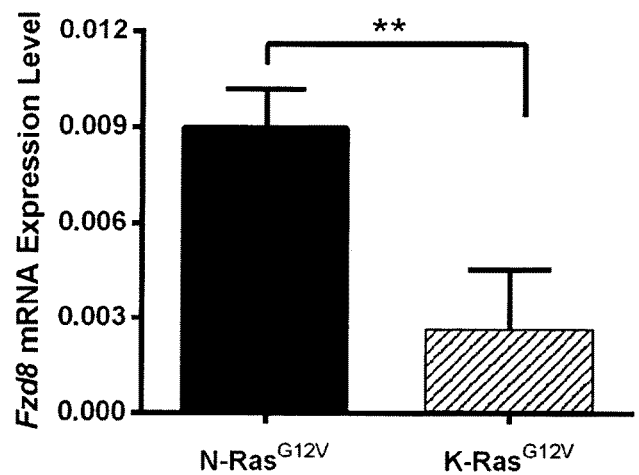
Figure 12:
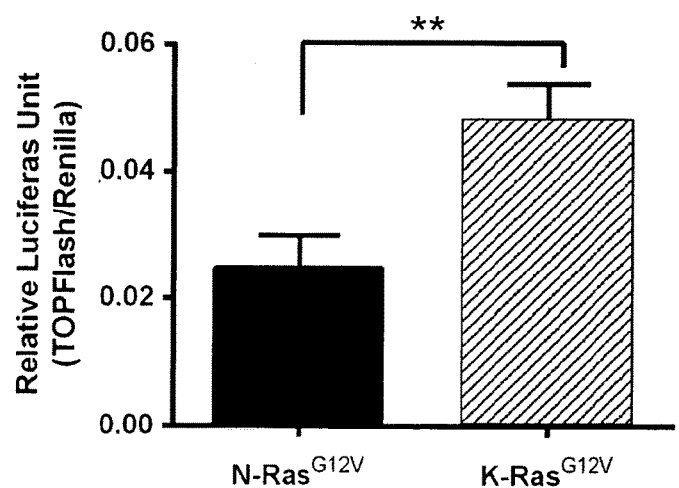

We first confirmed that K-Ras$^{V12}$, but not H-Ras$^{V12}$, binds to CaM, and does so in a calcium-dependent manner (FIG. 5A). The hypervariable region of K-Ras is essential for its interaction with CaM, and phosphorylation of Ser181 of K-Ras 4B abolishes this interaction (Lopez-Alcala et al., *J Biol Chem* 283:10621-10631, 2008; Villalonga et al., *Mol Cell Biol* 21:7345-7354, 2001). We generated retroviral constructs encoding either a mutant (S181D) that mimics phosphorylation, or mutant (S181A) form of K-Ras$^{V12}$ that cannot undergo phosphorylation, and then introduced these mutants into NIH/3T3 cells (FIG. 12A). The K-Ras$^{V12}$-S181D did not co-immunoprecipitate with CaM in NIH/3T3 cells, whereas wild-type and the S181A mutant maintained interaction with CaM under similar conditions (FIG. 5B). K-Ras$^{V12}$ mutants, S181D and S181A, are still farnesylated, transported to the plasma membrane correctly, and did not lead to morphological difference in NIH/3T3 cells when compared with K-Ras$^{V12}$ (FIG. 12B and data not shown). K-Ras$^{V12}$-S181D-expressing NIH/3T3 cells, with K-Ras-CaM interaction abolished and the levels of phospho-CaM-Kii increased, had marked increases in Fzd8 promoter activity and in the expression of Fzd8 at mRNA and protein levels in comparison with K-Ras$^{V12}$- or K-Ras$^{V12}$-S181A-transformed cells (FIG. 5C-E). Intriguingly, even though they exhibited comparable levels of K-Ras protein expression and phospho-Erk, K-Ras$^{V12}$-S181D-infected NIH/3T3 cells showed elevated levels of active CaMKii when compared with K-Ras$^{V12}$- or K-Ras$^{V12}$-S181A-transformed cells (FIG. 5E). K-Ras$^{V12}$-S181D-expressing cells further showed increased transcriptional activity of NF-AT, another major downstream mediator of Wnt/Ca$^{2+}$ signaling pathway, and repression of β-catenin transcriptional activity (FIG. 5F). These data show that K-Ras regulates the Fzd8-mediated non-canonical Wnt/Ca$^{2+}$ signaling and the sequential canonical Wnt signaling by specific interaction with calmodulin (FIG. 5G). In contrast, oncogenic H-Ras transformed tumor cells contain sufficient CaM to activate CaMKii, leading to activation of Wnt/Ca$^{2+}$ signaling and suppression of the Wnt/β-catenin signaling pathway (FIG. 5G). N-Ras, like H-Ras, is unable to bind to CaM (FIG. 12C). As a result, cells transformed by N-Ras resemble those transformed by H-Ras, including the phosphorylation of CaMKii, elevated expression of Fzd8, and decreased β-catenin/TCF/LEF transcriptional activity (FIG. 12D-F).

Taken together, these data suggest that disrupting the interaction between K-Ras and CaM by stimulating phosphorylation of S181 may be an attractive approach to suppress oncogenic K-Ras-driven malignancy.

Phosphorylation of K-Ras by Prostratin Compromises the Binding of K-Ras to CaM and Tumorigenicity Protein kinase C (PKC) is known to regulate K-Ras by phosphorylation of S181 within the polybasic region (Bivona et al., *Mol Cell* 21:481-483, 2006). While typical phorbol esters, such as phorbol-12-myristate-13-acetate (PMA), acting as PKC activators have shown to be tumor promoting, an atypical PKC activator, prostratin (12-Deoxyphorbol-13-Acetate), is far less potent for tumor promotion (Szallasi et al., *Nat Genet* 40:1240-1244, 1993; Zayed et al., *Planta Med* 50:65-69, 1984). Prostratin has recently been proposed as a novel therapeutic agent for treating AIDS, as it reactivates HIV-1 in memory CD4+ T cells that harbor latent proviruses, while down-regulating the CD4 receptor, precluding new HIV infections. (Hezareh, *Drug News Prespect* 18:496-500, 2005; Williams et al., *J Biol Chem* 279: 42008-42017, 2004; Witvrouw et al., *Antivir Chem Chemother* 14:321-328, 2003). Here, we determined whether this non-tumor promoting PKC activator could be repurposed as a novel agent to reduce K-Ras mediated malignancy.

Figure 13:
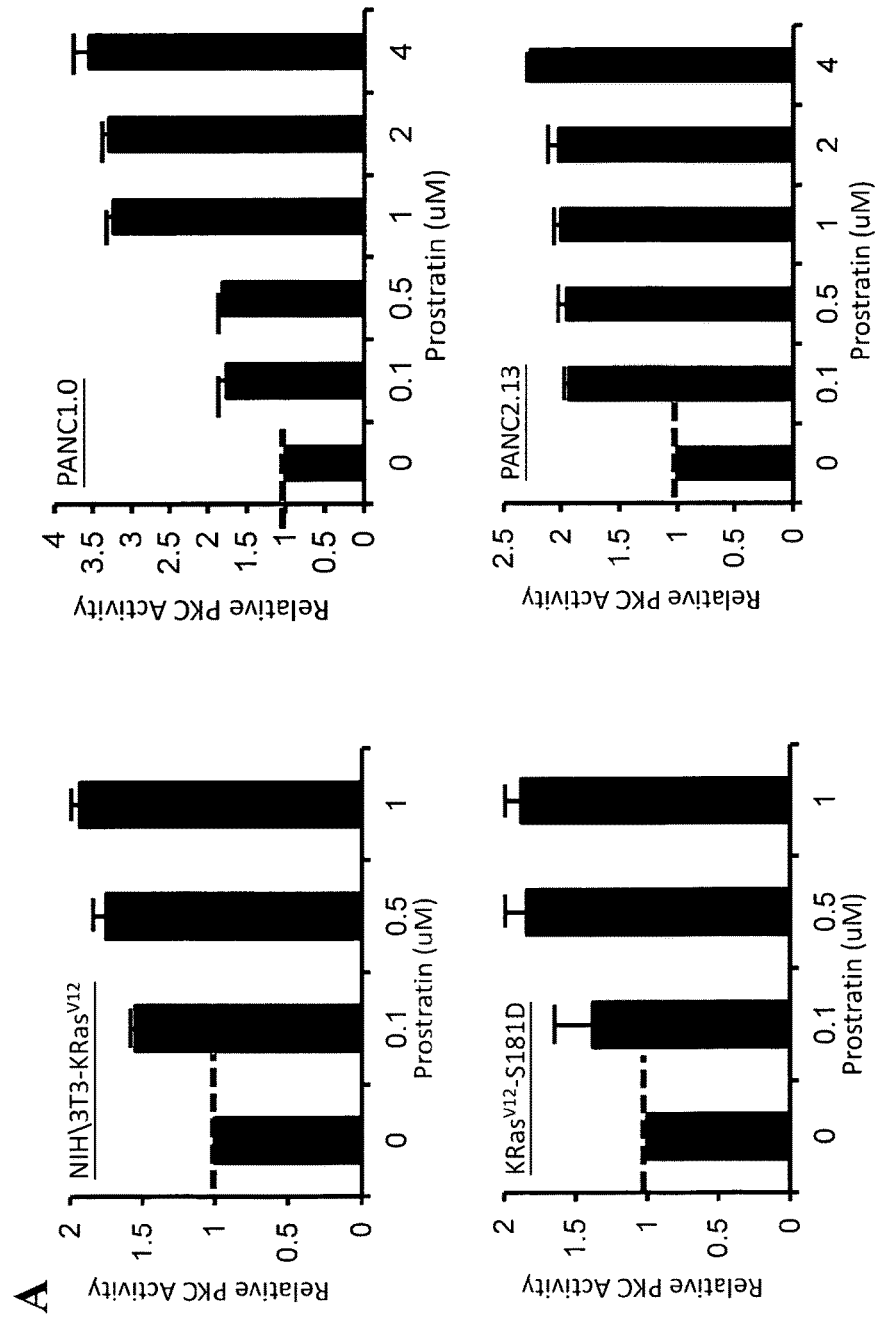
FIG. 13. (A) Relative PKC activity normalized by DMSO treated group in multiple cell lines in the response to prostratin (N=3). (B) Fzd8 and LEF1 mRNA expression levels in PANC1 and PANC2.13 with prostratin treatments at different dosages (N=3). (C) Prostratin increased the phosphorylation level of CaMKii and decreased the cell viability rate in Rasless MEFs overexpressing K-Ras$^{G12V}$, but not H-Ras$^{G12V}$ (N=6 for cell viability assay). (D) (Left panel) Prostratin decreased tumor initiation rate of K-Ras$^{V12}$-transformed NIH/3T3 cells, but not of H-Ras$^{V12}$-transformed cells, in nude mice via i.p. injection or oral gavage. (Right panel) The body weight changes indicated that prostratin treatment had no systematically toxic effects in animals. (E) Prostratin increased the phosphorylation level of CaMKii in the tumors derived from NIH/3T3 cells transformed by K-Ras$^{V12}$. (F) PKC activity in serum or pancreases of athymic NUDE mice harvested at different time points post-prostratin treatment. * P<0.05; **P<0.01.
Figure 13:
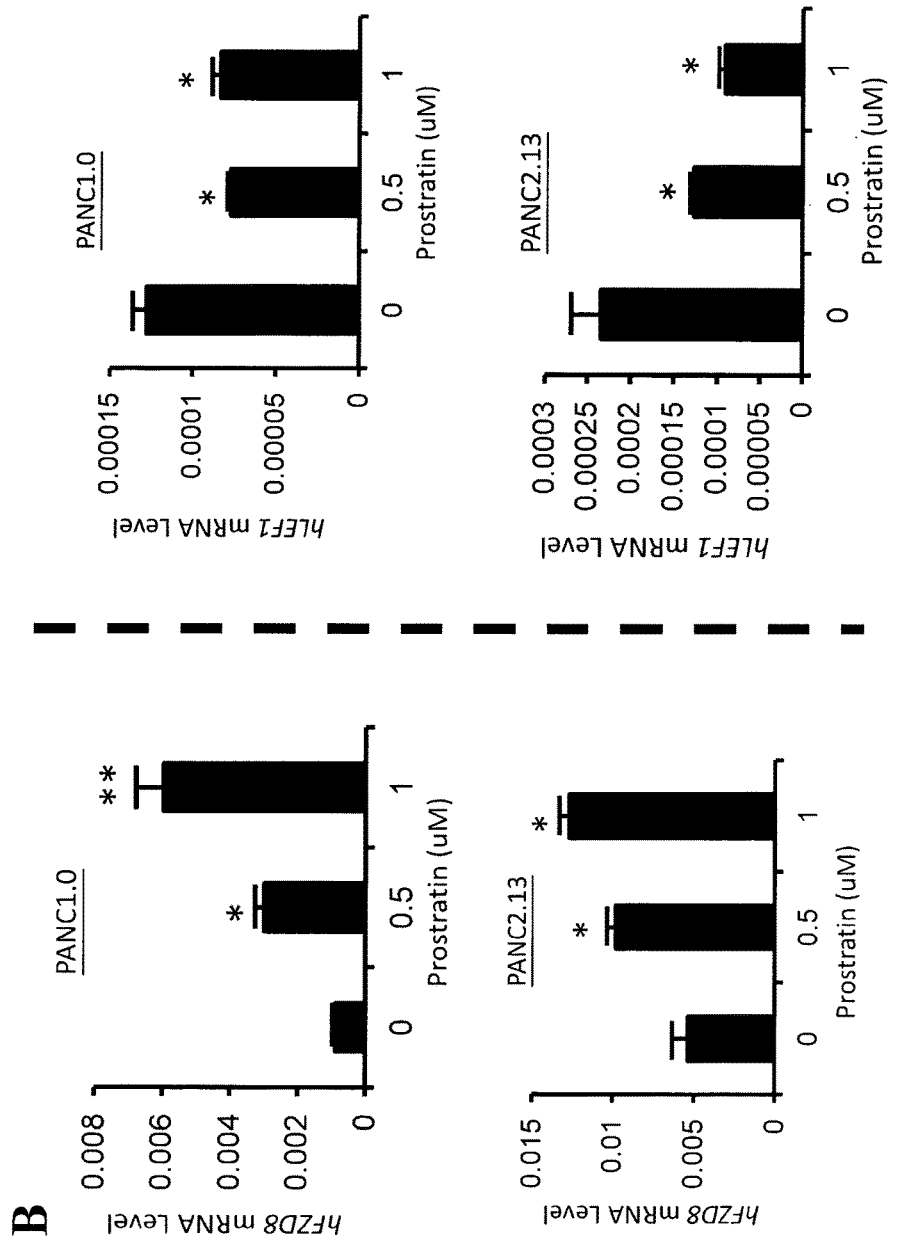
Figure 13:
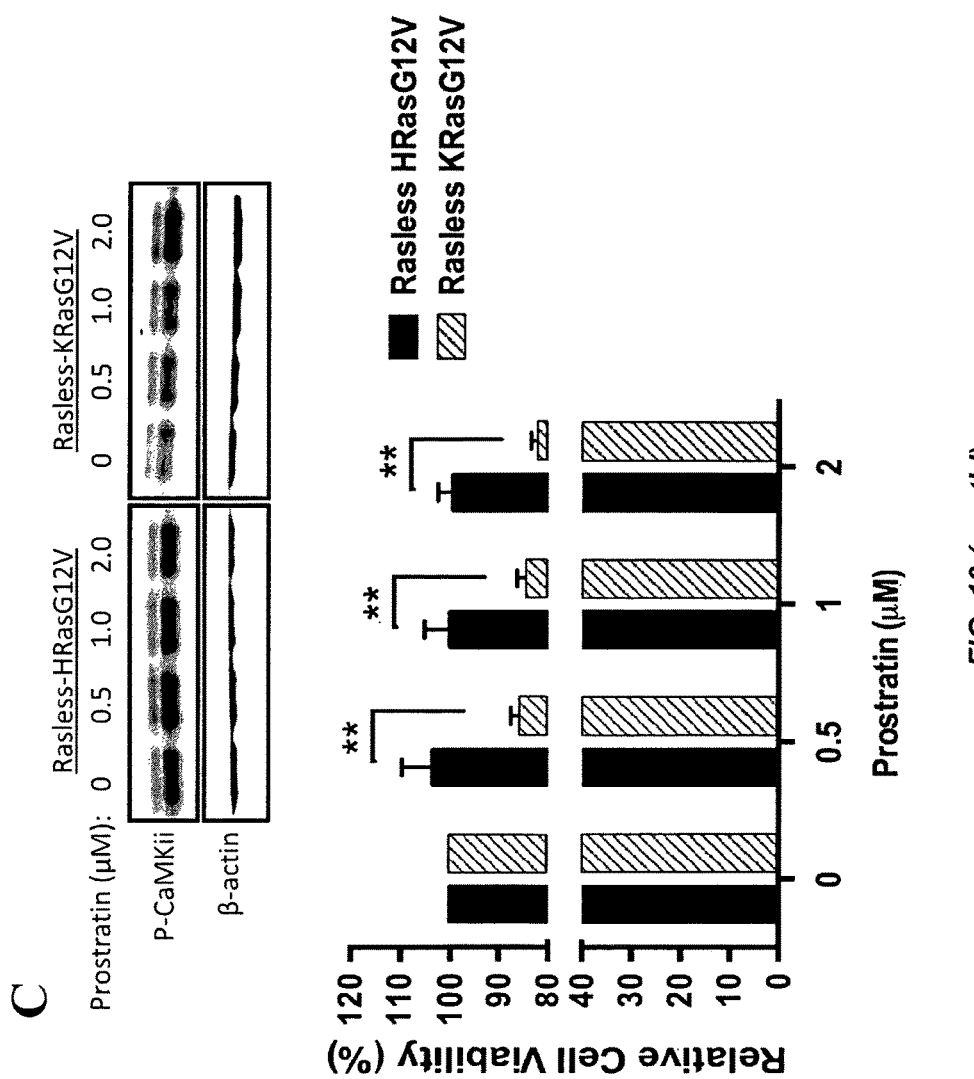
Figure 13:
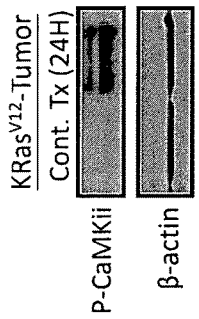
Figure 13:
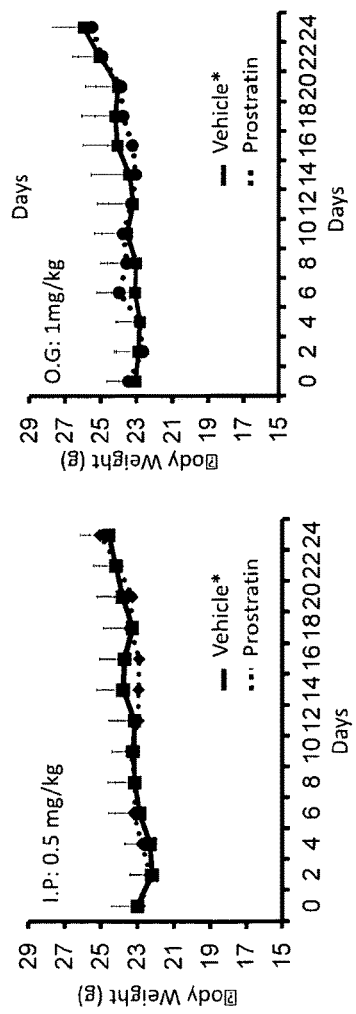
Figure 13:
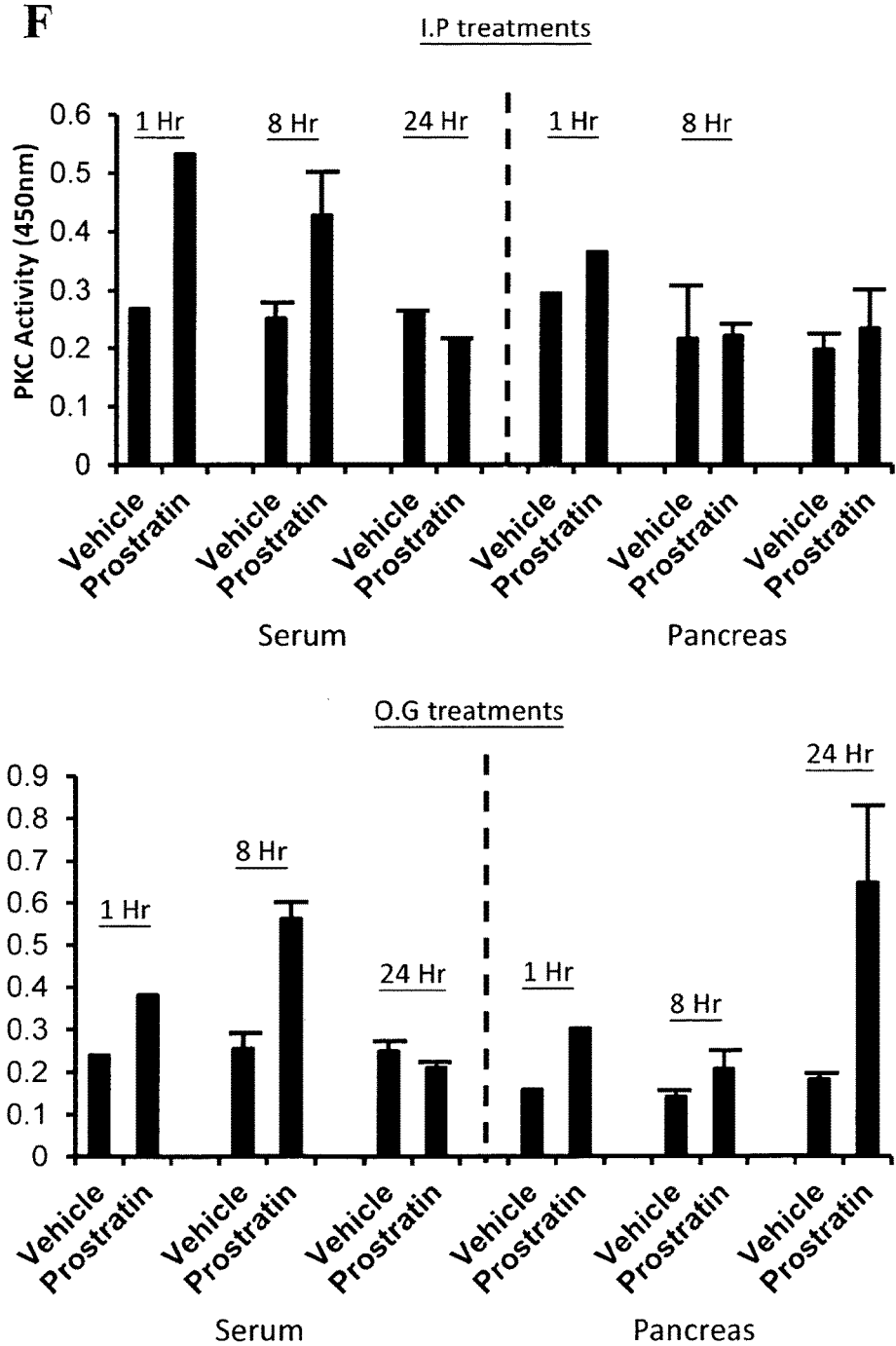

Prostratin, which activates PKC in a dose-dependent manner (FIG. 13A), abolished the endogenous interaction between K-Ras and CaM in Ras$^{V12}$-transformed cells and multiple human pancreatic cancer cell lines (FIG. 5H). The cells subsequently showed dramatically elevated levels of phospho-CaMKii in response to prostratin (FIG. 5H-I). Furthermore, treatment with prostratin increased expression of Fzd8 and reduced the expressions of β-catenin targeted gene, LEF1 in human pancreatic cancer cells, further suggesting that activation of PKC by prostratin changed the activity of downstream Wnt/Ca$^{2+}$ signaling mediated by oncogenic-K-Ras (FIG. 13B). Of note, treatment with prostratin did not alter the activity of CaMKii in cells transformed by H-Ras$^{V12}$ or K-Ras$^{V12}$-S181D, which have no CaM-binding capacity (FIG. 5I). Moreover, K-Ras$^{V12}$, but not H-Ras$^{V12}$ or K-Ras$^{V12}$-S181D, -transformed NIH/3T3 cells, were sensitive to prostratin and showed dramatically reduced cell viability (FIG. 5J). Furthermore, we showed that H-Ras$^{V12}$ and K-Ras$^{V12}$ mediated the expression of Fzd8 and sequential Wnt/Ca2+ signaling divergently in rescued "Rasless" MEFs. Likewise, Rasless MEFs rescued with-K-Ras(4B)$^{V12}$ showed increased phospho-CaMKii and decreased cell viability upon treatment with prostratin, while Rasless MEFs rescued with H-Ras$^{V12}$ showed minimal responses to prostratin (FIG. 13C). These dramatic in vitro responses led to ask whether prostratin could serve as a novel agent to treat K-Ras-driven malignancies?

Interestingly, prostratin administered either orally or intra-peritoneally dramatically suppressed the tumorigenicity of K-Ras$^{V12}$-transformed cells with no evidence of systemic toxicity (FIG. 13D). A single subcutaneous tumor derived from K-Ras$^{V12}$-NIH/3T3 cells in the presence of prostratin was much smaller and showed greatly increased phosphor-CaMKii when compared to those treated with vehicle control (FIG. 13D-E).

Prostratin Suppresses Tumor Initiation and Growth of Human Pancreatic Cancers

Figure 14:
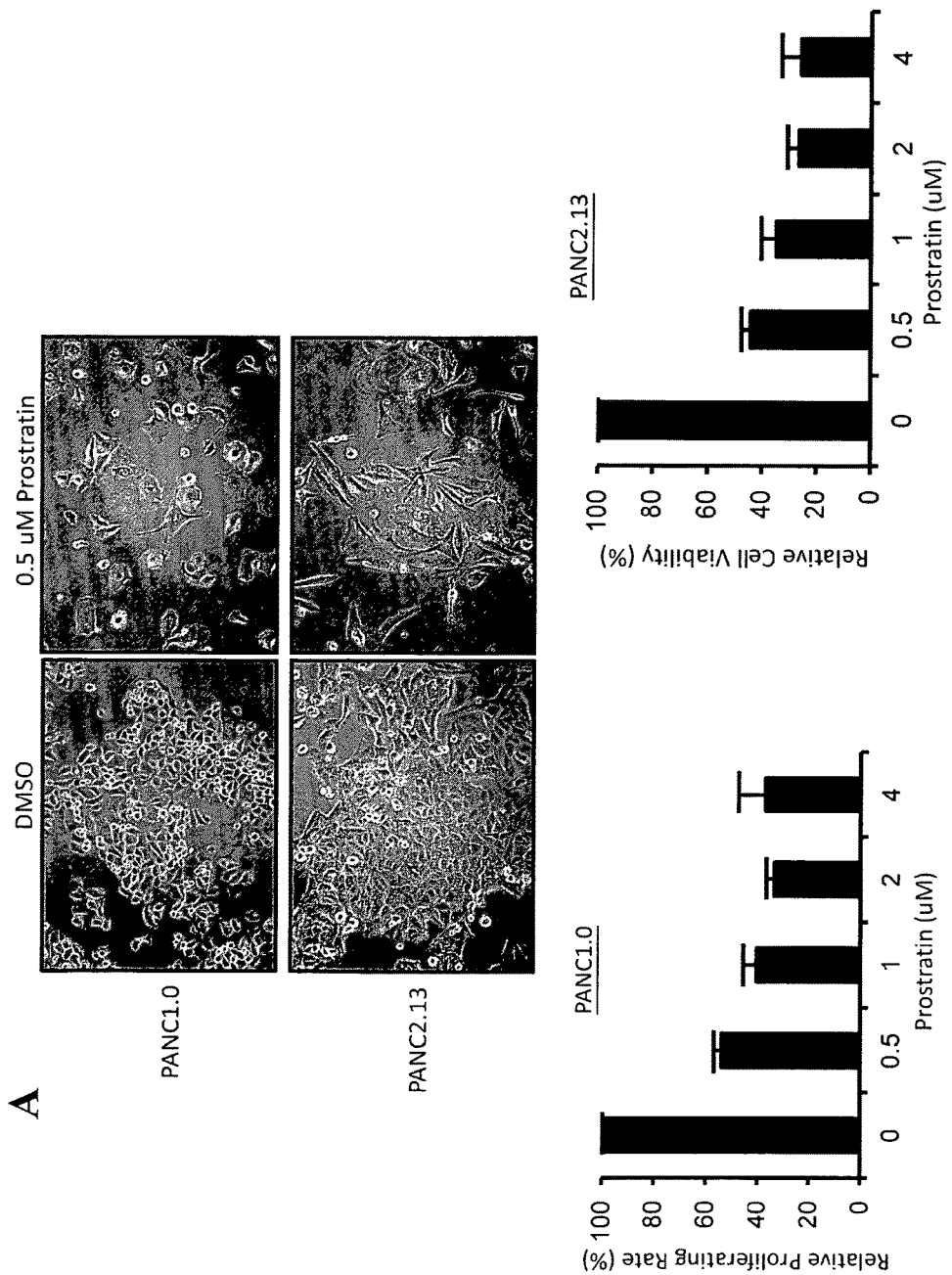
FIG. 14. (A) (Left panel) Cell morphologies in PANC1 and PANC2.13 with prostratin treatments. (Right panel) Relative cell viability or proliferating rate of PANC1 and PANC2.13 with prostratin treatments (N=6). (B) (Left panel) Tumor initiation rate of orthotopic injected PANC1. (Right panel) H&E and Ki67 staining of orthotopic tumors derived from PANC1. (C) Photos to compare the peritoneum of NOD SCID mice bearing the orthotopic injections of PANC2.13 with either vehicle or prostratin treatments. (D) The established tumors from PANC2.13 showed increased cleaved caspase 3 in response to daily prostratin treatment. (E) Papillomas derived from K-Ras$^{G12V}$ showed dramatically decreased tumor proliferation rate when compared to vehicle treated tumors.
Figure 14:
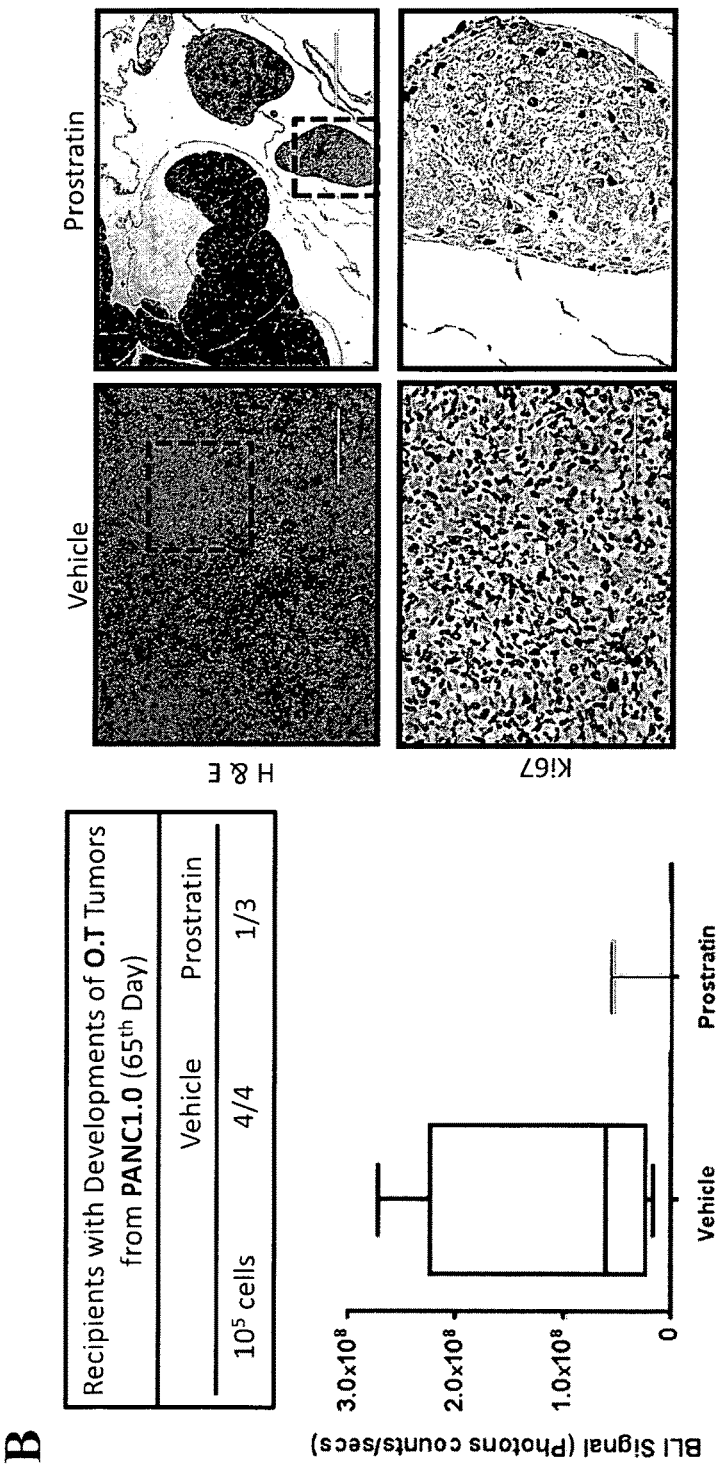
Figure 14:
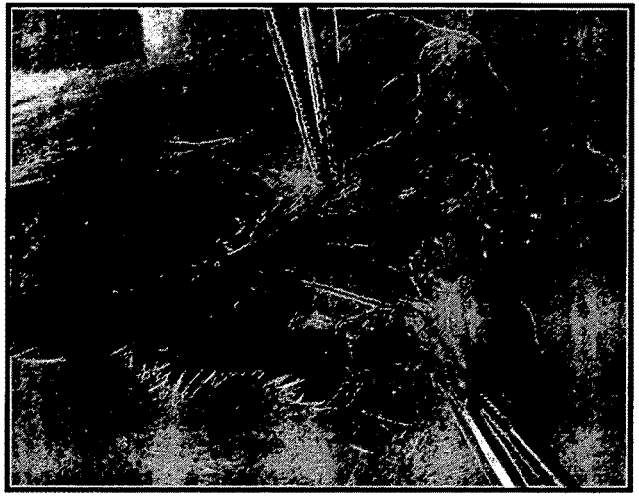
Figure 14:
Figure 14:
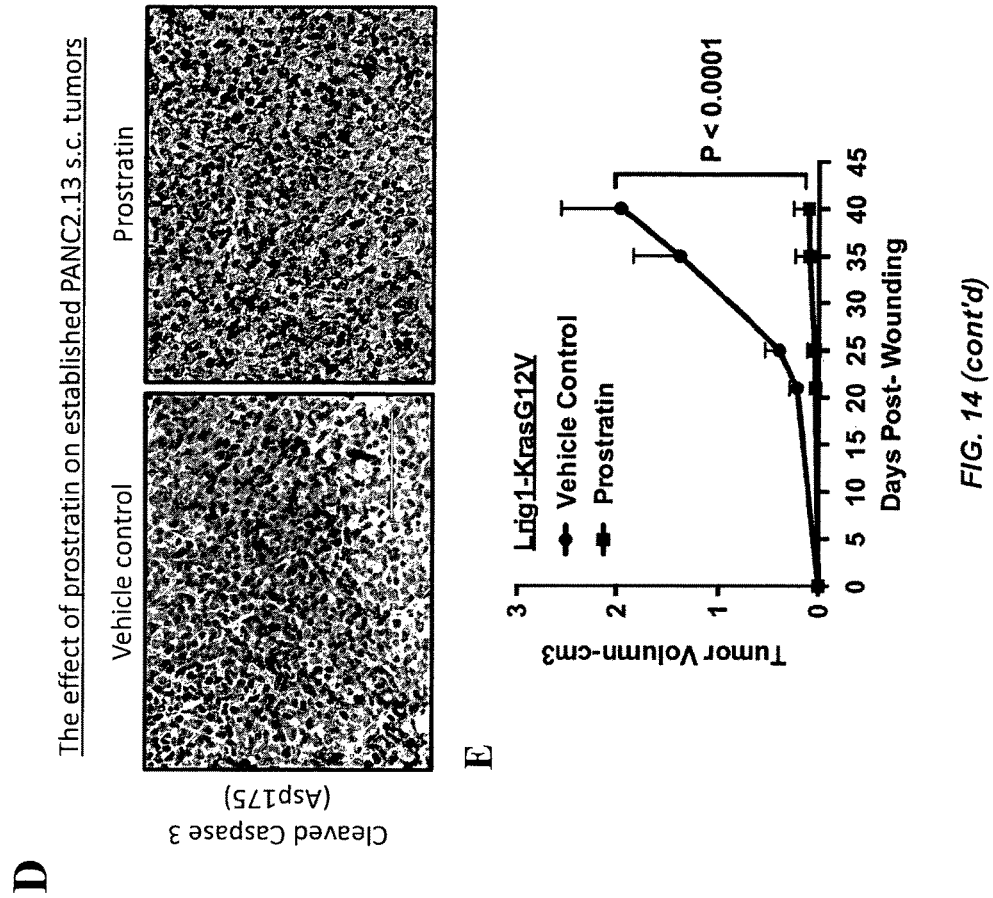

In response to prostratin treatments, human pancreatic cancer cell lines possessing different isoforms of mutant K-Ras expressed cell morphological changes phenocopying those observed with knock-down of K-Ras or over-expression of Fzd8 (FIG. 14A, left panel). Moreover, treatment of prostratin significantly reduced cell viability and the proliferating rate of human pancreatic cancer cells (FIG. 14A, right panel).

Figure 6:
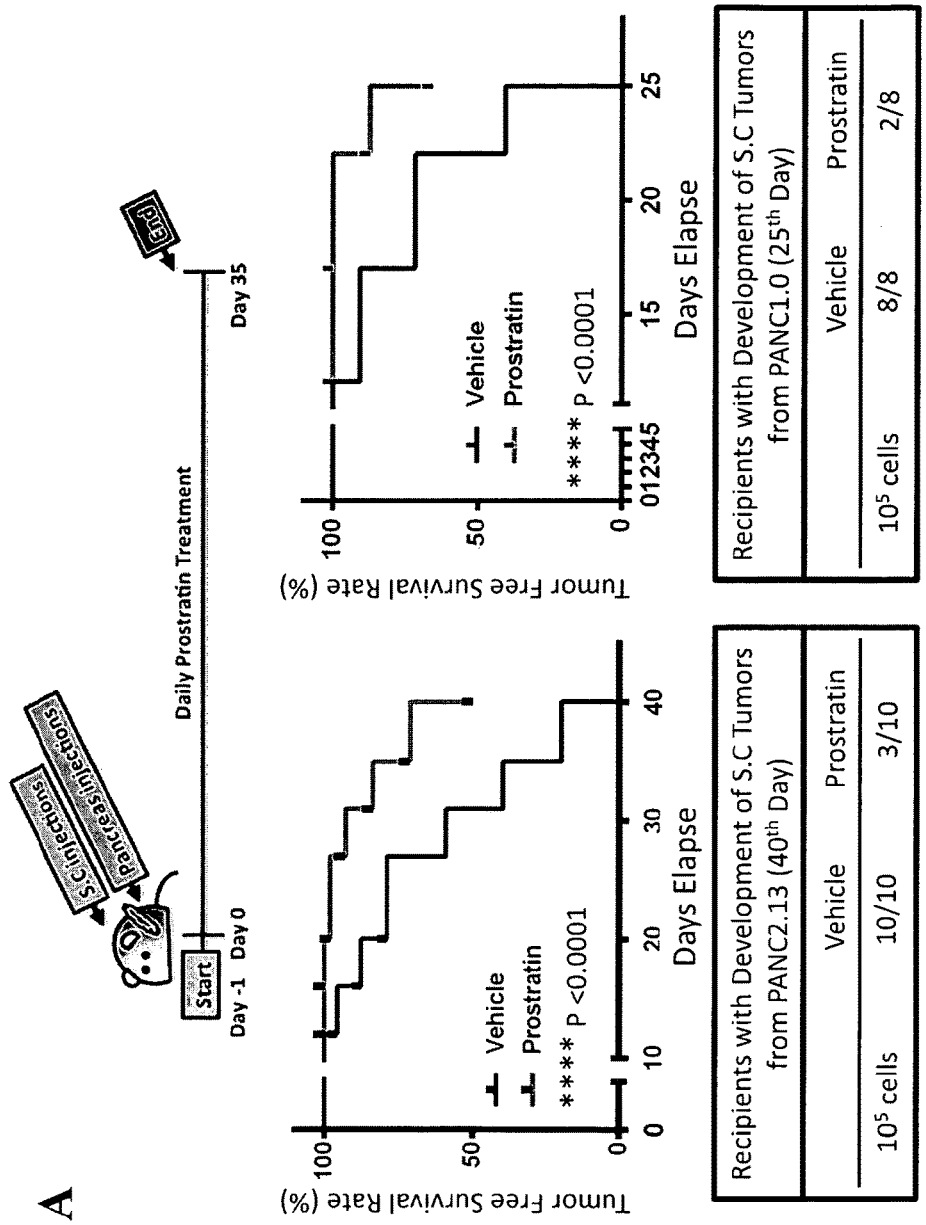
FIG. 6. Prostratin prevented the tumor initiations of human pancreatic cancers with mutant K-Ras. (A) Tumor initiation rates of subcutaneously injected PANC1 and PANC2.13 in the response to either vehicle or prostratin treatments. Top panel: schematic illustration of experimental design. Oral prostratin administration was given one day before tumor implantation. Nude mice were used for subcutaneous injections, and SCID mice were used for orthotopic implantation. (B) Tumor growth curve of the subcutaneous tumors derived from PANC2.13 in the response to drug treatments (N=10). (C) Bioluminescence imaging (BLI) signaling changes of the subcutaneous tumors derived from PANC2.13 in the response to drug treatments (N=10). (D) Tumor proliferation rate and Ki67 staining of the subcutaneous tumors derived from PANC2.13 in the response to drug treatments. Tumor proliferation rate (D27-36)=(Size of tumor on D36–Size of tumor on D27)/Size of tumor on D36*100. (E) Tumor initiation rate and BLI signaling activity of the orthotopic tumors derived from PANC2.13 in the response to drug treatments. (F) H &E staining of normal mouse pancreases and orthotopic tumors derived from PANC2.13. (G) Ki67 staining of orthotopic tumors derived from PANC2.13 in the response to drug treatments. * $P<0.05$;  $P<0.01$; * $P<0.001$; **** $P<0.0001$. Data are means±SEM for (B) & (C).
Figure 6:
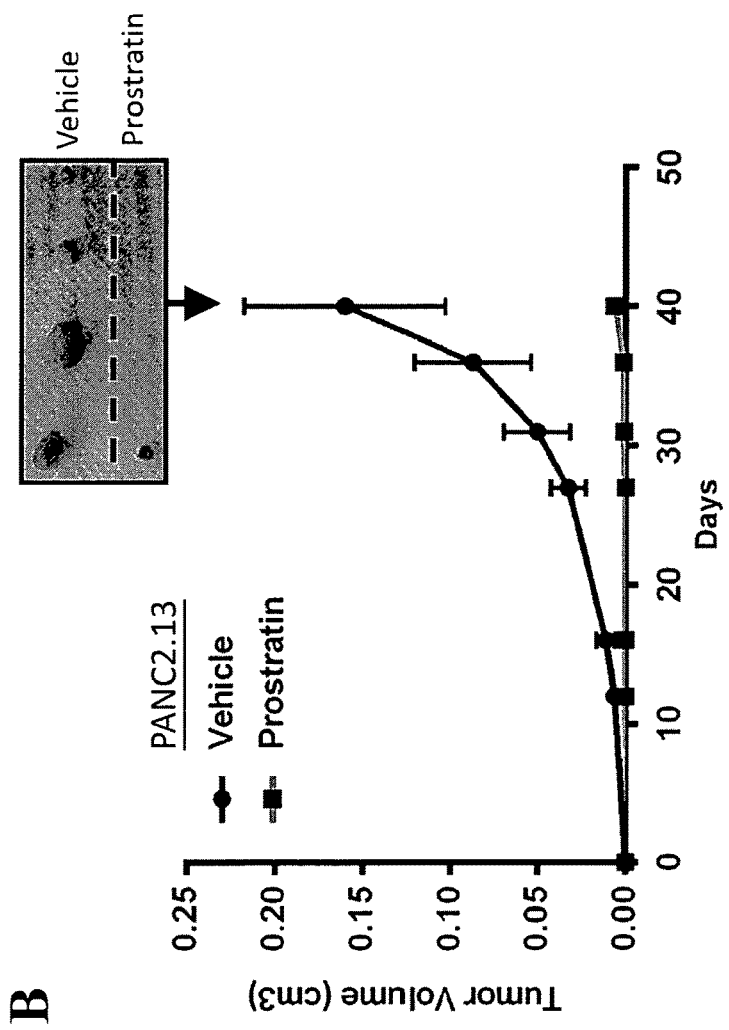
Figure 6:
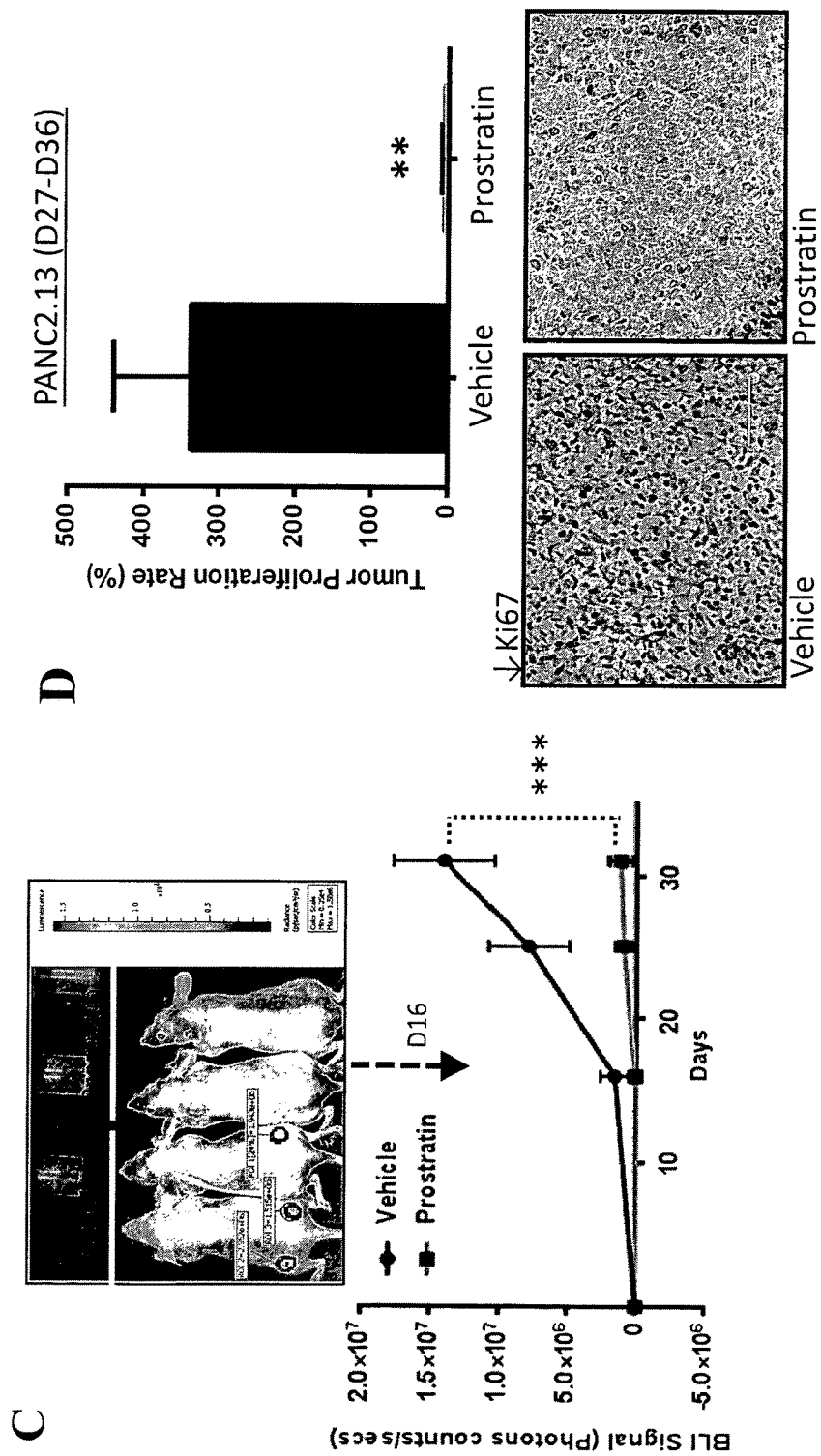
Figure 6:
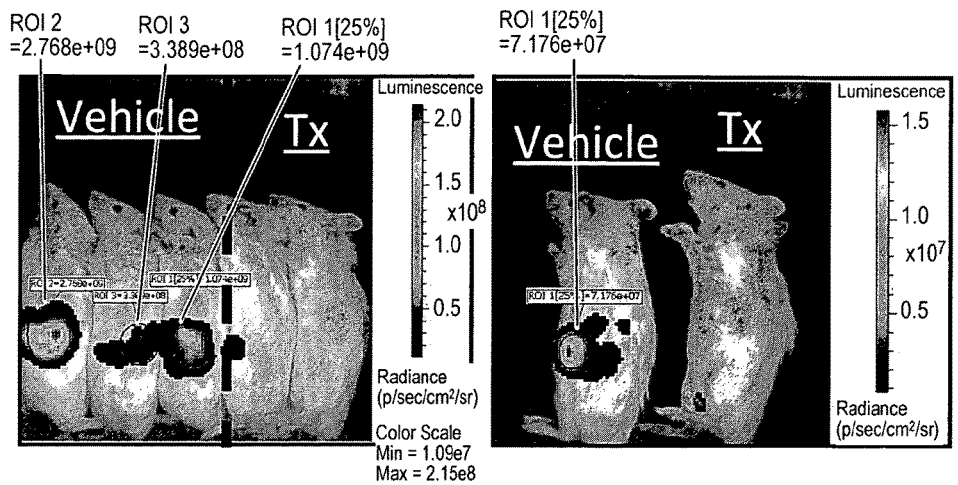
Figure 6:
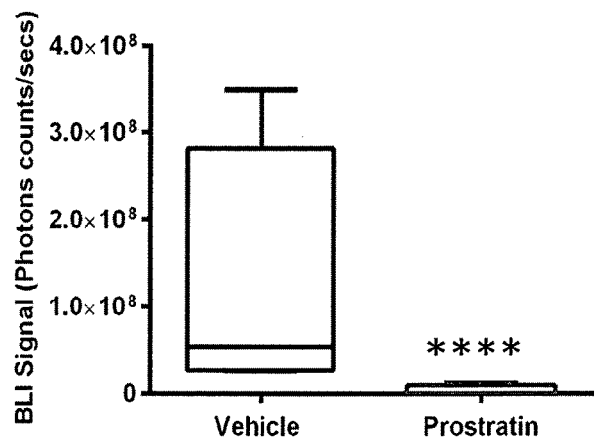
Figure 6:
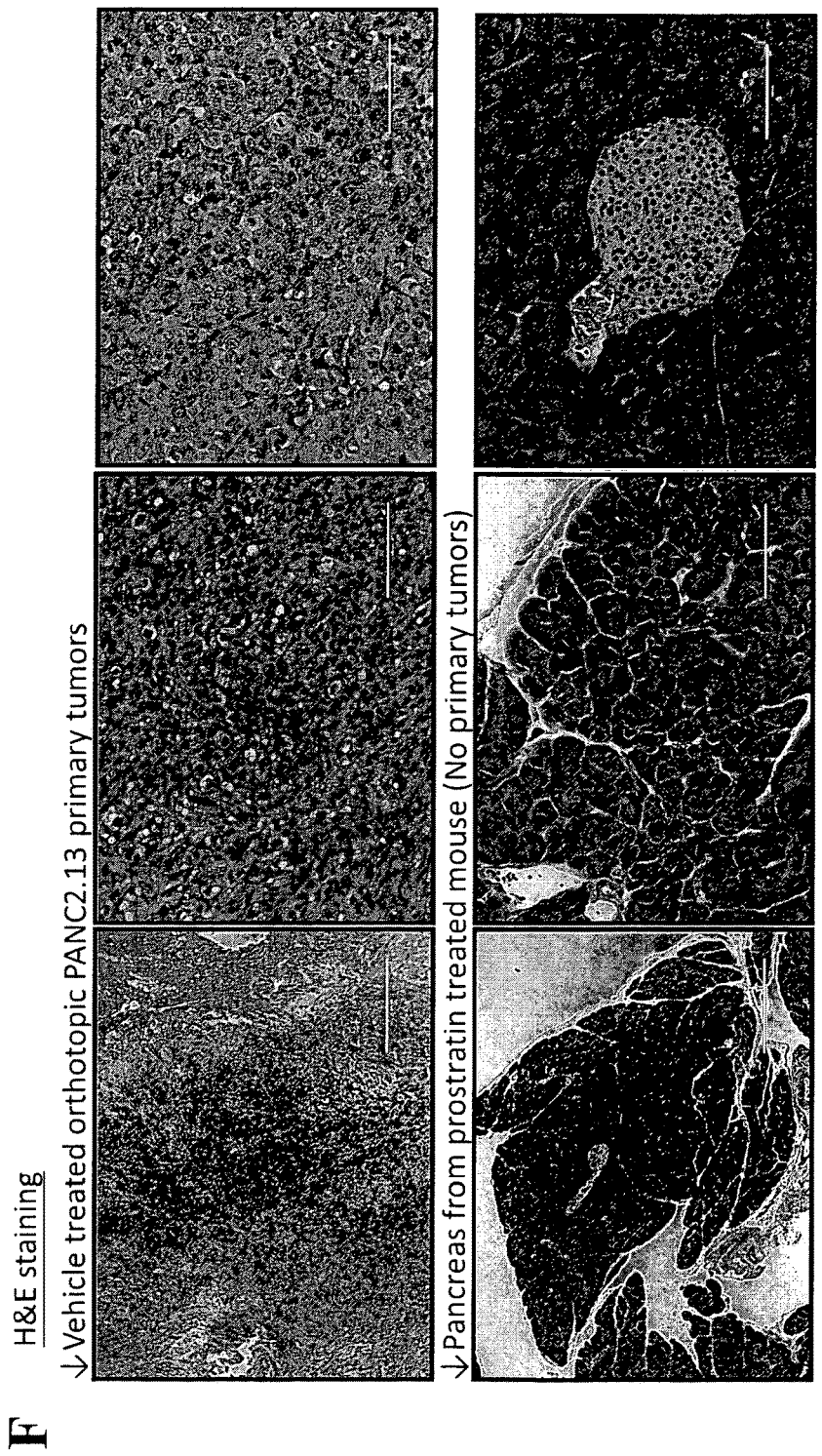
Figure 6:
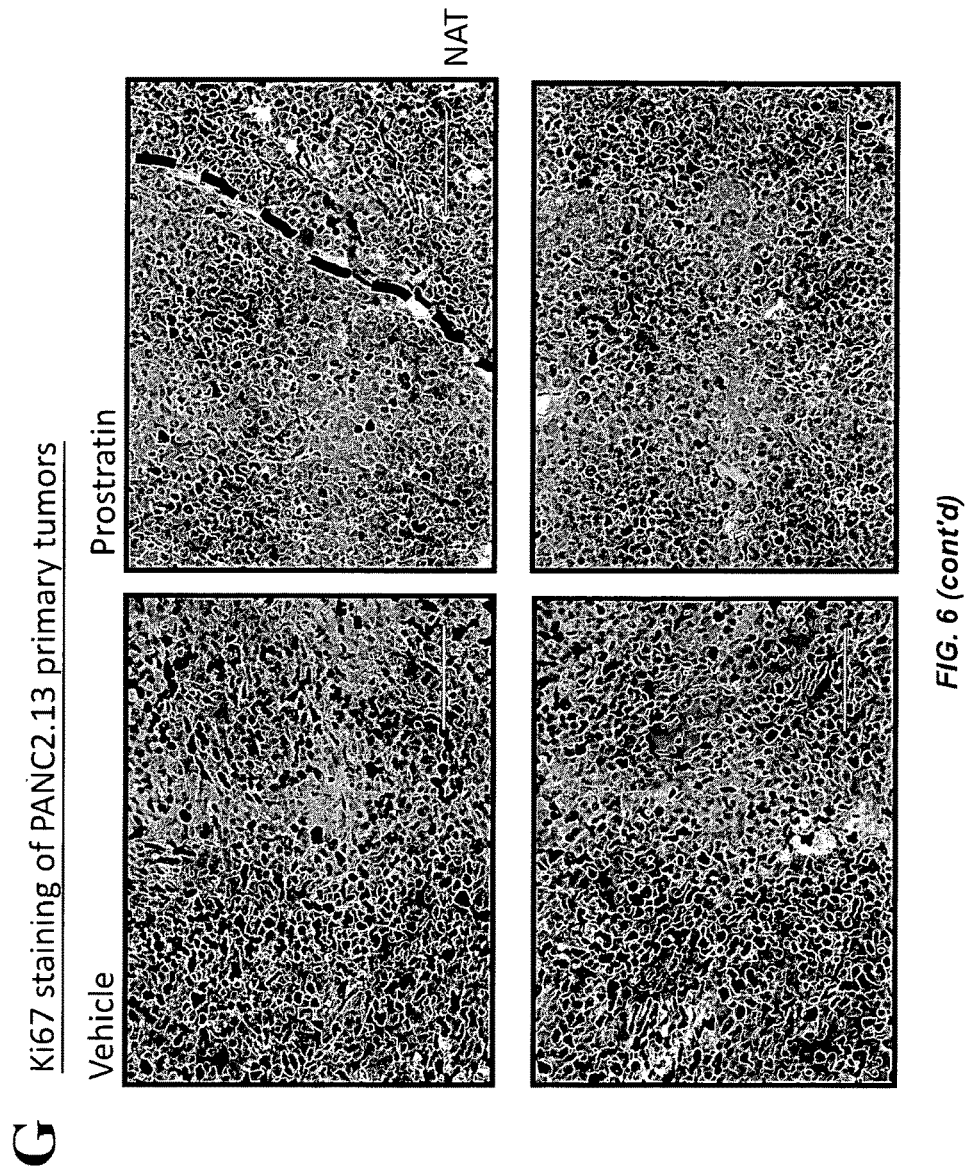

To test the anti-cancer effects of prostratin on K-Ras driven human pancreatic cancers in vivo, we first examined whether prostratin can prevent pancreatic tumor formation in a xenograft model. As FIG. 6A shows, prostratin significantly reduced the frequency of tumor formation in xenograft pancreatic tumors established at subcutaneous sites when compared to the vehicle treated group. Moreover, the average size of established tumors in the presence of prostratin was much smaller than the tumors in the control group (FIG. 6B). Pancreatic tumor cells were labeled with luciferase for detecting tumor formation more accurately. Bioluminescence imaging (BLI) confirmed that treatment with prostratin profoundly suppressed tumor initiation and tumor size (FIG. 6C). In addition, when compared to tumors in the control group, the xenografted pancreatic tumors treated with prostratin showed dramatically reduced tumor growth rate during therapy, as well as reduced expression of Ki67 (FIG. 6D).

In addition to testing the effects on prevention of subcutaneous tumors, we evaluated the anti-cancer effects of prostratin in orthotopic models of human pancreatic cancer cells with mutant K-Ras. ELISA-based PKC activity assay revealed that the oral route was preferable for delivering prostratin efficiently into the pancreas relative to the intraperitoneal route (FIG. 13F). Immuno-compromised NOD-SCID mice receiving daily oral treatments of prostratin had lower tumor burden in the orthotopic sites in the comparison with control treated mice: BLI analysis revealed that prostratin dramatically reduced the sizes of orthotopic tumors in animals when compared to the control (FIG. 6E and FIG. 14B). Moreover, treatment with prostratin reduced metastasis to the peritoneum in the orthotopic pancreatic cancer models (FIG. 6E and FIG. 14C). As shown in FIG. 6F and FIG. 14B, H&E staining revealed that most of prostratin treated mice did not show formation of primary tumors in the pancreas, whereas mice in the control group had obvious orthotopic tumors and normal pancreatic tissue was barely detectable. In addition, orthotopic tumors in the prostratin treated group expressed much lower Ki67 when compared to the control tumors (FIG. 6G and FIG. 14B). Taken together, our data suggest that prostratin significantly reduces tumor initiation frequency of human pancreatic cancers in xenograft models.

Figure 7:
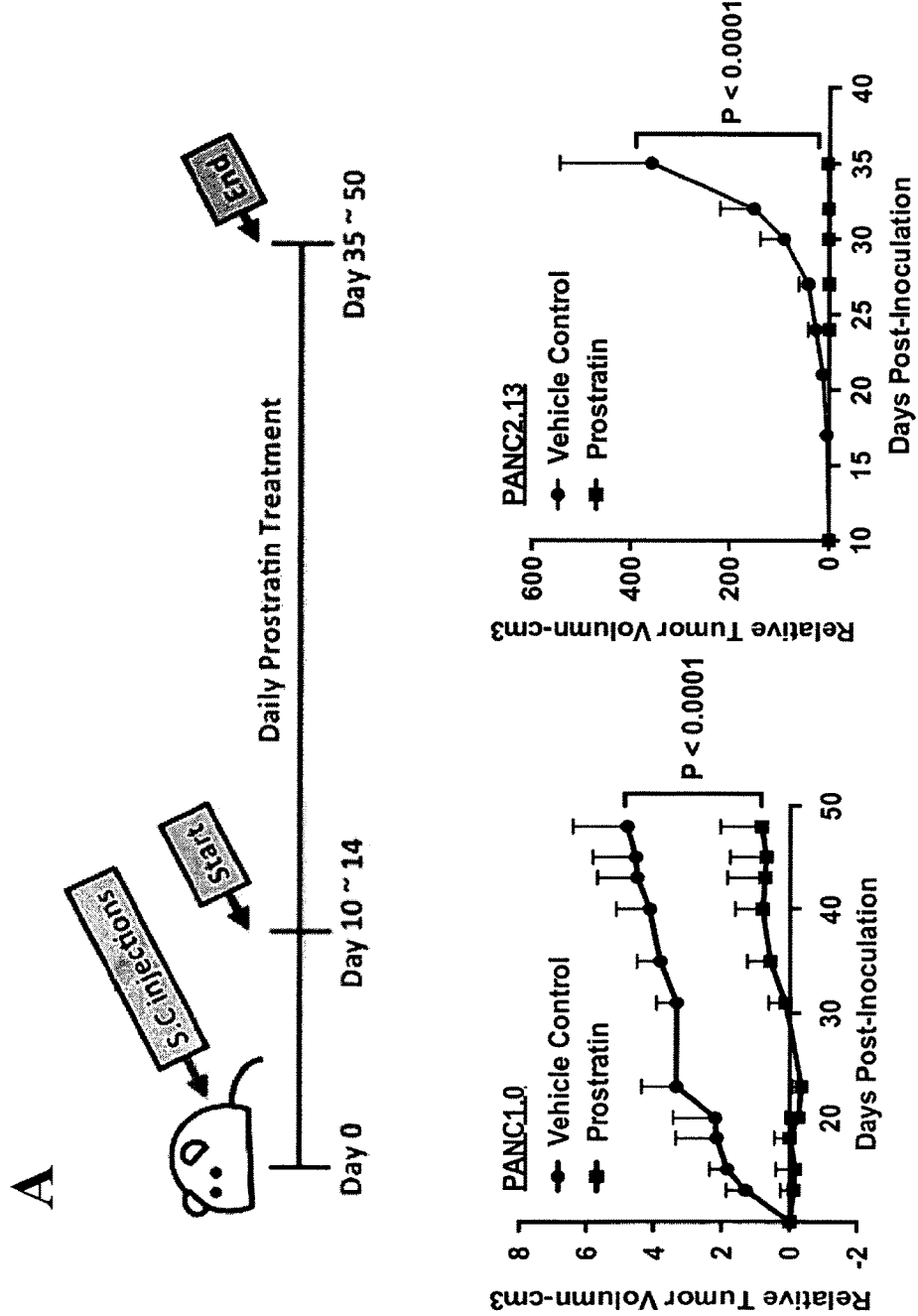
FIG. 7. Prostratin represses in vivo malignancy driven by oncogenic K-Ras. (A) Prostratin showed anti-tumor effects on established subcutaneous tumors derived from 0.5×10$^6$ cells of PANC1 or PANC2.13 (N=7; Data are means±SEM). (B) Prostratin suppressed orthotopic tumor burdens measured by cfDNA values (N=5 for PANC2.13 group; N=6 for PANC2.03 group). (C) Prostratin reduced the incidence of papilloma formations in LRIG1cre/ER/LSL-Ras$^{G12V}$ GEMM. Left Panel: schematic illustration of the generation of papilloma in LRIG1 cre/ER/LSL-Ras$^{G2}$V mice. Right panel: the pictures of mice carrying K-Ras$^{G12V}$-induced papillomas with vehicle or prostratin treatment. (D) Prostratin affected papilloma initiation differently in LRIG1cre/ER/LSL-H- and K-Ras$^{G12V}$ mice. (E) H&E staining and IHC stained for E-Cadherin and Vimentin in K-Ras$^{G12V}$-induced papillomas with vehicle (top panel) or prostratin treatment (bottom panel).
Figure 7:
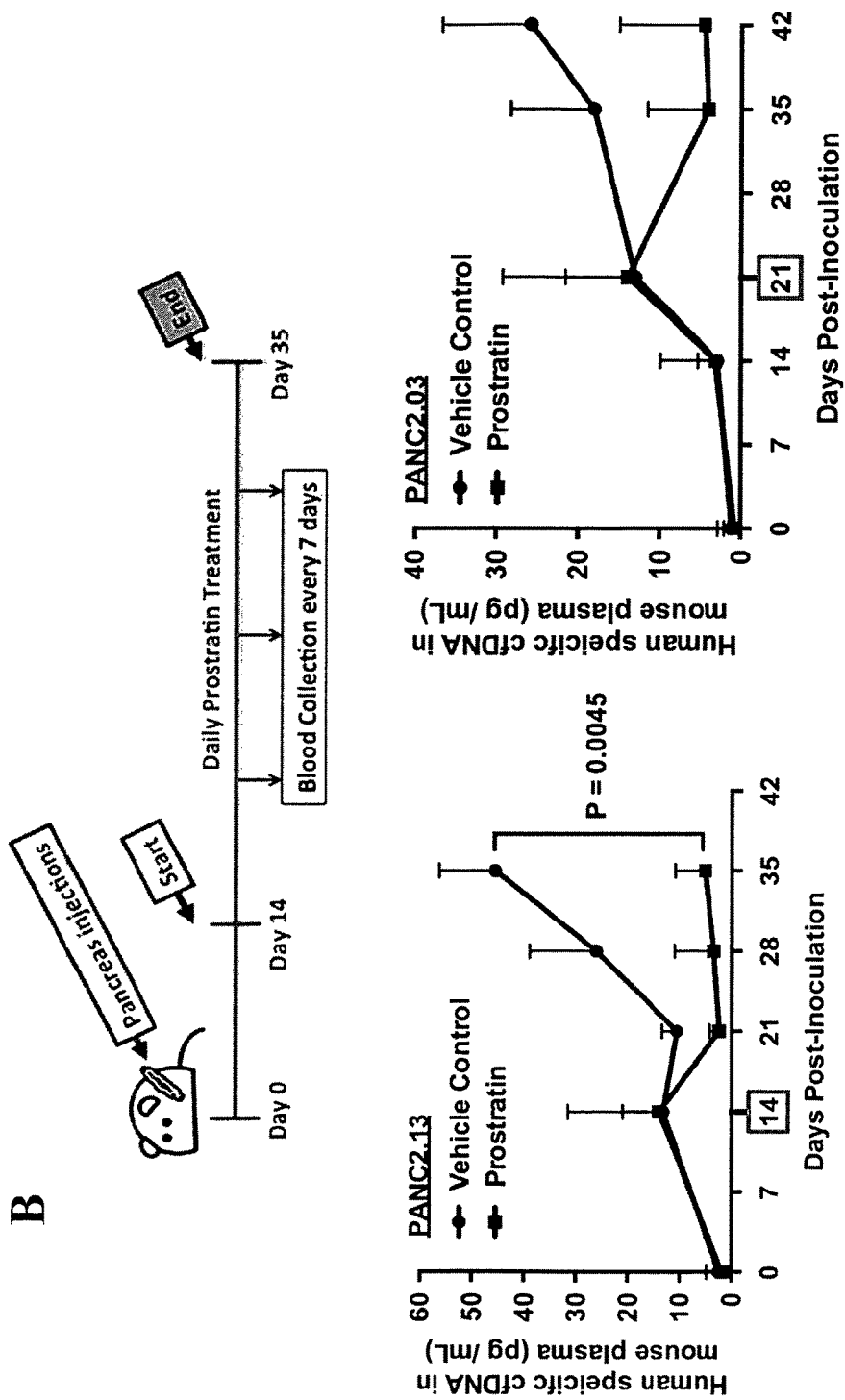
Figure 7:
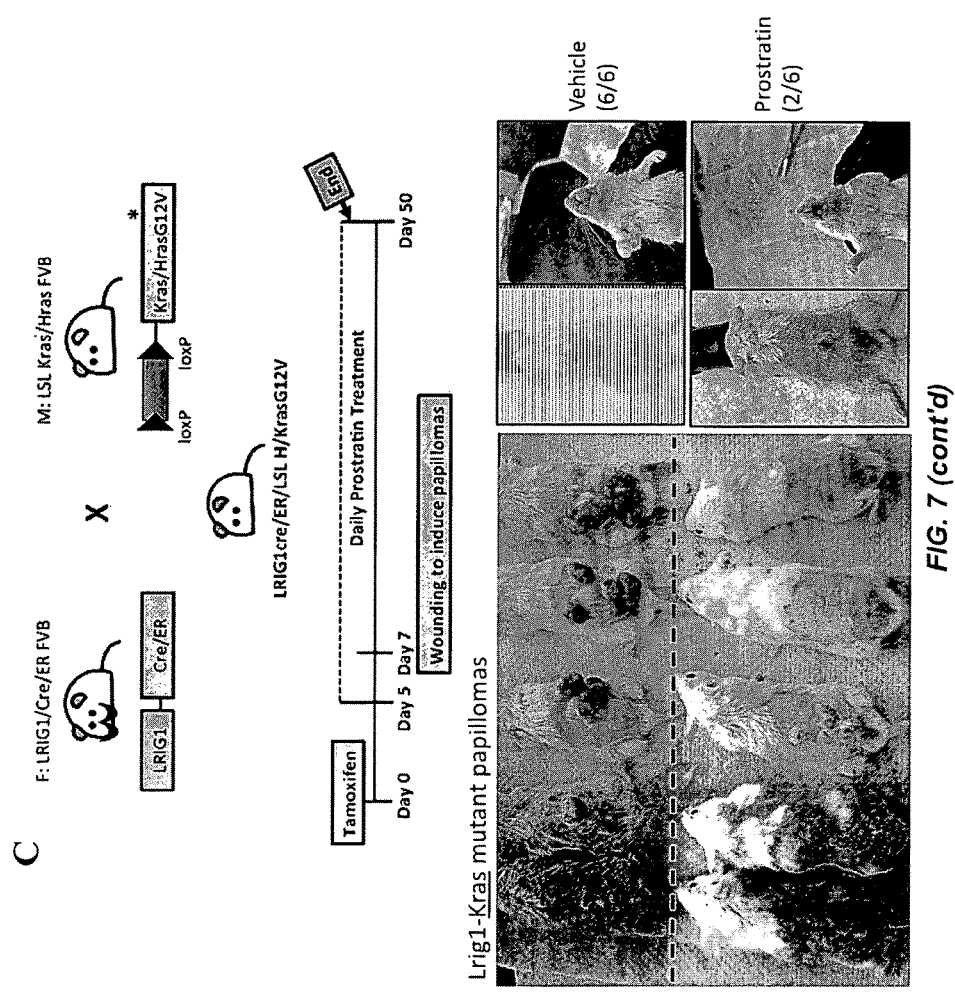
Figure 7:
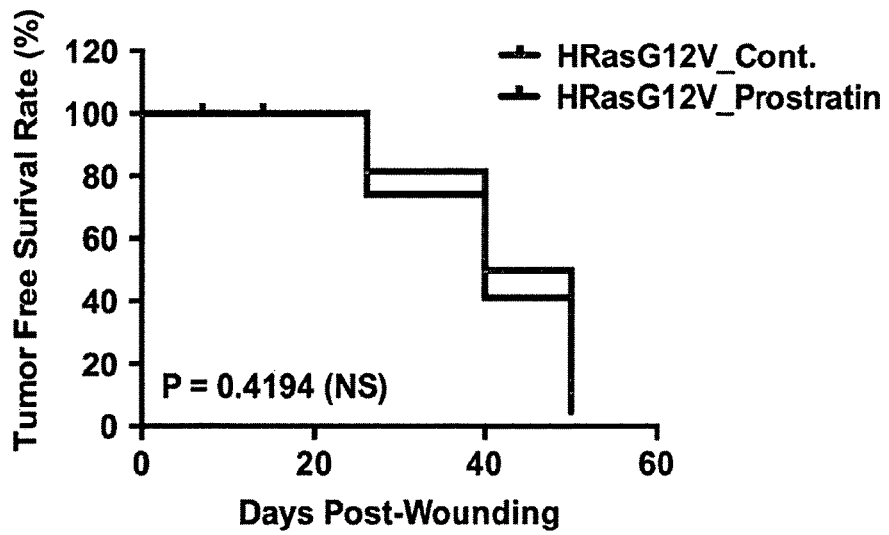
Figure 7:
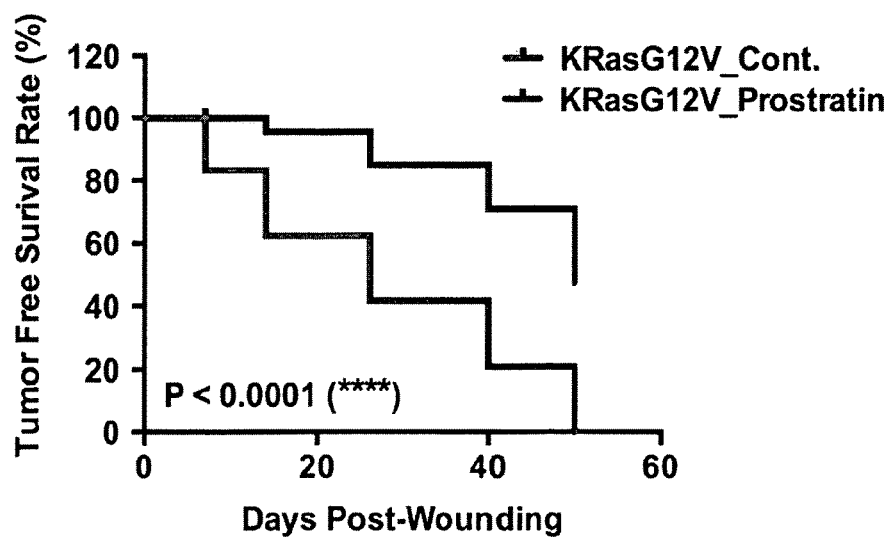
Figure 7:
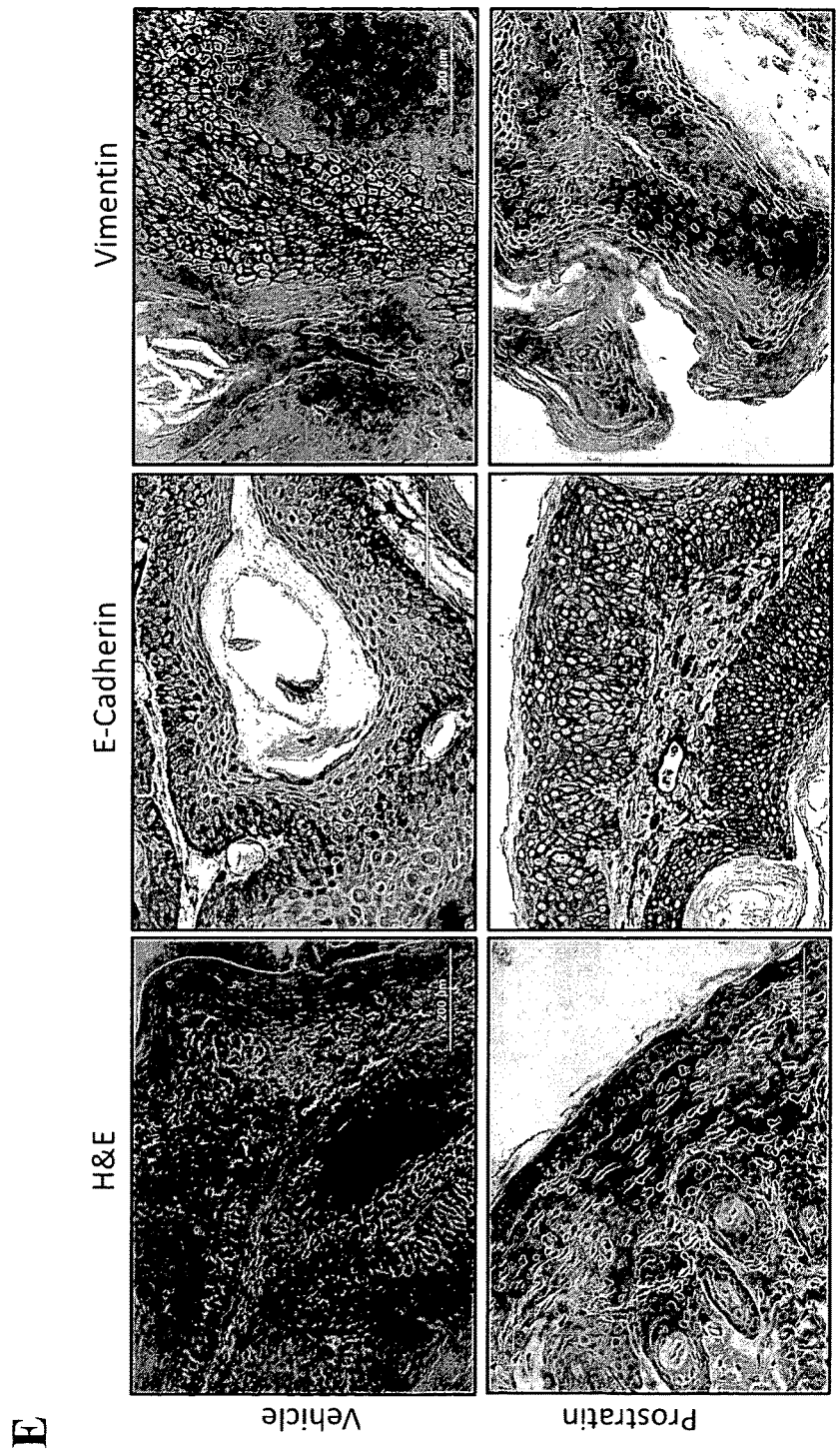

Next, we tested the anti-tumor effects of prostratin on established human pancreatic xenograft tumors. Human pancreatic cancer cells were subcutaneously or orthotopically transplanted into immune-compromised mice. Daily oral prostratin treatment started around 10 to 14 days post-injection, depending on the experimental cell lines and models (FIG. 7A). Intriguingly, prostratin showed anti-tumor activity on human pancreatic subcutaneous tumors, defined by the significantly reduced growth rate when compared to vehicle treated tumors (FIG. 7A). Additionally, prostratin treated subcutaneous tumors showed enhanced expression of cleaved caspase 3 (FIG. 14D), suggesting it exerts cytotoxic effects on established tumors.

Cell-free DNA (cfDNA) has been found at elevated levels in the bloodstream of cancer patients, and its concentration showed a nearly perfect correlation with primary tumor sizes following effective therapy or tumor recurrence Anker et al., *Cancer Metastasis Reviews* 18:65-73, 1999; Sozzi et al., *J. Clin Oncol* 21:3902-3908, 2003). Therefore, the quantification of the absolute levels of plasma cfDNA can be a useful tool for the diagnosis or monitoring of certain type of cancers, including pancreatic malignancies (Sikora et al., *The International Journal of Biological Markers* 30, e136-141, 2015). Here, we applied Taqman probes specifically detecting human cfDNA in mice in which human pancreatic cancer cells had be orthotopically implanted (Cheng et al., *Cancer Sci* 100:303-309, 2009) (FIG. 7B). The level of human cfDNA increased more than 6 times above baseline on the 14$^{th}$ day post-tumor implantation, when prostratin treatment started. The concentration of human specific cfDNA dramatically decreased in the prostratin treated animals over time, whereas it showed positive dynamic changes in the vehicle treated group (FIG. 7B). These data demonstrate that prostratin significantly represses the burden of human pancreatic cancers in orthotopic xenograft models.

Taken together, our data suggest that prostratin, an activator of atypical PKCs, can efficiently reduce the interaction of K-Ras and CaM, rewire Wnt/Ca2+ signaling, and suppress malignancy mediated by oncogenic K-Ras in pancreatic cancers.

Prostratin Specifically Represses K-Ras$^{G12V}$-Induced Papilloma

We further examined the effects of prostratin on oncogenic Ras induced tumors in a genetically engineered mouse model (GEMM). We first used a papilloma model driven by H- or K-Ras$^{G12V}$ under the control of a skin stem cell promoter, Lrig1 (FIG. 7C) (Jaks et al., *Exp Cell Res* 316: 1422-1428, 2010; Page et al., *Cell Stem Cell* 13, 471-482, 2013). In this GEMM, tamoxifen inducible Cre recombinase initiates the expression of oncogenic H- or K-Ras$^{G12V}$, and the enforced oncogenic Ras expression disrupts the skin hemeostasis during wound healing and further induces papilloma formations (FIG. 7C).

Daily prostratin treatment significantly delayed/reduced the formation of papillomas driven by K-Ras$^{G12V}$, whereas it showed no effects on the initiation of H-Ras$^{G12V}$-induced tumors (FIG. 7D). It should be noted that, in the same genetic background, oncogenic K-Ras drove the skin tumor initiations in much higher frequency than oncogenic H-Ras, and that result from GEMMs is consistent with those observed in xenograft models transplanted with Ras$^{V12}$-transformed MEFs.

A well-known feature of epithelial tissues, such as the epidermis, is the coexistence of multiple stem cell populations. Lrig1 is one of multiple markers associated with stem cells in the upper pilosebaceous unit (Jaks et al., 2010; Jensen et al., *Nat Protoc* 5:898-911, 2010). In the epidermis, these Lrig1$^+$ cells are capable of contributing to all epidermal lineages in skin-reconstitution assays (Jensen et al., 2010). Here, we show that K-Ras$^{G12V}$ initiated skin tumors at a much higher rate than H-Ras$^{G12V}$ under the identical Lrig1 promoter, further supporting functional roles of oncogenic K-Ras, not H-Ras, on cancer stem cells or tumor initiating cells. In addition, prostratin not only reduced the tumor initiation frequency, but also significantly slowed down the growth rate of K-Ras$^{G12V}$-induced papillomas (FIG. 14E). Interestingly, the K-Ras$^{G12V}$-driven skin tumors in the control group showed epithelial-mesenchymal transition (EMT) properties, including the lowered expression of E-cadherin and increased expression of vimentin, while the prostratin treated tumors maintained strong expression of epithelial maker (FIG. 7E). These data suggest that the prostratin can selectively suppress the formation and progression of papillomas driven by oncogenic K-Ras in this GEMM.

In summary, our results indicated that prostratin selectively inhibited the formation of skin tumors as results of oncogenic-K-Ras in immunocompetent mice. Together with the data in xenograft models, we suggest that prostratin could be a novel and effective drug with selective activity against oncogenic K-Ras-driven cancers.

Discussion

Historically, the high degree of sequence homology, coupled with similar ability of mutant H-Ras, N-Ras, and K-Ras oncogenes to transform cells in culture and to activate common cellular signaling pathways, supported the idea that these three Ras gene products are functionally redundant. Herein we report that H-Ras and K-Ras differ in their abilities to induce tumor initiation and that this is directly related to the ability of K-Ras to suppress the Fzd8-mediated non-canonical Wnt/Ca$^{2+}$ signaling pathway.

Figure 10:
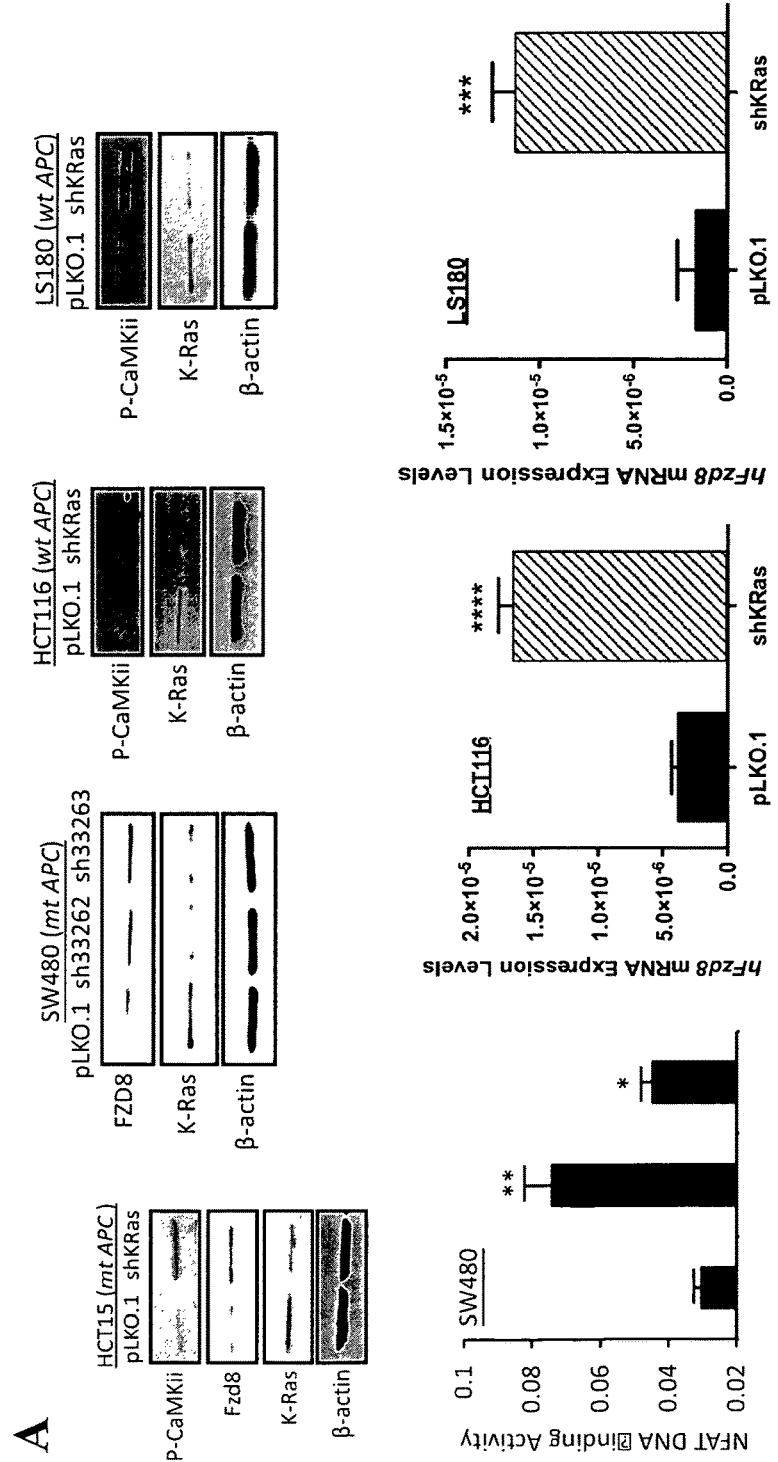
FIG. 10. (A) Knockdown of mutant K-Ras increased the expression of Fzd8, and phosphorylation of CaMKii or NFAT transcriptional activity in colon cancer cell lines (N=3). (B) TOPFlash in colon cancer cell lines in which K-Ras had been knocked down (N=3). (C) Organoid formation assay in colon cancer cell lines in which K-Ras had been knocked down (N=6). (D) BrdU incorporation assay was used to evaluate the cell proliferate rate in colon cancer cell lines in which K-Ras had been knocked down. pLKO.1 expressing cells were used as control for normalization (N=6). (E) Relative TOPFlash activity in NIH/3T3 cells treated with different Tankyrase inhibitors for 12 hours. DMSO treated cells were used for normalization (concentration: 0.5 μM for each compound) (N=4). (F) Sphere formation assay in NIH/3T3 cells treated with different Tankyrase inhibitors for 12 hours. DMSO treated cells were used for normalization (N=6). * $P<0.05$;  $P<0.01$; * $P<0.001$; **** $P<0.0001$.
Figure 10:
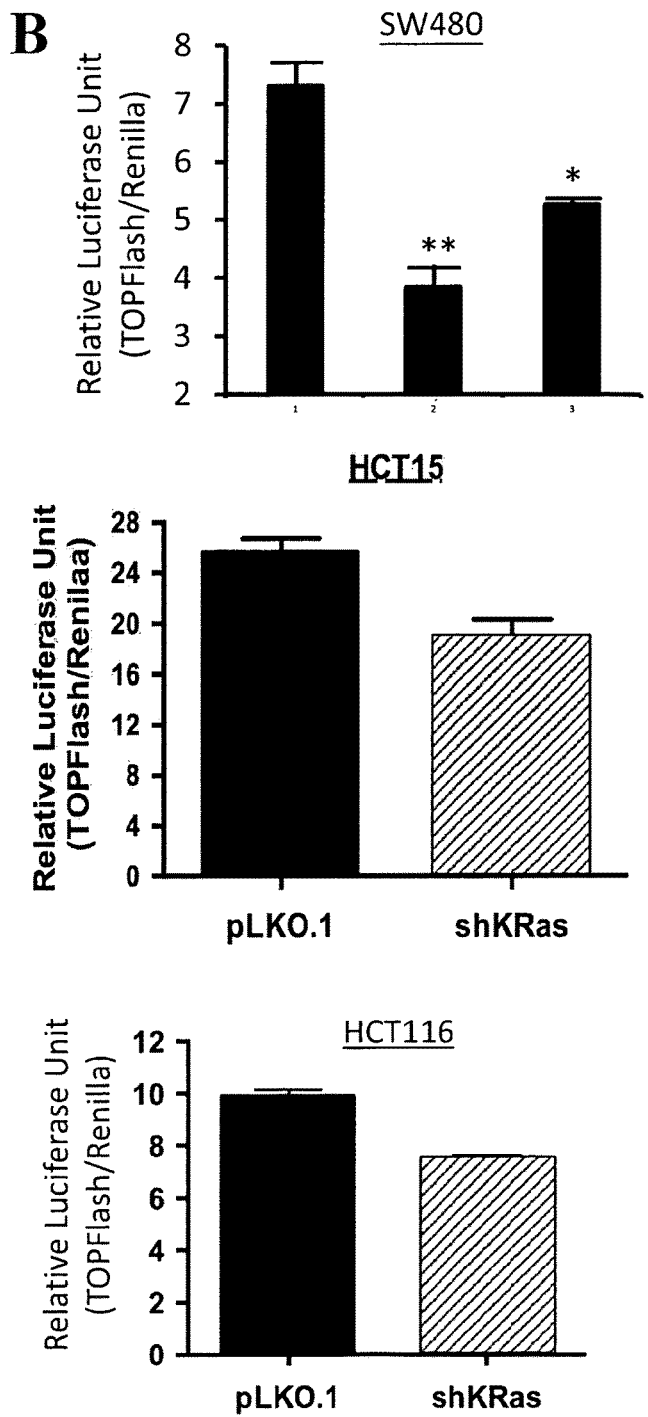
Figure 10:
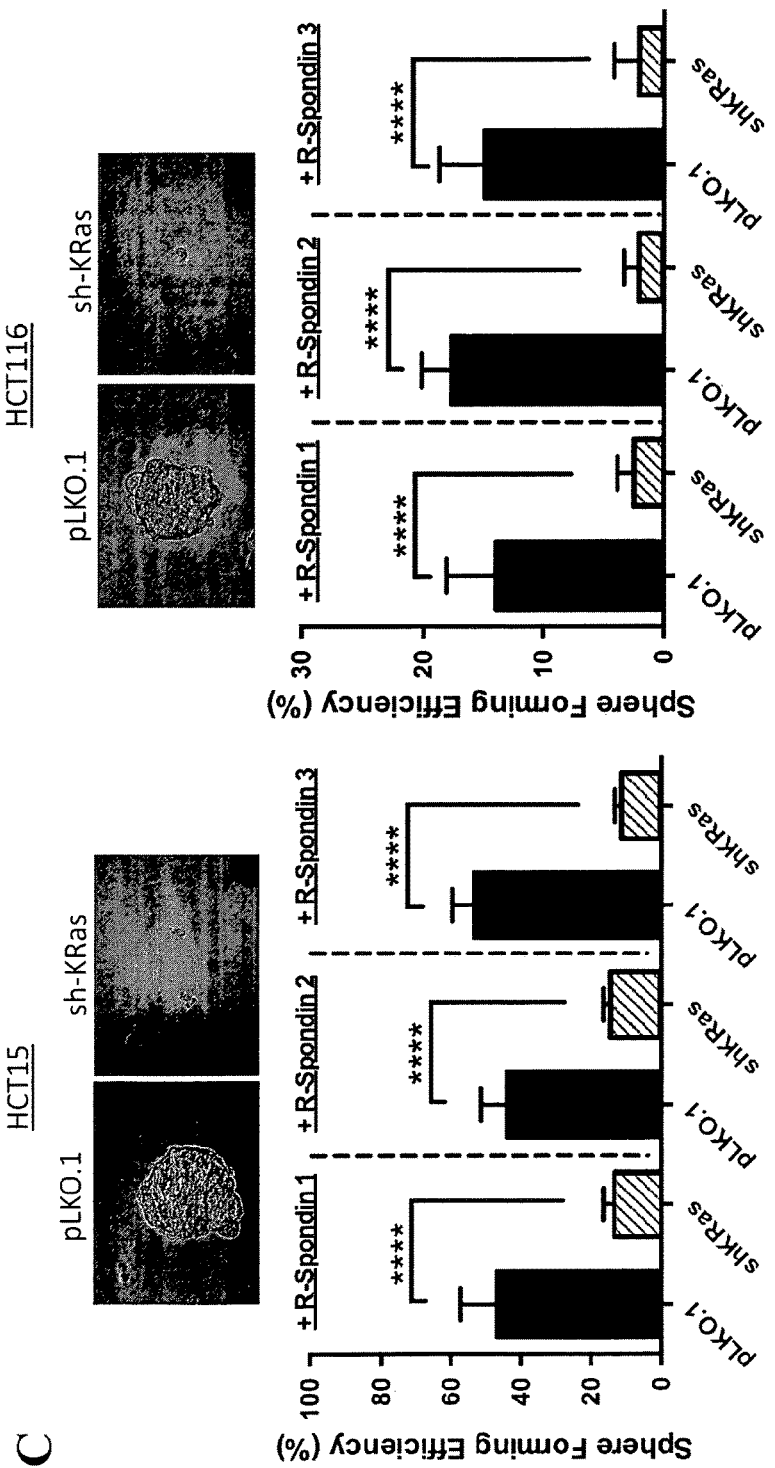
Figure 10:
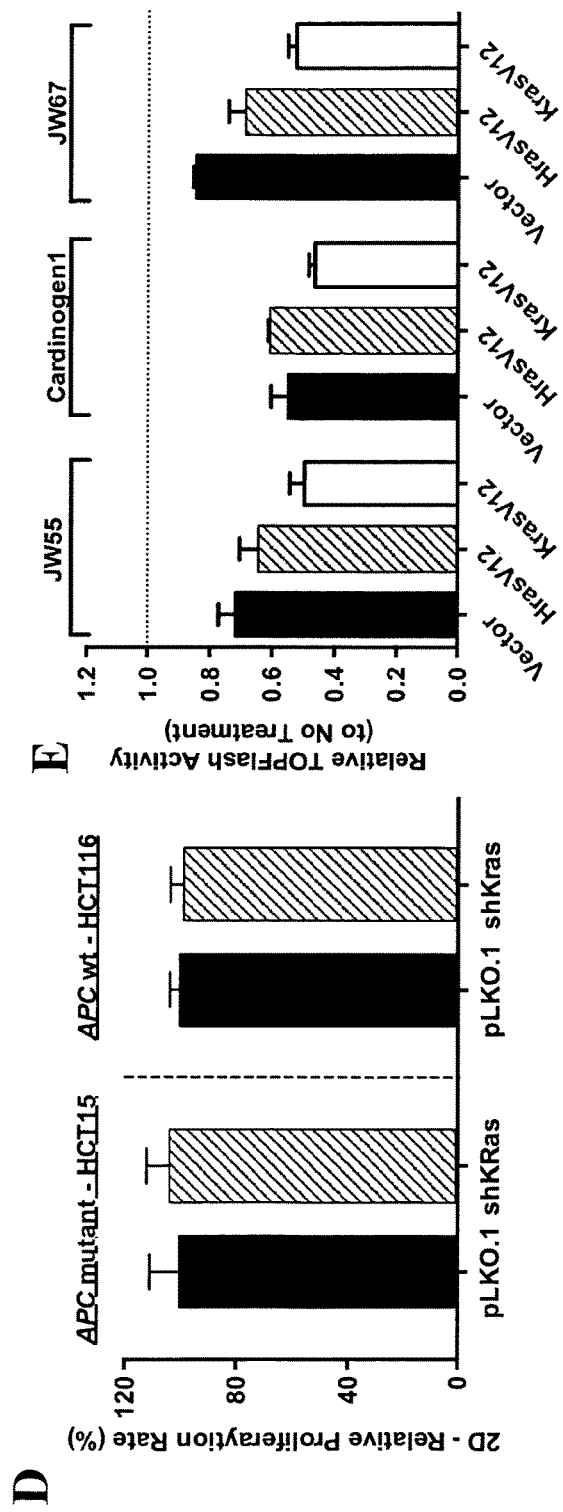
Figure 10:
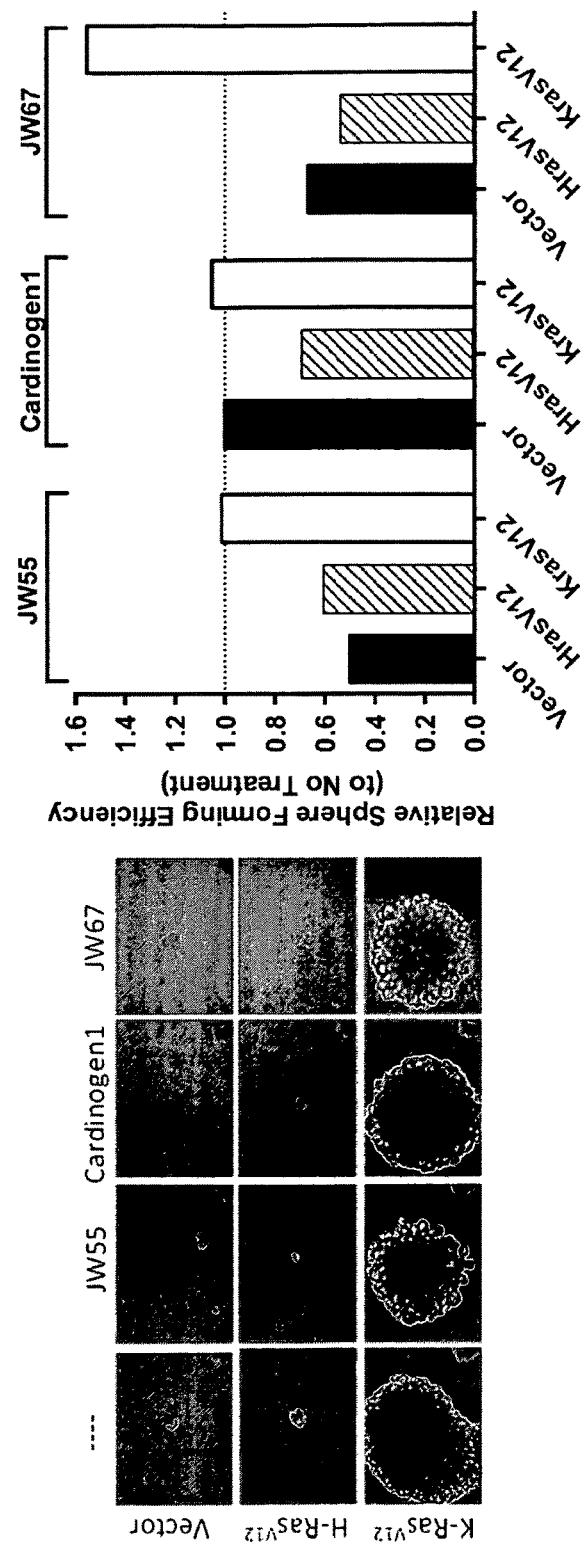

Constitutive activation of canonical Wnt/β-catenin signaling pathway, driven by loss-of-function mutation in the negative regulator, APC, and/or gain-of-function mutations in β-catenin, is directly associated with the initiation of several types of tumors, most notably colon cancer. However, such genetic lesions in classic β-catenin regulatory proteins occur very rarely in human pancreatic cancers (Abraham et al., *Am J Pathol* 160:1361-1369, 2002; Gerdes et al., *Digestion* 60:544-548, 1999; Seymour et al., *Cancer Res* 54:2761-2764, 1994), suggesting alternative routes for activation of Wnt/β-catenin signaling pathway in PDAC. Depletion of β-catenin expression by siRNA decreases proliferation and accelerates apoptosis of mouse pancreatic carcinomas in the context of mutant K-Ras (Pasca di Magliano et al., *PLoS One* 2:e1155, 2007). Furthermore, levels of β-catenin are positively correlated with PanIN grade and the development of invasive PDAC (Al-Aynati et al., *Clin Cancer Res* 10:1235-1240, 2004; Pasca di Magliano et al., 2007; Wang et al., *Cancer Cell* 15:207-219, 2009), indicating a potential contribution of Wnt/β-catenin signaling to PDAC maintenance. However, mice expressing activating mutations in β-catenin in acini and endocrine cells showed increased age-dependent accumulation of nuclear β-catenin and Wnt/β-catenin-target gene expressions, and eventually failed to develop pancreatic tumors (Strom et al., *Development* 134:2719-2725, 2007). Together with evidence that Cre-induced β-catenin stabilization/activation was incapable of synergizing with K-Ras to drive pancreatic intraepithelial lesions (PanIN) or PDAC in transgenic mice (Heiser et al., *Gastroenterology* 135:1288-1300, 2008), it appears that Wnt/β-catenin signaling pathway is not sufficient to initiate PDAC. Here, we report that inhibition of β-catenin activity by tankyrase inhibitors did not show any negative effects on K-Ras-mediated malignancy in vitro (FIG. 10). Moreover, suppression of oncogenic K-Ras expression by shRNA in colon cancer cell lines significantly repressed their growth in "organoid" culture, regardless of the presence of mutant or wild type APC (FIG. 10). Taken together, we conclude that greater tumor initiation ability of oncogenic K-Ras than H-Ras is not simply due to increased canonical Wnt/β-catenin signaling. While non-canonical Wnt/Ca$^{2+}$ signaling pathway plays an important role in oncogenic Ras-mediated tumor initiation, the canonical β-catenin signaling cascade is not be the only down-stream route for by which it modulates malignant features of oncogenic K-Ras driven tumors. Therefore, other potential down-stream pathway(s) of Fzd8-mediating non-canonical Wnt/Ca$^{2+}$ signaling need to be identified.

A major mediator of non-canonical Wnt/Ca$^{2+}$ signaling pathway is calmodulin-dependent kinase II (CaMKii). CaMKii is regulated by its binding to calmodulin (Bachs et al., *Cell Calcium* 16:289-296, 1994; Klee and Vanaman, *Adv Protein Chem* 35:213-321, 1982; Stewart et al., *FEBS Lett* 137:80-84, 1982). Interestingly, calmodulin has been found to bind exclusively to K-Ras4B, but not to other N-, H- or K-Ras4A, and a peptide with sequence of the CaMKii-binding domain of calmodulin is able to block this specific interaction (Villalonga et al., *Mol Cell Biol* 21:7345-7354, 2001). Our study confirmed that K-Ras$^{V12}$, but not H-Ras$^{V12}$, can bind to calmodulin in a Ca$^{2+}$ dependent manner. While oncogenic K-Ras binds to calmodulin constitutively, wild type K-Ras protein can bind to calmodulin only when it is activated, such as by EGF in BxPC3 cells. Furthermore the binding of K-Ras to calmodulin is attenuated by phosphorylation of Ser181 in the hypervariable region, as. the K-Ras$^{V12}$ variant (S181D), which mimics the Ser181 phosphorylated form of K-Ras, does not bind to calmodulin. The K-Ras$^{V12}$ S181D variant lost the ability to suppress CaMKii activity and Fzd8 expression, suggesting that the interaction between K-Ras and calmodulin, which is isoform specific, GTP-dependent and highly regulated, is an important pathway for K-Ras to inhibit Fzd8-mediated non-canonical Wnt/Ca$^{2+}$ signaling. Therefore, blocking this specific interaction between K-Ras and calmodulin may provide a novel approach to target K-Ras selectively.

Herein, we report that activation of PKC by prostratin leads to the dissociation of K-Ras-CaM interaction, activates non-canonical Wnt/Ca$^{2+}$ signaling, and suppresses oncogenic K-Ras-mediated malignancy. Our finding leads to an open question: while the activation of PKC isozymes by phorbol esters has long been considered to promote tumorigenesis, what drives the difference between PKC activation by prostratin and other typical activators, such as PMA?

Protein Kinase C (PKC) has been implicated in tumorigenesis for over 30 years, since it was first characterized as a receptor for the tumor-promoting phorbol esters (Castagna et al., *J. Biol Chem* 257:7847-7851, 1982). However, recent studies have characterized PKC as a family of related isoforms, categorized as conventional (α, βI, βII, and γ), novel (δ, ε, η, and θ), and atypical (ζ, λ/ι) (Basu and Pal, *Scientific World Journal* 10:2272-2284, 2010), and that PKC isozymes may exhibit overlapping as well as opposing functions (Steinberg, *Physiol Rev* 88:1341-1378, 2008). For example, PKCδ is believed to function as a tumor suppressor since down-regulation rather than activation of PKCδ has been associated with tumor promotion (Lu et al., *Mol Cell Biol* 17:3418-3428, 1997). Surprisingly, a recent study revealed that the majority of cancer-associated mutations in PKC subgroups are lost-of-function (LOF) (Antal et al., *Cell* 160:489-502, 2015). Correction of a LOF mutation in PKCβ by CRISPR-mediated genome editing suppressed t in vitro and in vivo malignancies of patient-derived colon cancer cells (Antal et al., 2015). More importantly, several mutations found in PKC isozymes were dominant negative, that function to suppress global PKC signaling output (Antal et al., 2015). This establishes a new hypothesis: PKC isozymes generally function as tumor suppressors and, therefore, anti-cancer therapies should focus on restoring, not inhibiting PKC activity. This suggestion had also been made by Bivona and colleagues (Bivona et al., *Mol Cell* 21:481-493, 2006) based on their observations that PKC-mediated phosphorylation of K-Ras at serine-181 affects K-Ras activity. Interestingly, PMA and prostratin have been shown to differ substantially in their biological activities (activation vs. subcellular translocation) on PKCα and PKCδ (Marquez et al., *Biochem Pharmacol* 75:1370-1380, 2008), potentially explaining their distinct properties on tumor promotion.

In summary, K-Ras suppresses Wnt/$Ca^{2+}$ signaling pathway by direct binding with calmodulin, leading to reduced CaMKii activity and down-regulating Fzd8 expression. The down-regulation of Fzd8 expression by K-Ras leads to a sustained suppression of Wnt/$Ca^{2+}$ signaling, which in turn causes increases canonical Wnt signaling and tumorigenicity. The described isoform specific activities of K-Ras can be exploited as alternate targets to block K-Ras oncogenic activity without affecting other Ras isoforms.

Experimental Procedures
Cell Lines

NIH/3T3, BxPC3, PANC1, and PANC2.03 cells were from ATCC. Mouse pancreatic adenocarcinoma cells were a gift from Dr. Eric Collisson at UCSF. Rasless MEFs expressing H-, N- or K-Ras were a gift from Cameron Pitt at UCSF. Mouse cell lines were grown in Dulbecco's modified Eagle's medium (DMEM) supplemented with 10% FBS (or CS for NIH/3T3 cells) at 37° C., 5% $CO_2$. Human pancreatic cancer cell lines were maintained in ATCC modified RPMI-1640 medium supplemented with 15% FBS and human recombinant insulin (Gibco 12585-014).

K-Ras and H-Ras constructs were sub-cloned into pBabe retroviral expression vector, and Serine 181 point mutations were introduced using standard mutagenesis techniques (Agilent QuikChange II XL site directed mutagenesis kit). Viral particles for each expression construct were packaged in 293 cells, and NIH/3T3 cells were transduced at approximately 1 MOI. Transduced cells were then selected in growth media supplemented with 2 µg/ml puromycin.

Tankyrase inhibitors, JW55, Cardinogenl, and JW67, were purchased from R&D Systems. The cells were treated with the inhibitors at 0.5 µM for 12 hours for TOPFlash assays. For sphere formation assays, the cells were cultured in complete medium with different Tankyrase inhibitors.

Animal Studies

All experiments were approved by the IACUC of the University of California, San Francisco. $Ras^{V12}$-transformed NIH/3T3 cells were subcutaneously injected in female nude mice (Nu/Nu) at 50, 100 or 1,000 cells per flank. Palpable tumors were measured twice a week. The animals were divided into five mice per group. Pancreatic adenocarcinoma cells derived from $Braf^{CA}$ and $Kras^{LSL-G12D}$ mice are provided by Eric Collisson, and genotyped as described (Collison et al., *Nat Med* 17:500-503, 2011; Dankort et al., *Genes Dev* 21:379-384, 2007; Hingorani et al., *Cancer Cell* 4:37-450, 2003). One hundred cells were orthotopically implanted in 6- to 8-week-old FVB/n mice in 20 µL 50% Matrigel using a 28.5-gauge needle. Mice were monitored for one month and were euthanized when distressed.

Skin tumors were induced by the two-stage chemical carcinogenesis protocol using 7,12-dimethylbenz(a)anthracene (DMBA) and 12-O-tetradecanoylphorbol-13-acetate (TPA) as previously described (Balmain and Pragnell, *Nature* 303:72074, 1983). Histologically confirmed skin carcinomas were processed into DNA, RNA and protein for molecular analyses by conventional methods. Mutations in Kras and HrasK1 alleles were identified by direct sequencing as previously described (To et al., *Nat Genet* 40:1240-1244, 2008).

The prostratin for animal treatment was purchased from Santa Cruz Biotechnology (sc-203422A). The drug was daily administrated into either NOD-SCID or athymic nude mice by oral gavages (OG) at 1 mg/kg or intraperitoneal (I.P) injection at 0.5 mg/kg. 10% DMSO, 10% cremophor, and 80% saline solutions were used as the solvent and vehicle control. The toxic effect of either vehicle or prostratin was evaluated by monitoring the changes of body weights for at least 30 days.

Lrig1 Cre/ER/LSL Hras and Lrig1 Cre/ER/LSL-$Kras^{G12D}$ mice have been backcrossed into the FVB/N background over multiple generations to minimize the effects of genetic heterogeneity on tumor development. Cre recombinase was activated in both groups of mice by administering a single dose of 4oht (Tamoxifen), topically applied at 8 weeks of age. On day 7 thereafter, wounding was induced on their backs by cutting a 2 cm incision for papilloma development.

DNA Extraction from Mouse Plasma Samples

All blood samples were collected in $K_2EDTA$ containing tubes (BD Microtainer, Ref 365974) and centrifuged at 1,500 g for 10 min. Then the supernatants were carefully collected from the top portion of the plasma to eliminate the possibility of cell contaminations. The plasma was stored at −80° C. until further use. The cfDNA was extracted from 100 µL of plasma using NucleoSpin Plasma XS kit (Macherey-Nagel; 740900).

Quantification of Human Nucleic Acid in Mouse Plasma

Nucleic acid concentrations in all plasma samples were measured by quantitative polymerase chain reaction (PCR) using the AB7900HT (Applied Biosystems, Foster City, CA, USA) and TaqMan Universal PCR Master Mix (Applied Biosystems) according to the manufacturer's protocol. For quantification of human β-actin genomic DNA in mouse plasma samples, the following custom primers and probe sets were used:

```
                                            (SEQ ID NO: 4)
forward primer, 5'-ATCCTAAAAGCCACCCCACT-3';

(SEQ ID NO: 5)
reverse primer, 5'-CTCAAGTTGGGGGACAAAAA-3';
and (SEQ ID NO: 6)
probe, 5'-FAM-CACAGGGGAGGTGATAGCAT-TAMURA-3'.
```

RNA Interference

The shRNAs vectors against H-Ras, K-Ras and Fzd8 were purchased from Open Biosystems. The shRNA constructs were packaged as lentiviruses by using $3^{rd}$ generation of *lenti*-virus packaging systems using standard protocols. The packaging plasmids were from Addgene.

RasGTP Pull-Down Assay

Cells were washed twice in ice-cold PBS and lysed in 1% TX100-TNM lysis buffer (20 mmol/L Tris pH 7.5, 5 mmol/L MgCl$_2$, 150 mmol/L NaCl, 1% Triton X-100) supplemented with 1 mmol/L DTT, and protease and phosphatase inhibitors (Sigma-Aldrich). Equal amounts of protein from each sample were added to 10 μL of packed GST-Raf-RBD or Ral-GDS-RBD beads in 300 to 500 μL of 1% TX100-TNM lysis buffer and rotated at 4° C. for 1 to 2 hours. Beads were washed 3 times with 1 mL of cold lysis buffer and boiled in lithium dodecyl sulfate (LDS) sample buffer (Invitrogen).

K-LISA Akt Activity Assay

The K-LISA Akt activity kit was purchased from EMD Millipore (CBA019). Cells were washed twice in ice-cold PBS and lysed in 1% TX100-TNM lysis buffer (20 mmol/L Tris pH 7.5, 5 mmol/L MgCl$_2$, 150 mmol/L NaCl, 1% Triton X-100) supplemented with 1 mmol/L DTT, and protease and phosphatase inhibitors (Sigma-Aldrich). The cell lysates with equal amount of protein were incubated with biotin-layted peptide substrate which can be phosphorylated by Akt1, 2, and 3. The full procedure and plate reading were performed according to the manufacturer's instructions.

Western Blotting Analysis

Experimental cells were washed twice in ice-cold PBS and lysed in 1% Triton lysis buffer [25 mmol/L Tris pH 7.5, 150 mmol/L NaCl, 1% Triton X-100, 1 mmol/L EDTA, 1 mmol/L EGTA, 20 mmol/L NaF, 1 mmol/L Na$_2$VO$_4$, and 1 mmol/L DTT] supplemented with a protease inhibitor cocktail (Roche) and cleared by centrifugation. Protein concentrations were determined by the Bio-Rad Protein Assay (Bio-Rad). Equal amounts of protein extracts were resolved using SDS-PAGE (NuPAGE; Invitrogen), transferred to a nitrocellulose membrane, and immunoblotted with primary antibodies indicated, followed by secondary antibodies labeled with either IRDye800 (Rockland) or Alexa Fluor 680 (Molecular Probes) and were visualized using a LI-COR Odyssey scanner. A complete list of primary antibodies is provided in the Extended Experimental Procedures.

Sphere Formation and Re-Plating Assay

Cells were harvested, counted and seeded into Ultra Low Attachment Culture 96-well plate (Corning Life Science, Catalog number 3261) at 10 or 100 cells per well. The seeded cells and formed spheres were maintained in low serum containing medium with 0.1% FBS or CS. The initiated spheres were observed twice and week. The numbers of formed spheres were counted one month after seeding. The spheres were harvested and re-seeded into 12-well or 24-well plate with complete growth medium at one sphere per well. The re-plated colonies were stained and visualized by 0.05% crystal violet staining (in 0.1% methanol).

Drug Sensitization Assay

Cells were first seeded into 96-well plates at 10,000 cells per well, and treated with prostratin (Santa Cruz Biotech, sc-203422A) for 72 hours. The dead cells were removed, and MTS assay (Promega, G5430) was performed for determining the percentage of viable cells, according to the manufacturer's instructions. DMSO was used as vehicle control and for normalization.

Quantitative PCR

Total RNAs were isolated and purified using QIAGEN RNAeasy kit. 1 μg RNA per specimen was reverse transcribed into cDNA using SuperScript™ First-Strand Synthesis System for RT-PCR (Invitrogen). Possible contamination of genomic DNA was excluded by treatments of DNase I. Quantitative real-time PCR array analysis was performed using SYBR Green (Applied Biosystem). Fold differences and statistical analysis were calculated using the GraphPad Prism 4.00 for Windows (GraphPad Software). The mouse Stem Cell Signaling RT$^2$Profiler PCR array on 96-well plate (PAMM-047Z) was purchased from SABiosciences.

TOPFlash and NFat Luciferase Assay

Cells were transfected with TOPFlash (Addgene#12456), FOPFlash (Addgene#12457) or pGL3-NFAT (Addgene#17870) luciferase reporter constructs by using Fugene6 (Roche). 48$^{th}$ hour post-transfection the luciferase activities in cell lysates were measured using Bright-Glo Luciferase Assay System (Promega) according to the manufacturer's instructions.

Immunohistochemistry

5 μm-thick pancreatic tissue microarrays (PAN241, PA242a, PA483b and T143) were purchased from Biomax, Inc. The deparaffinized tissues were unmasked with Cell Marque™ Trilogy reagent (ALS) in the electric rice cooker for 30 minutes. The slides were quenched by placing in H$_2$O$_2$/Methanol for 10 minutes at room temperature. The staining of human and mouse pancreatic tissues were using Histostain® SP kit (Invitrogen), and the whole procedure was performed according to the manufacturer's instructions. The dilution of primary antibodies was used according to product application note.

RNAscope In Situ Hybridization

To seek the signal-to-noise ratio of RNA ISH by amplifying target-specific signals but not background noise from nonspecific hybridization, we used a novel customer designed human Fzd8 target probe and RANSCOPE2.0 High Definition-Brown staining kit (Advanced Cell Diagnostics). The whole procedure was performed according to the manufacturer's instructions.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating a mutated K-Ras-expressing cancer in a subject, the method comprising administering to the subject a therapeutic amount of prostratin or a prostratin analog, wherein the prostratin analog has the structural formula:

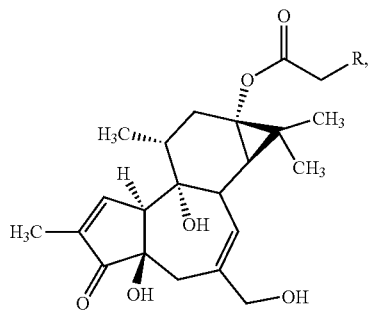

wherein R is ethyl, formate, propionate, butyrate, pentanoate, hexanoate, benzoate, phenyl acetate, cyclohexyl acetate, pentafluorophenyl acetate, 1-Naphthyl acetate, 2-Naphthyl acetate, (5,6,7,8)Tetrahydro-1-naphthyl acetate, biphenyl acetate, adamantyl acetate, or p-Benzyl phenyl acetate, or a salt or isomer thereof.

2. The method of claim 1, wherein the K-Ras-expressing cancer is a pancreatic cancer, a colorectal cancer, or a lung cancer.

3. The method of claim 2, wherein the K-Ras-expressing cancer is a pancreatic cancer.

4. The method of claim 3, wherein the pancreatic cancer is a pancreatic ductal adenocarcinoma.

5. The method of claim 1, wherein prostratin, or a salt or isomer thereof, is administered to the subject.

6. The method of claim 1, wherein a prostratin analog, or a salt or isomer thereof, is administered to the subject.

7. The method of claim 1, wherein the prostratin or the prostratin analog, or a salt or isomer thereof, is administered in combination with a chemotherapeutic agent.

8. The method of claim 7, wherein the chemotherapeutic agent is gemcitabine.

9. A method of treating a mutated K-Ras-expressing pancreatic cancer in a subject, the method comprising administering to the subject a therapeutic amount of prostratin or a prostratin analog, wherein the prostratin analog has the structural formula:

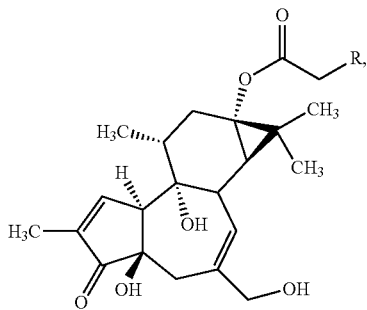

wherein R is ethyl, formate, propionate, butyrate, pentanoate, hexanoate, benzoate, phenyl acetate, cyclohexyl acetate, pentafluorophenyl acetate, 1-Naphthyl acetate, 2-Naphthyl acetate, (5,6,7,8)Tetrahydro-1-naphthyl acetate, biphenyl acetate, adamantyl acetate, or p-Benzyl phenyl acetate, or a salt or isomer thereof.

10. The method of claim 9, wherein the K-Ras-expressing pancreatic cancer is a pancreatic ductal adenocarcinoma.

11. The method of claim 9, wherein prostratin, or a salt or isomer thereof, is administered to the subject.

12. The method of claim 9, wherein a prostratin analog, or a salt or isomer thereof, is administered to the subject.

13. The method of claim 9, wherein the prostratin or the prostratin analog, or a salt or isomer thereof, is administered in combination with a chemotherapeutic agent.

14. The method of claim 13, wherein the chemotherapeutic agent is gemcitabine.

* * * * *

SEQUENCE LISTING

```
<160> NUMBER OF SEQ ID NOS: 6

<210> SEQ ID NO 1
<211> LENGTH: 23
<212> TYPE: PRT
<213> ORGANISM: Artificial Sequence
<220> FEATURE:
<223> OTHER INFORMATION: Synthetic construct
```

<400> SEQUENCE: 1

His Lys Glu Lys Met Ser Lys Asp Gly Lys Lys Lys Lys Lys Ser
1               5                  10                  15

Lys Thr Lys Cys Val Ile Met
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic construct

<400> SEQUENCE: 2

His Lys Glu Lys Met Ser Lys Asp Gly Lys Lys Lys Lys Lys Asp
1               5                  10                  15

Lys Thr Lys Cys Val Ile Met
            20

<210> SEQ ID NO 3
<211> LENGTH: 23
<212> TYPE: PRT
<213> ORGANISM: Artificial Sequence'
<220> FEATURE:
<223> OTHER INFORMATION: Synthetic construct

<400> SEQUENCE: 3

His Lys Glu Lys Met Ser Lys Asp Gly Lys Lys Lys Lys Lys Ala
1               5                  10                  15

Lys Thr Lys Cys Val Ile Met
            20

<210> SEQ ID NO 4
<211> LENGTH: 20
<212> TYPE: DNA
<213> ORGANISM: Artificial Sequence
<220> FEATURE:
<223> OTHER INFORMATION: Sythetic construct

<400> SEQUENCE: 4
atcctaaaag ccaccccact                                         20

<210> SEQ ID NO 5
<211> LENGTH: 20
<212> TYPE: DNA
<213> ORGANISM: Artificial Sequence
<220> FEATURE:
<223> OTHER INFORMATION: Synthetic constrcut

<400> SEQUENCE: 5
ctcaagttgg gggacaaaaa                                         20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
cacaggggag gtgatagcat                                         20